(12) United States Patent
Xiong et al.

(10) Patent No.: US 11,873,302 B2
(45) Date of Patent: Jan. 16, 2024

(54) SOLID FORMS OF A COMPOUND OF HBV CORE PROTEIN ALLOSTERIC MODIFIER

(71) Applicant: Hoffmann-La Roche Inc., Little Falls, NJ (US)

(72) Inventors: Jing Xiong, Shanghai (CN); Xuemei Wang, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/828,408

(22) Filed: Mar. 24, 2020

(65) Prior Publication Data

US 2020/0308178 A1 Oct. 1, 2020

(30) Foreign Application Priority Data

Mar. 25, 2019 (WO) ................ PCT/CN2019/079543

(51) Int. Cl.
| | | |
|---|---|---|
| A61K 31/505 | (2006.01) | |
| C07D 239/28 | (2006.01) | |
| C07D 487/04 | (2006.01) | |

(52) U.S. Cl.
CPC .................... C07D 487/04 (2013.01)

(58) Field of Classification Search
CPC ............................ A61K 31/505; C07D 239/28
USPC ......................................... 514/256; 544/333
See application file for complete search history.

(56) References Cited

U.S. PATENT DOCUMENTS

| | | | |
|---|---|---|---|
| 9,233,978 B2 | 1/2016 | Guo et al. | |
| 10,081,627 B2 | 9/2018 | Guo et al. | |
| 10,428,069 B2 | 10/2019 | Guo et al. | |
| 10,596,173 B2 | 3/2020 | Gao et al. | |
| 10,927,116 B2 | 2/2021 | Chen | |
| 2007/0072934 A1 | 3/2007 | Liang et al. | |
| 2014/0343032 A1 | 11/2014 | Guo et al. | |
| 2015/0252057 A1 | 9/2015 | Guo et al. | |
| 2016/0083383 A1 | 3/2016 | Guo et al. | |
| 2018/0000824 A1 | 1/2018 | Dai et al. | |
| 2019/0010155 A1 | 1/2019 | Chen et al. | |
| 2019/0275052 A1 | 9/2019 | Najera et al. | |
| 2019/0298726 A1 | 10/2019 | Dai et al. | |
| 2020/0062753 A1 | 2/2020 | Guo et al. | |

FOREIGN PATENT DOCUMENTS

| | | |
|---|---|---|
| CN | 101041658 A | 9/2007 |
| CN | 104650069 A | 5/2015 |
| CN | 104650069 B | 4/2019 |
| DE | 100 13 126 A1 | 9/2001 |
| WO | 01/68640 A1 | 9/2001 |
| WO | 01/68641 A1 | 9/2001 |
| WO | 01/68642 A1 | 9/2001 |
| WO | 01/68647 A1 | 9/2001 |
| WO | 02/094807 A1 | 11/2002 |
| WO | 2005/085462 A1 | 9/2005 |
| WO | 2006/033995 A2 | 3/2006 |
| WO | 2006/033995 A3 | 3/2006 |
| WO | 2008/090115 A1 | 7/2008 |
| WO | 2009/067547 A1 | 5/2009 |
| WO | 2009/103176 A1 | 8/2009 |
| WO | 2009/149377 A1 | 12/2009 |
| WO | 2010/023480 A1 | 3/2010 |
| WO | 2010/069147 A1 | 6/2010 |
| WO | 2012/019426 A1 | 2/2012 |

(Continued)

OTHER PUBLICATIONS

Allan et al., "Synthesis of analogs of GABA .15. preparation and resolution of some potent cyclopentene and cyclopentane derivatives" Aust. J. Chem 39:855-64 ( 1986).

(Continued)

*Primary Examiner* — Douglas M Willis
(74) *Attorney, Agent, or Firm* — Genentech, Inc.; Richard G. A. Bone

(57) ABSTRACT

The present invention relates to novel solid forms of compound (I),

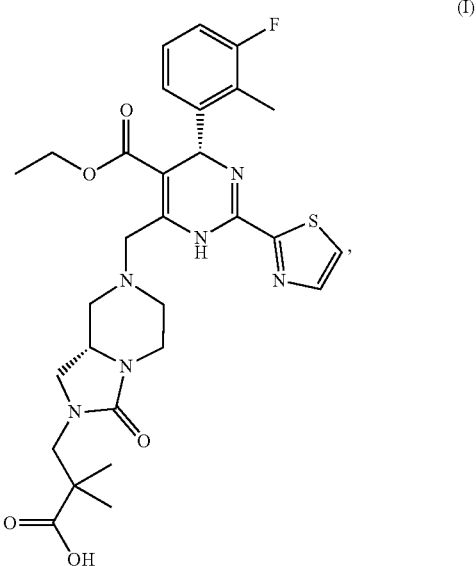

3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid and pharmaceutical compositions comprising solid forms thereof disclosed herein, which can be used as a HBV capsid inhibitor (or HBV Core Protein Allosteric Modifier), or for the treatment or prophylaxis of a viral disease in a patient relating to HBV infection or a disease caused by HBV infection.

20 Claims, 30 Drawing Sheets

(56) References Cited

FOREIGN PATENT DOCUMENTS

| WO | 2014/029193 | A1 | 2/2014 |
|---|---|---|---|
| WO | 2014/037480 | A1 | 3/2014 |
| WO | 2014/184328 | A1 | 11/2014 |
| WO | 2015/132276 | A1 | 9/2015 |
| WO | 2016/016196 | A1 | 2/2016 |
| WO | 2016/102438 | A1 | 6/2016 |
| WO | 2016-518432 | A | 6/2016 |
| WO | 2016/146598 | A1 | 9/2016 |
| WO | 2017/076791 | A1 | 5/2017 |
| WO | 2017/140750 | A1 | 8/2017 |
| WO | 2018/036941 | A1 | 3/2018 |
| WO | 2018/050571 | A1 | 3/2018 |
| WO | 2018/222910 | A1 | 12/2018 |
| WO | 2019/084020 | A1 | 12/2018 |
| WO | 2020/245246 | A1 | 12/2020 |
| WO | 2021/053126 | A1 | 3/2021 |

OTHER PUBLICATIONS

Brezillon et al., "Antiviral activity of Bay 41-4109 on hepatitis B virus in humanized Alb-uPA/SCID mice" PLOS ONE 6(12 SUPPL 1-6):e25096 (Dec. 2011).

Deres et al., "Inhibition of hepatitis B virus replication by drug-induced depletion of nucleocapsids" Science 299(5608):893-6 (2003).

Feld et al., "The phenylpropenamide derivative AT-130 blocks HBV replication at the level of viral RNA packaging" Antiviral Res 76:168-177 (2007).

Grygorenko et al., "Expedient synthesis of cis- and trans-3-aminocyclobutanecarboxylic acids" Synthetic Communications 41:1644-1649 (2011).

Guo et al., "Characterization of the intracellular deproteinized relaxed circular DNA of hepatitis B virus: an intermediate of covalently closed circular DNA formation" J Virol 81:12472-12484 (2007).

Caira et al., "Crystalline Polymorphism of Organic Compounds" Topics in Current Chemistry, 198: 164-208 (1998).

International Search Report—PCT/EP2020/057937 (w/Written Opinion),:pp. 1-16 (dated Aug. 14, 2020).

Malancona et al., "Identification of MK-5710 ((8aS)-8a-methyl-1,3-dioxo-2-[(1S,2R)-2-phenylcyclopropyl]-N-(1-phenyl-1H-pyrazol-5-yl)hexahydroimid azo[1,5-a]pyrazine-7(1H)-carboxamide), a potent smoothened antagonist for use in Hedgehog pathway dependent malignancies, Part 1" Bioorganic & Medicinal Chemistry Letters 21(15):4422-4428 (2011).

Mertin et al., "C-Alkylation of functionally substituted carbanions with cyclopropiminium ions: a new route to cyclopropane amino acids1" SYNLETT 2:87-89 (1991).

Sandstroem et al., "B-Amino acid substitutions and structure-based CoMFA modeling of hepatitis C virus NS3 protease inhibitors" Bioorgan Med Chem 16:5590-5605 (2008).

Sells et al., "Production of hepatitis B virus particles in Hep G2 cells transfected with cloned hepatitis B virus DNA" Proc. Natl. Acad. Sci USA 84:1005-1009 (1987).

Yuen et al., "Man-R07049389, a core 1-23 protein allosteric modulator, demonstrates robust decline in HBV DNA and HBV DNA in chronic HBV infected patients" Introduction (Apr. 10, 2019).

Zlotnick, A., et al., "A small molecule inhibits and misdirects assembly of hepatitis B virus capsids" J Virol 76(10):4848-4854 (May 2002).

Cruz-Cabeza et al., "Facts and Fictions about Polymorphism" Chem. Soc. Rev. 44:8619-8635 (2015).

SOLID FORMS OF A COMPOUND OF HBV CORE PROTEIN ALLOSTERIC MODIFIER

CROSS-REFERENCE TO RELATED APPLICATIONS

This application claims benefit of priority under 35 U.S.C. § 119(a) to International Application No. PCT/CN2019/079543 filed Mar. 25, 2019, the content of which is incorporated herein by reference in its entirety.

The present invention relates to novel solid forms of compound (I),

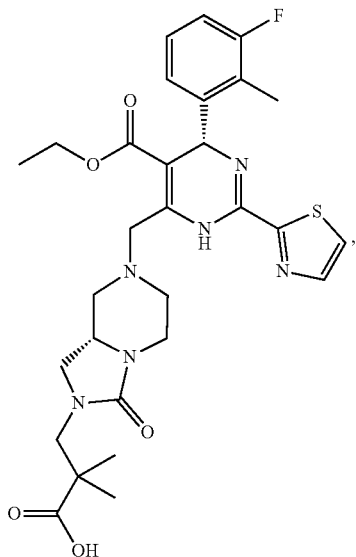

3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid and pharmaceutical compositions comprising solid forms thereof disclosed herein, which can be used as a HBV capsid inhibitor (or HBV Core Protein Allosteric Modifier), or for the treatment or prophylaxis of a viral disease in a patient relating to HBV infection or a disease caused by HBV infection.

BACKGROUND

HBV is a species of the hepadnaviridae family of viruses. HBV is a serious public health problem worldwide, with more than 400 million people especially in Asia-pacific regions chronically infected by this small enveloped DNA virus. Although most individuals seem to resolve the infection following acute symptoms, 15-40% of HBV patients will finally develop clinical diseases during their lifespan, most notably, hepatitis, liver cirrhosis, and hepatocellular carcinoma. Every year 500,000 to 1 million people die from the end stage of liver diseases caused by HBV infection.

HBV capsid protein plays essential roles in HBV replication. HBV has an icosahedral core comprising of 240 copies of the capsid (or core) protein. The predominant biological function of capsid protein is to act as a structural protein to encapsidate pre-genomic RNA and form immature capsid particles in the cytoplasm. This step is prerequisite for viral DNA replication. There has been a couple of capsid related anti-HBV inhibitors reported. For example, phenylpropenamide derivatives, including compounds named AT-61 and AT-130 (Feld J. et al. *Antiviral Research* 2007, 168-177), and a class of thiazolidin-4-ones from Valeant R&D (WO2006/033995), have been shown to inhibit pgRNA packaging. A recent study suggested that phenylpropenamides are, in fact, accelerators of HBV capsid assembly, and their actions result in the formation of empty capsids. These very interesting results illustrate the importance of the kinetic pathway in successful virus assembly.

Heteroaryldihydropyrimidines or HAP, including compounds named Bay 41-4109, Bay 38-7690 and Bay 39-5493, were discovered in a tissue culture-based screening (Deres K. et al. *Science* 2003, 893). These HAP analogs act as synthetic allosteric activators and are able to induce aberrant capsid formation that leads to degradation of the core protein. HAP analogs also reorganized core protein from preassembled capsids into noncapsid polymers, presumably by interaction of HAP with dimers freed during capsid 'breathing', the transitory breaking of individual intersubunit bonds. Bay 41-4109 was administered to HBV infected transgenic mouse or humanized mouse models and demonstrated in vivo efficacy with HBV DNA reduction (Deres K. et al. *Science* 2003, 893; Brezillon N. et al. *PLoS ONE* 2011, e25096). It was also shown that bis-ANS, a small molecule that acts as a molecular 'wedge' and interferes with normal capsid-protein geometry and capsid formation (Zlotnick A. et al. *J. Virol.* 2002, 4848-4854).

3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid (Compound (I)) was disclosed in WO2015/132276 as a HBV capsid inhibitor (or HBV Core Protein Allosteric Modifier).

It was found that Form D of compound (I) was physically unstable which leads to form change and makes it not suitable for further drug development. As one of the objectives of this patent, several novel solid forms were identified and characterized, showing significantly improved stability compared with Form D of compound (I). Developing novel forms of compound (I) with good processability or acceptable aqueous solubility is one of the objectives of current invention. Some novel solid forms enhance the developability of compound (I) fundamentally.

The present disclosure relates generally to the novel solid forms of compound (I) and processes to make them.

The physical stability of drug substances is an integral part of the systematic approach to the stability evaluation of pharmaceuticals due to its potential impacts on drug chemical stability performance and safety. The greater the stability is, the longer the shelf life could be. Therefore, the accelerated and long term stability testing used in this invention could be used to predict shelf lives.

Generally speaking, amorphous pharmaceuticals are markedly more soluble but less stable than their crystalline counterparts. In another embodiment, surprisingly, Form Amorphous of compound (I) significantly improved stability compared with Form D of compound (I).

In another embodiment, sodium salt Form J of compound (I) showed improved stability compared with Form D of compound (I) and improved solubility compared with some of other crystal forms of the parent compound (I). An in vivo PK study showed that Form J of compound (I) exhibited much slower absorption rate to reach Cmax. Therefore, sodium salt Form J is suitable to be formulated as sustained-release oral formulation. Although Form J converted to HCl salt immediately, its apparent solubility in FaSSIF increased with time. Therefore, sodium salt Form J could be developed as enteric release formulations to avoid conversion in SGF and achieve higher solubility in intestinal environment for better absorption.

In another embodiment, Form H of compound (I) is a mono-hydrate which showed improved stability compared with Form D of compound (I). Generally speaking, hydrated crystal forms thermodynamically show the lowest solubility in water. Form H shows unexpected higher water solubility than Form A. With acceptable solid state stability, Form H of compound (I) is more preferred with oral suspension formulation.

SUMMARY

The present invention relates to polymorphs, salts, solvates, co-crystals or combinations thereof and methods for the synthesis and production of solid forms of 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid.

One embodiment provided herein is an amorphous or solid form of compound (I) or solvates or combination thereof.

Another embodiment provided herein is an amorphous or solid form of compound (I), wherein the solid form is Form A, Form B, Form C, Form D, Form E, Form F, Form G, Form H, Form I, Form J, Form K, Form L, Form M, Form N, Form O, Form P, Form Q, Form R, Form S, Form T, Form U, Form V, Form W, Form X, or a combination thereof.

In another embodiment, the solid form of compound (I) is Form D that exhibits an X-ray powder diffraction (XRPD) pattern with characteristic peaks expressed in degrees 2-theta at 6.8°±0.2°, 13.0°±0.2°, 20.3°±0.2°, 27.1°±0.2°, 27.4°±0.2°, 28.8°±0.2° and 29.1°±0.2°.

In a further embodiment, the solid form of compound (I) is Form D that exhibits an X-ray powder diffraction (XRPD) pattern shown in FIG. 1.

In another embodiment, the solid form of compound (I) is Form A that exhibits an X-ray powder diffraction (XRPD) pattern with characteristic peaks expressed in degrees 2-theta at 10.0°±0.2°, 14.5°±0.2°, 15.4°±0.2°, 16.4°±0.2°, 19.4°±0.2°, 21.1°±0.2° and 23.2°±0.2°.

In a further embodiment, the solid form of compound (I) is Form A that exhibits an X-ray powder diffraction (XRPD) pattern with characteristic peaks expressed in degrees 2-theta at 10.0°±0.2°, 12.3°±0.2°, 13.2°±0.2°, 14.5°±0.2°, 15.4°±0.2°, 16.4°±0.2°, 19.4°±0.2°, 20.3°±0.2°, 21.1°±0.2°, 21.6°±0.2°, 23.2°±0.2°, 23.7°±0.2°, 24.5°±0.2°, 25.5°±0.2° and 26.8°±0.2°.

In a further embodiment, the solid form of compound (I) is Form A that exhibits an X-ray powder diffraction (XRPD) pattern shown in FIG. 2.

In another embodiment, the solid form of compound (I) is Form Amorphous that exhibits an X-ray powder diffraction (XRPD) pattern shown in FIG. 4.

In another embodiment, the solid form of compound (I) is Form B that exhibits an X-ray powder diffraction (XRPD) pattern with characteristic peaks expressed in degrees 2-theta at 3.9°±0.2°, 4.8°±0.2°, 7.3°±0.2°, 7.8°±0.2°, 10.7°±0.2°, 15.6°±0.2° and 19.5°±0.2°.

In a further embodiment, the solid form of compound (I) is Form B that exhibits an X-ray powder diffraction (XRPD) pattern with characteristic peaks expressed in degrees 2-theta at 3.9°±0.2°, 4.8°±0.2°, 7.3°±0.2°, 7.8°±0.2°, 10.7°±0.2°, 15.6°±0.2°, 16.2°±0.2°, 16.4°±0.2°, 19.5°±0.2°, 20.4°±0.2° and 21.7°±0.2°.

In a further embodiment, the solid form of compound (I) is Form B that exhibits an X-ray powder diffraction (XRPD) pattern shown in FIG. 5.

In another embodiment, the solid form of compound (I) is Form C that exhibits an X-ray powder diffraction (XRPD) pattern with characteristic peaks expressed in degrees 2-theta at 5.1°±0.2°, 10.6°±0.2°, 10.8°±0.2°, 12.1°±0.2°, 13.6°±0.2° and 13.9°±0.2°.

In a further embodiment, the solid form of compound (I) is Form C that exhibits an X-ray powder diffraction (XRPD) pattern shown in FIG. 6.

In another embodiment, the solid form of compound (I) is Form E that exhibits an X-ray powder diffraction (XRPD) pattern with characteristic peaks expressed in degrees 2-theta at 4.0°±0.2°, 5.1°±0.2°, 5.4°±0.2°, 10.2°±0.2°, 13.3°±0.2°, 15.5°±0.2° and 20.2°±0.2°.

In a further embodiment, the solid form of compound (I) is Form E that exhibits an X-ray powder diffraction (XRPD) pattern with characteristic peaks expressed in degrees 2-theta at 4.0°±0.2°, 5.1°±0.2°, 5.4°±0.2°, 10.2°±0.2°, 10.5°±0.2°, 11.8°±0.2°, 12.2°±0.2°, 13.3°±0.2°, 13.8°±0.2°, 14.6°±0.2°, 15.5°±0.2°, 15.8°±0.2°, 16.5°±0.2°, 19.5°±0.2°, 20.2°±0.2° and 21.9°±0.2°.

In a further embodiment, the solid form of compound (I) is Form E that exhibits an X-ray powder diffraction (XRPD) pattern shown in FIG. 7.

In another embodiment, the solid form of compound (I) is Form F that exhibits an X-ray powder diffraction (XRPD) pattern with characteristic peaks expressed in degrees 2-theta at 4.0°±0.2°, 4.9°±0.2°, 7.1°±0.2°, 15.8°±0.2°, 20.3°±0.2° and 21.9°±0.2°.

In a further embodiment, the solid form of compound (I) is Form F that exhibits an X-ray powder diffraction (XRPD) pattern with characteristic peaks expressed in degrees 2-theta at 4.0°±0.2°, 4.9°±0.2°, 7.1°±0.2°, 7.4°±0.2°, 7.9°±0.2°, 10.6°±0.2°, 11.9°±0.2°, 13.1°±0.2°, 13.3°±0.2°, 13.8°±0.2°, 15.8°±0.2°, 20.3°±0.2°, 21.0°±0.2° and 21.9°±0.2°.

In a further embodiment, the solid form of compound (I) is Form F that exhibits an X-ray powder diffraction (XRPD) pattern shown in FIG. 8.

In another embodiment, the solid form of compound (I) is Form G that exhibits an X-ray powder diffraction (XRPD) pattern with characteristic peaks expressed in degrees 2-theta at 3.7°±0.2°, 4.1°±0.2°, 5.0°±0.2°, 6.2°±0.2°, 7.7°±0.2°, 8.2°±0.2° and 17.1°±0.2°.

In a further embodiment, the solid form of compound (I) is Form G that exhibits an X-ray powder diffraction (XRPD) pattern with characteristic peaks expressed in degrees 2-theta at 3.7°±0.2°, 4.1°±0.2°, 5.0°±0.2°, 6.2°±0.2°, 7.7°±0.2°, 8.2°±0.2°, 11.3°±0.2°, 13.3°±0.2°, 13.8°±0.2°, 14.5°±0.2°, 16.3°±0.2°, 17.1°±0.2°, 19.3°±0.2°, 21.1°±0.2° and 23.3°±0.2°.

In a further embodiment, the solid form of compound (I) is Form G that exhibits an X-ray powder diffraction (XRPD) pattern shown in FIG. 9.

In another embodiment, the solid form of compound (I) is Form J that exhibits an X-ray powder diffraction (XRPD) pattern with characteristic peaks expressed in degrees 2-theta at 7.7°±0.2°, 9.7°±0.2°, 14.7°±0.2°, 15.9°±0.2°, 22.0°±0.2°, 23.4°±0.2°.

In a further embodiment, the solid form of compound (I) is Form J that exhibits an X-ray powder diffraction (XRPD) pattern with characteristic peaks expressed in degrees 2-theta at 7.7°±0.2°, 9.7°±0.2°, 11.5°±0.2°, 13.0°±0.2°, 14.7°±0.2°, 15.3°±0.2°, 15.9°±0.2°, 16.5°±0.2°, 19.0°±0.2°, 22.0°±0.2°, 22.6°±0.2°, 23.4°±0.2°, 23.9°±0.2°, 24.5°±0.2° and 25.3°±0.2°.

In a further embodiment, the solid form of compound (I) is Form J that exhibits an X-ray powder diffraction (XRPD) pattern shown in FIG. 10.

In a further embodiment, the solid form of compound (I) is Form J, wherein the Form J is the sodium salt of compound (I).

In another embodiment, the solid form of compound (I) is Form H that exhibits an X-ray powder diffraction (XRPD) pattern with characteristic peaks expressed in degrees 2-theta at 8.0°±0.2°, 9.7°±0.2°, 14.6°±0.2°, 15.7°±0.2°, 15.9°±0.2° and 24.1°±0.2°.

In a further embodiment, the solid form of compound (I) is Form H that exhibits an X-ray powder diffraction (XRPD) pattern with characteristic peaks expressed in degrees 2-theta at 6.8°±0.2°, 8.0°±0.2°, 9.7°±0.2°, 11.6°±0.2°, 14.6°±0.2°, 15.2°±0.2°, 15.7°±0.2°, 15.9°±0.2°, 18.9°±0.2°, 19.9°±0.2°, 22.7°±0.2°, 24.1°±0.2°, 24.5°±0.2° and 26.0°±0.2°.

In a further embodiment, the solid form of compound (I) is Form H that exhibits an X-ray powder diffraction (XRPD) pattern shown in FIG. 12.

In another embodiment, the solid form of compound (I) is Form I that exhibits an X-ray powder diffraction (XRPD) pattern with characteristic peaks expressed in degrees 2-theta at 6.4°±0.2°, 7.8°±0.2°, 9.9°±0.2°, 11.6°±0.2°, 16.2°±0.2° and 22.1°±0.2°.

In a further embodiment, the solid form of compound (I) is Form I that exhibits an X-ray powder diffraction (XRPD) pattern with characteristic peaks expressed in degrees 2-theta at 6.4°±0.2°, 7.8°±0.2°, 9.6°±0.2°, 9.9°±0.2°, 11.6°±0.2°, 13.0°±0.2°, 14.5°±0.2°, 15.0°±0.2°, 15.7°±0.2°, 16.2°±0.2°, 18.3°±0.2°, 22.1°±0.2°, 23.0°±0.2°, 24.3°±0.2° and 27.2°±0.2°.

In a further embodiment, the solid form of compound (I) is Form I that exhibits an X-ray powder diffraction (XRPD) pattern shown in FIG. 15.

In another embodiment, the solid form of compound (I) is Form K that exhibits an X-ray powder diffraction (XRPD) pattern with characteristic peaks expressed in degrees 2-theta at 5.4°±0.2°, 13.3°±0.2°, 15.9°±0.2°, 16.3°±0.2°, 18.0°±0.2° and 22.7°±0.2°.

In a further embodiment, the solid form of compound (I) is Form K that exhibits an X-ray powder diffraction (XRPD) pattern with characteristic peaks expressed in degrees 2-theta at 5.4°±0.2°, 13.3°±0.2°, 13.8°±0.2°, 14.8°±0.2°, 15.9°±0.2°, 16.3°±0.2°, 18.0°±0.2°, 19.5°±0.2°, 20.0°±0.2°, 21.7°±0.2°, 22.4°±0.2°, 22.7°±0.2°, 23.4°±0.2°, 24.1°±0.2° and 28.0°±0.2°.

In a further embodiment, the solid form of compound (I) is Form K that exhibits an X-ray powder diffraction (XRPD) pattern shown in FIG. 16.

In a further embodiment, the solid form of compound (I) is Form K, wherein the Form K is the hydrochloride salt of compound (I).

In another embodiment, the solid form of compound (I) is Form L that exhibits an X-ray powder diffraction (XRPD) pattern with characteristic peaks expressed in degrees 2-theta at 6.0°±0.2°, 11.8°±0.2°, 15.3°±0.2°, 15.8°±0.2°, 18.3°±0.2° and 24.4°±0.2°.

In a further embodiment, the solid form of compound (I) is Form L that exhibits an X-ray powder diffraction (XRPD) pattern with characteristic peaks expressed in degrees 2-theta at 6.0°±0.2°, 11.2°±0.2°, 11.8°±0.2°, 12.3°±0.2°, 13.1°±0.2°, 15.3°±0.2°, 15.8°±0.2°, 18.3°±0.2°, 18.7°±0.2°, 21.7°±0.2°, 22.5°±0.2°, 23.8°±0.2°, 24.4°±0.2°, 25.7°±0.2° and 27.7°±0.2°.

In a further embodiment, the solid form of compound (I) is Form L that exhibits an X-ray powder diffraction (XRPD) pattern shown in FIG. 17.

In a further embodiment, the solid form of compound (I) is Form L, wherein the Form L is the hydrochloride salt of compound (I).

In another embodiment, the solid form of compound (I) is Form M that exhibits an X-ray powder diffraction (XRPD) pattern with characteristic peaks expressed in degrees 2-theta at 5.3°±0.2°, 7.7°±0.2°, 10.7°±0.2°, 17.6°±0.2°, 19.0°±0.2° and 19.2°±0.2°.

In a further embodiment, the solid form of compound (I) is Form M that exhibits an X-ray powder diffraction (XRPD) pattern with characteristic peaks expressed in degrees 2-theta at 5.3°±0.2°, 7.7°±0.2°, 9.4°±0.2°, 10.7°±0.2°, 15.5°±0.2°, 17.2°±0.2°, 17.6°±0.2°, 19.0°±0.2°, 19.2°±0.2°, 19.8°±0.2° and 24.4°±0.2°.

In a further embodiment, the solid form of compound (I) is Form M that exhibits an X-ray powder diffraction (XRPD) pattern shown in FIG. 19.

In a further embodiment, the solid form of compound (I) is Form M, wherein the Form M is the sulfate salt of compound (I).

In another embodiment, the solid form of compound (I) is Form N that exhibits an X-ray powder diffraction (XRPD) pattern with characteristic peaks expressed in degrees 2-theta at 5.3°±0.2°, 10.7°±0.2°, 18.0°±0.2°, 18.7°±0.2°, 19.4°±0.2°, 20.3°±0.2°, 21.5°±0.2° and 24.7°±0.2°.

In a further embodiment, the solid form of compound (I) is Form N that exhibits an X-ray powder diffraction (XRPD) pattern shown in FIG. 20.

In a further embodiment, the solid form of compound (I) is Form N, wherein the Form N is the sulfate salt of compound (I).

In another embodiment, the solid form of compound (I) is Form O that exhibits an X-ray powder diffraction (XRPD) pattern with characteristic peaks expressed in degrees 2-theta at 4.9°±0.2°, 10.6°±0.2°, 14.3°±0.2°, 22.4°±0.2° and 22.9°±0.2°.

In a further embodiment, the solid form of compound (I) is Form O that exhibits an X-ray powder diffraction (XRPD) pattern with characteristic peaks expressed in degrees 2-theta at 4.9°±0.2°, 10.6°±0.2°, 13.2°±0.2°, 14.3°±0.2°, 16.9°±0.2°, 17.9°±0.2°, 19.1°±0.2°, 20.2°±0.2°, 21.1°±0.2°, 22.4°±0.2°, 22.9°±0.2°, 23.9°±0.2° and 24.4°±0.2°.

In a further embodiment, the solid form of compound (I) is Form O that exhibits an X-ray powder diffraction (XRPD) pattern shown in FIG. 21.

In a further embodiment, the solid form of compound (I) is Form O, wherein the Form O is the besylate salt of compound (I).

In another embodiment, the solid form of compound (I) is Form P that exhibits an X-ray powder diffraction (XRPD) pattern with characteristic peaks expressed in degrees 2-theta at 3.9°±0.2°, 7.7°±0.2°, 15.3°±0.2°, 21.5°±0.2°, 27.5°±0.2° and 31.8°35 0.2°.

In a further embodiment, the solid form of compound (I) is Form P that exhibits an X-ray powder diffraction (XRPD) pattern shown in FIG. 22.

In a further embodiment, the solid form of compound (I) is Form P, wherein the Form P is the potassium salt of compound (I).

In another embodiment, the solid form of compound (I) is Form Q that exhibits an X-ray powder diffraction (XRPD)

pattern with characteristic peaks expressed in degrees 2-theta at 7.9°±0.2°, 8.7°±0.2°, 13.2°±0.2°, 15.4°±0.2°, 21.8°±0.2°, 26.3°±0.2° and 29.3°±0.2°.

In a further embodiment, the solid form of compound (I) is Form Q that exhibits an X-ray powder diffraction (XRPD) pattern with characteristic peaks expressed in degrees 2-theta at 7.9°±0.2°, 8.7°±0.2°, 10.5°±0.2°, 11.0°±0.2°, 13.2°±0.2°, 15.4°±0.2°, 16.8°±0.2°, 17.4°±0.2°, 18.1°±0.2°, 18.5°±0.2°, 21.2°±0.2°, 21.8°±0.2°, 26.3°±0.2°, 26.7°±0.2° and 29.3°±0.2°.

In a further embodiment, the solid form of compound (I) is Form Q that exhibits an X-ray powder diffraction (XRPD) pattern shown in FIG. 23.

In a further embodiment, the solid form of compound (I) is Form Q, wherein the Form Q is the potassium salt of compound (I).

In another embodiment, the solid form of compound (I) is Form R that exhibits an X-ray powder diffraction (XRPD) pattern with characteristic peaks expressed in degrees 2-theta at 7.5°±0.2°, 7.8°±0.2°, 9.9°±0.2°, 14.8°±0.2°, 15.4°±0.2°, 15.7°±0.2° and 22.2°±0.2°.

In a further embodiment, the solid form of compound (I) is Form R that exhibits an X-ray powder diffraction (XRPD) pattern with characteristic peaks expressed in degrees 2-theta at 7.5°±0.2°, 7.8°±0.2°, 8.8°±0.2°, 9.9°±0.2°, 11.2°±0.2°, 11.7°±0.2°, 12.4°±0.2°, 14.8°±0.2°, 15.4°±0.2°, 15.7°±0.2°, 17.2°±0.2°, 22.2°±0.2° and 26.3°±0.2°.

In a further embodiment, the solid form of compound (I) is Form R that exhibits an X-ray powder diffraction (XRPD) pattern shown in FIG. 24.

In a further embodiment, the solid form of compound (I) is Form R, wherein the Form R is the potassium salt of compound (I).

In another embodiment, the solid form of compound (I) is Form S that exhibits an X-ray powder diffraction (XRPD) pattern with characteristic peaks expressed in degrees 2-theta at 8.3°±0.2°, 8.7°±0.2°, 13.7°±0.2°, 15.8°±0.2°, 18.0°±0.2° and 21.7°±0.2°.

In a further embodiment, the solid form of compound (I) is Form S that exhibits an X-ray powder diffraction (XRPD) pattern with characteristic peaks expressed in degrees 2-theta at 8.3°±0.2°, 8.7°±0.2°, 11.0°±0.2°, 11.2°±0.2°, 13.4°±0.2°, 13.7°±0.2°, 15.8°±0.2°, 16.6°±0.2°, 18.0°±0.2°, 20.9°±0.2°, 21.7°±0.2°, 24.5°±0.2°, 26.2°±0.2°, 26.7°±0.2° and 28.6°±0.2°.

In a further embodiment, the solid form of compound (I) is Form S that exhibits an X-ray powder diffraction (XRPD) pattern shown in FIG. 25.

In a further embodiment, the solid form of compound (I) is Form S, wherein the Form S is the potassium salt of compound (I).

In another embodiment, the solid form of compound (I) is Form T that exhibits an X-ray powder diffraction (XRPD) pattern with characteristic peaks expressed in degrees 2-theta at 8.0°±0.2°, 10.8°±0.2°, 11.1°±0.2°, 13.3°±0.2°, 15.5°±0.2°, 21.5°±0.2° and 31.6°±0.2°.

In a further embodiment, the solid form of compound (I) is Form T that exhibits an X-ray powder diffraction (XRPD) pattern shown in FIG. 26.

In a further embodiment, the solid form of compound (I) is Form T, wherein the Form T is the calcium salt of compound (I).

In another embodiment, the solid form of compound (I) is Form U that exhibits an X-ray powder diffraction (XRPD) pattern with characteristic peaks expressed in degrees 2-theta at 7.5°±0.2°, 10.1°±0.2°, 10.6°±0.2°, 13.7°±0.2°, 18.9°±0.2°, 20.3°±0.2° and 21.0°±0.2°.

In a further embodiment, the solid form of compound (I) is Form U that exhibits an X-ray powder diffraction (XRPD) pattern with characteristic peaks expressed in degrees 2-theta at 7.5°±0.2°, 9.6°±0.2°, 10.1°±0.2°, 10.6°±0.2°, 11.9°±0.2°, 12.6°±0.2°, 12.9°±0.2°, 13.7°±0.2°, 16.2°±0.2°, 17.8°±0.2°, 18.9°±0.2°, 20.3°±0.2° and 21.0°±0.2°.

In a further embodiment, the solid form of compound (I) is Form U that exhibits an X-ray powder diffraction (XRPD) pattern shown in FIG. 27.

In a further embodiment, the solid form of compound (I) is Form U, wherein the Form U is the calcium salt of compound (I).

In another embodiment, the solid form of compound (I) is Form V that exhibits an X-ray powder diffraction (XRPD) pattern with characteristic peaks expressed in degrees 2-theta at 5.6°±0.2°, 8.5°±0.2°, 14.2°±0.2°, 16.2°±0.2°, 21.9°±0.2° and 22.4°±0.2°.

In a further embodiment, the solid form of compound (I) is Form V that exhibits an X-ray powder diffraction (XRPD) pattern shown in FIG. 28.

In a further embodiment, the solid form of compound (I) is Form V, wherein the Form V is the ammonium salt of compound (I).

In another embodiment, the solid form of compound (I) is Form W that exhibits an X-ray powder diffraction (XRPD) pattern with characteristic peaks expressed in degrees 2-theta at 6.2°±0.2°, 7.5°±0.2°, 7.8°±0.2°, 11.4°±0.2°, 15.8°±0.2° and 21.4°±0.2°.

In a further embodiment, the solid form of compound (I) is Form W that exhibits an X-ray powder diffraction (XRPD) pattern with characteristic peaks expressed in degrees 2-theta at 6.2°±0.2°, 6.6°±0.2°, 7.5°±0.2°, 7.8°±0.2°, 9.5°±0.2°, 9.8°±0.2°, 11.4°±0.2°, 12.5°±0.2°, 13.5°±0.2°, 14.5°±0.2°, 15.8°±0.2°, 19.8°±0.2°, 21.4°±0.2°, 22.5°±0.2°, 24.0°±0.2° and 26.5°±0.2°.

In a further embodiment, the solid form of compound (I) is Form W that exhibits an X-ray powder diffraction (XRPD) pattern shown in FIG. 29.

In a further embodiment, the solid form of compound (I) is Form W, wherein the Form W is the ammonium salt of compound (I).

In another embodiment, the solid form of compound (I) is Form X that exhibits an X-ray powder diffraction (XRPD) pattern with characteristic peaks expressed in degrees 2-theta at 8.6°±0.2°, 11.1°±0.2°, 11.4°±0.2°, 14.3°±0.2°, 16.0°±0.2°, 16.3°±0.2° and 22.0°±0.2°.

In a further embodiment, the solid form of compound (I) is Form X that exhibits an X-ray powder diffraction (XRPD) pattern with characteristic peaks expressed in degrees 2-theta at 7.6°±0.2°, 8.6°±0.2°, 11.1°±0.2°, 11.4°±0.2°, 12.6°±0.2°, 14.3°±0.2°, 16.0°±0.2°, 16.3°±0.2°, 19.8°±0.2°, 21.5°±0.2°, 22.0°±0.2° and 23.2°±0.2°.

In a further embodiment, the solid form of compound (I) is Form X that exhibits an X-ray powder diffraction (XRPD) pattern shown in FIG. 30.

In a further embodiment, the solid form of compound (I) is Form X, wherein the Form X is the ammonium salt of compound (I).

Another embodiment provided herein is a pharmaceutical composition comprising the solid forms disclosed herein and a pharmaceutically acceptable carrier, excipient, diluent, adjuvant, vehicle, or a combination thereof.

Another embodiment provided herein is the use of the solid form disclosed herein or the pharmaceutical composition for the manufacture of a medicament for the treatment or prophylaxis of a viral disease in a patient.

In another embodiment, the viral disease disclosed herein is HBV infection or a disease caused by HBV infection.

Another embodiment provided herein is a method for the treatment or prophylaxis of HBV infection or a disease caused by HBV infection, which method comprises administering a therapeutically effective amount of the solid form or the pharmaceutical composition disclosed herein.

ABBREVIATIONS

ACN Acetonitrile
$C_{max}$ Maximum concentration observed
DSC Differential Scanning Calorimetry
EtOAc Ethyl acetate
FaSSIF Fasted State Simulated Intestinal Fluid
IPA Isopropanol
IPAc Isopropyl acetate
IPE Diisopropyl ether
Pos. Position
Rel. Int. Relative Intensity
RT Room temperature
SGF Simulated Gastric Fluid
TGA Thermal Gravimetric Analysis
$T_{max}$ Time at which the maximum concentration (Cmax) is observed
XRPD X-ray powder diffraction

EXAMPLES

The invention will be more fully understood by reference to the following examples. They should not, however, be construed as limiting the scope of the invention.

HPLC Method for Chemical Purity and Assay Test
HPLC condition is disclosed here in Table 1.

TABLE 1

| HPLC conditions for chemical purity and assay test | | | |
|---|---|---|---|
| Instrument | Agilent 1260 HPLC system | | |
| Column | Waters Xbridge C8 (4.6 × 150 mm × 3.5 µm) | | |
| Oven temperature | 30° C. | | |
| Mobile phase | A: 0.12% TFA in water | | |
|  | B: 0.12% TFA in ACN | | |
| Gradient program | Time (min) | A % | B % |
|  | 0.00 | 80 | 20 |
|  | 15.00 | 50 | 50 |
|  | 20.00 | 10 | 90 |
|  | 25.00 | 10 | 90 |
|  | 25.01 | 80 | 20 |
|  | 30.00 | 80 | 20 |
| Flow rate | 1.0 mL/min | | |
| Detector | UV 299 nm | | |
| Nominal concentration | 0.5 mg/mL | | |
| Diluent | ACN:water, 1:1 | | |
| Injection volume | 10 µL | | |
| Retention Time | ~12.7 min | | |

Example 1

Preparation of Form D of Compound (I)

A solution of 10 mg of compound (I) in 5 mL n-propanol was placed at room temperature and evaporated to dryness.

Figure 1:
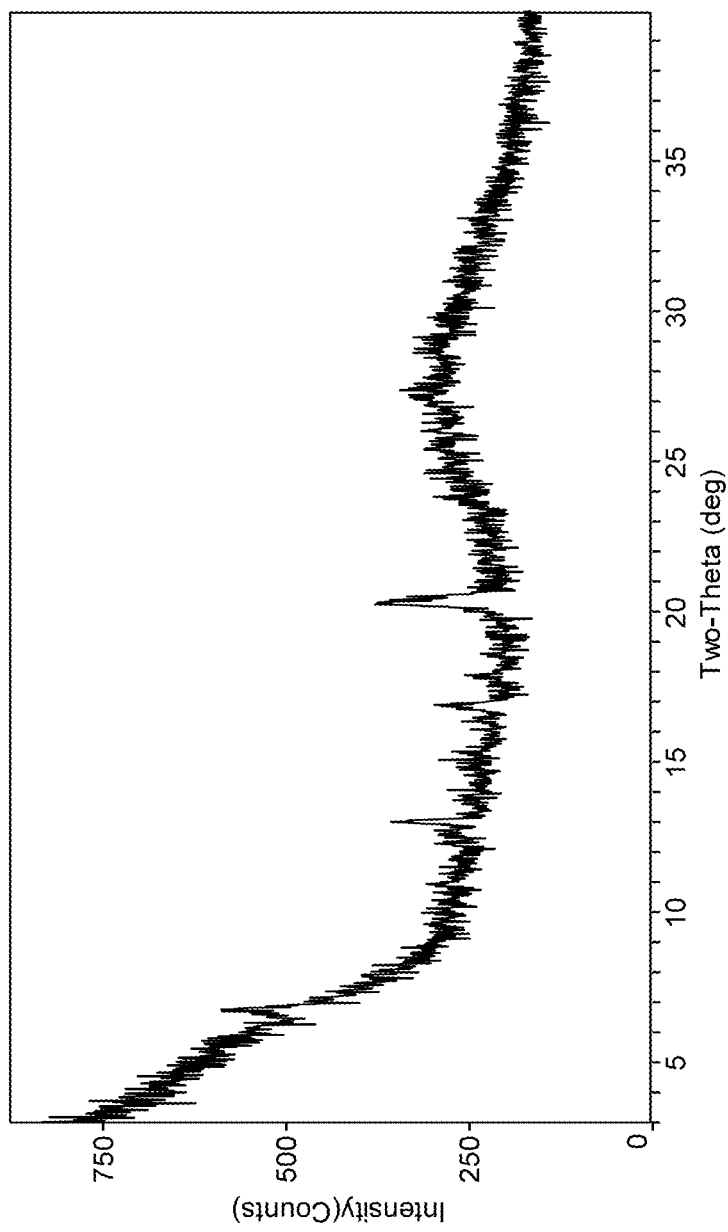
FIG. 1 X-ray powder diffraction pattern for Form D
FIG. 2 X-ray powder diffraction pattern for Form A
FIG. 3 X-ray crystal structure of Form A
FIG. 4 X-ray powder diffraction pattern for Form Amorphous
FIG. 5 X-ray powder diffraction pattern for Form B
FIG. 6 X-ray powder diffraction pattern for Form C
FIG. 7 X-ray powder diffraction pattern for Form E
FIG. 8 X-ray powder diffraction pattern for Form F
FIG. 9 X-ray powder diffraction pattern for Form G
FIG. 10 X-ray powder diffraction pattern for of sodium salt Form J
FIG. 11 X-ray crystal structure of sodium salt Form J
FIG. 12 X-ray powder diffraction pattern for Form H
FIG. 13 DSC thermogram of Form H
FIG. 14 TGA diagram of Form H
FIG. 15 X-ray powder diffraction pattern for Form I
FIG. 16 X-ray crystal structure of HCl salt Form K
FIG. 17 X-ray powder diffraction pattern for HCl salt Form L
FIG. 18 X-ray crystal structure of HCl salt Form L
FIG. 19 X-ray powder diffraction pattern for $H_2SO_4$ salt Form M
FIG. 20 X-ray powder diffraction pattern for $H_2SO_4$ salt Form N
FIG. 21 X-ray powder diffraction pattern for besylate salt Form O
FIG. 22 X-ray powder diffraction pattern for potassium salt Form P
FIG. 23 X-ray powder diffraction pattern for potassium salt Form Q
FIG. 24 X-ray powder diffraction pattern for potassium salt Form R
FIG. 25 X-ray powder diffraction pattern for potassium salt Form S
FIG. 26 X-ray powder diffraction pattern for calcium salt Form T
FIG. 27 X-ray powder diffraction pattern for calcium salt Form U
FIG. 28 X-ray powder diffraction pattern for ammonium salt Form V
FIG. 29 X-ray powder diffraction pattern for ammonium salt Form W
FIG. 30 X-ray powder diffraction pattern for ammonium salt Form X

Solids were obtained and characterized by XRPD. The XRPD pattern of Form D of compound (I) is shown in FIG. 1. Major peaks and their related intensities in the XRPD pattern are shown in table below.

Characterization Method

XRPD: Bruker D8 Advance diffractometer X-ray powder diffractometer with Cu-Kα radiation. Tube voltage was 40 KV and tube current was 40 mA. Scan range was from 3 to 40 degree 2-theta. The step size was 0.02° at a scanning speed of 6°/min.

TABLE 2

| X-ray powder diffraction peaks of Form D of compound (I) | |
|---|---|
| Pos. [°2-theta] | Rel. Int. [%] |
| 6.8 | 100 |
| 13.0 | 61 |
| 15.3 | 46 |
| 16.9 | 50 |
| 20.3 | 64 |
| 27.1 | 56 |
| 27.4 | 56 |

TABLE 2-continued

X-ray powder diffraction peaks of Form D of compound (I)

| Pos. [°2-theta] | Rel. Int. [%] |
|---|---|
| 28.8 | 55 |
| 29.1 | 55 |

Example 2

Alternative Preparation of Form D of Compound (I)

A solution of 10 mg of compound (I) in 5 mL a mixture of n-propanol and 2-butanol (2:8, v:v) was placed at room temperature and evaporated to dryness.

The solid was collected for XRPD analysis. The XRPD pattern of the solid was the same as that in Table 2 and confirmed to be Form D of compound (I).

Example 3

Preparation of Form A of Compound (I)

A solution of 10 mg of compound (I) in 10 mL acetone was placed at room temperature and evaporated to dryness.

Figure 2:
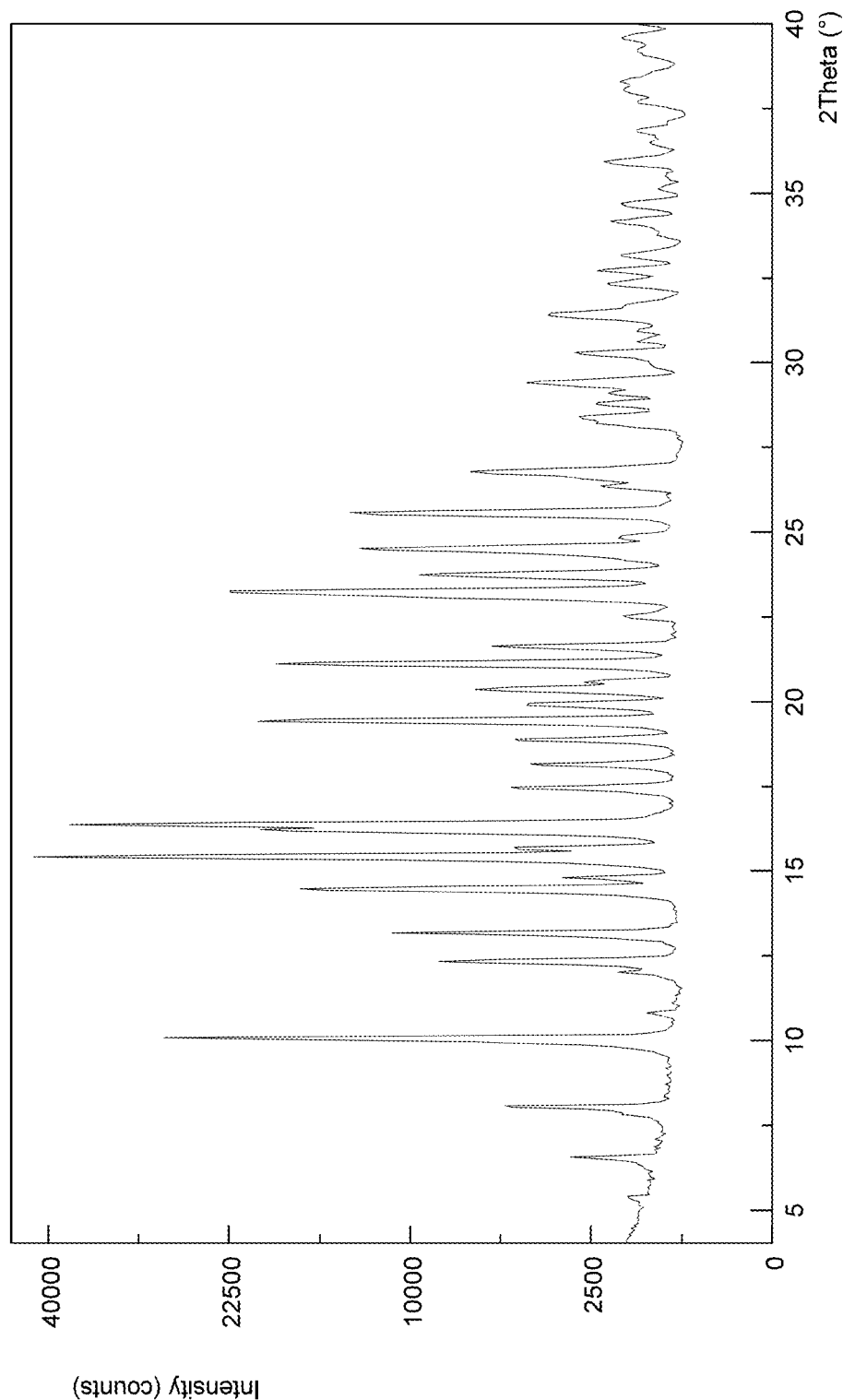

The XRPD pattern of Form A of compound (I) is shown in FIG. 2. Major peaks and their related intensities in the XRPD pattern are shown in table below.

Experimental Conditions

XRPD: PANalytical EMPYREAN X-ray powder diffractometer with Cu-Kα radiation. Tube voltage was 40 KV and tube current was 40 mA. Scan range was from 4 to 40 degree 2-theta. The step size was 0.053° at a scanning speed of 10.504°/min.

TABLE 3

X-ray powder diffraction peaks of Form A of compound (I)

| Pos. [°2-theta] | Rel. Int. [%] |
|---|---|
| 5.3 | 1 |
| 6.5 | 4 |
| 8.0 | 12 |
| 10.0 | 64 |
| 10.8 | 1 |
| 12.3 | 17 |
| 13.2 | 22 |
| 14.5 | 40 |
| 14.8 | 6 |
| 15.4 | 100 |
| 16.4 | 89 |
| 17.4 | 11 |
| 18.1 | 9 |
| 18.9 | 11 |
| 19.4 | 46 |
| 19.9 | 10 |
| 20.3 | 14 |
| 21.1 | 45 |
| 21.6 | 13 |
| 22.5 | 2 |
| 23.2 | 54 |
| 23.7 | 21 |
| 24.5 | 29 |
| 25.5 | 31 |
| 26.8 | 15 |
| 28.4 | 5 |
| 28.8 | 4 |
| 29.4 | 9 |
| 30.3 | 5 |
| 31.4 | 7 |
| 32.3 | 3 |
| 32.7 | 4 |
| 33.1 | 3 |
| 34.2 | 3 |
| 34.7 | 2 |
| 35.9 | 3 |
| 36.8 | 2 |
| 37.7 | 2 |
| 38.2 | 2 |
| 39.2 | 1 |
| 39.6 | 1 |

Figure 3:
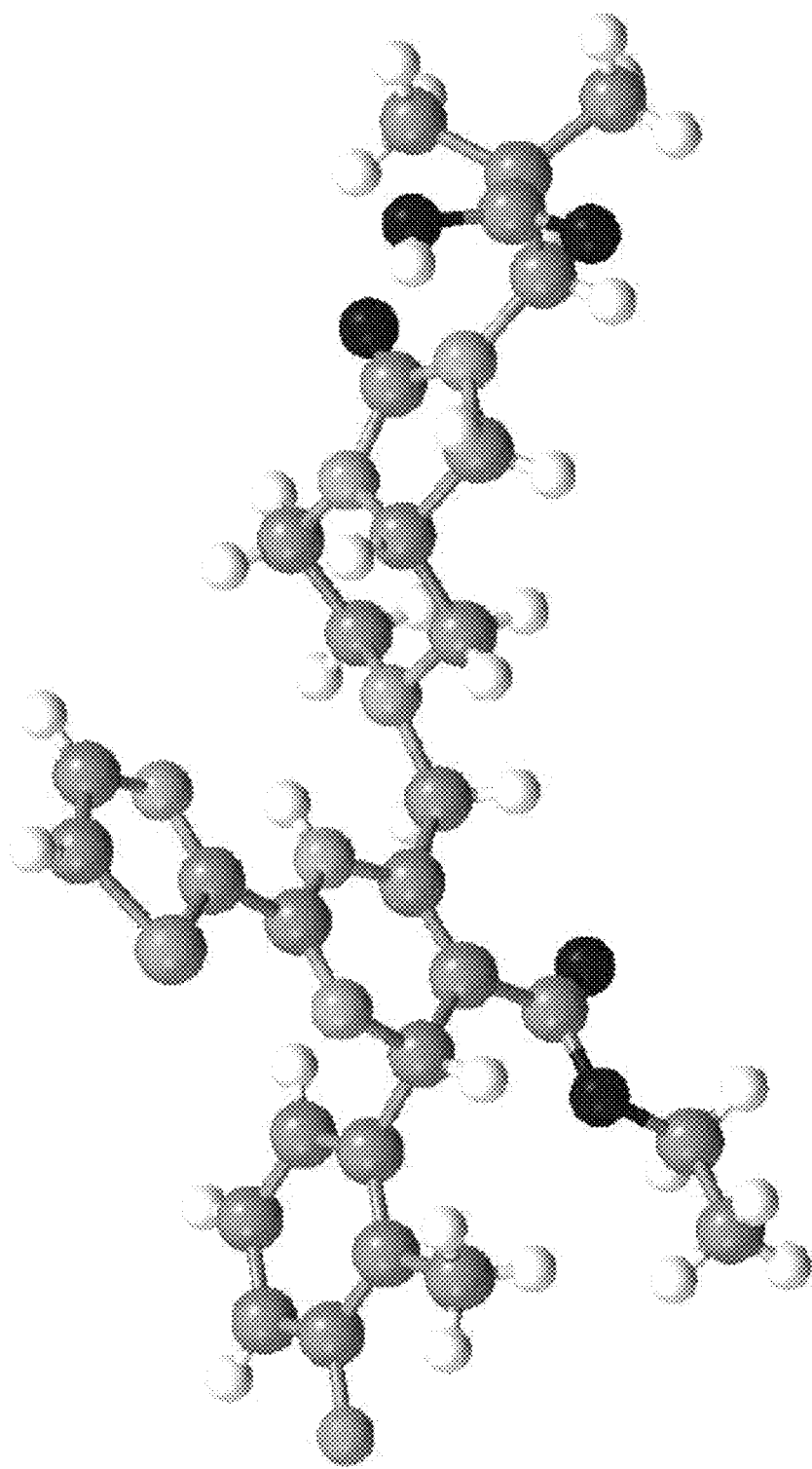

FIG. 3 shows the X-ray structure of Form A. The single crystal X-ray intensity data were collected at 296 K using a Bruker SMART APEX II with Cu-K-alpha-radiation (1.54 Å). Structure solution and refinement was performed using the ShelXTL software (Bruker AXS, Karlsruhe). The crystal data and structure refinement is shown in Table 4.

TABLE 4

Single crystal structural data of Forms A

| | |
|---|---|
| Crystal form | Form A |
| Solid form description | Polymorph |
| Measuring Temperature | 296 K |
| Crystal system | Monoclinic |
| Space group | P $2_1$ |
| Unit cell dimensions | |
| a= | 7.4967(2) Å |
| b= | 12.1773(2) Å |
| c= | 18.5541(4) Å |
| α= | 90° |
| β= | 94.4110(10)° |
| γ= | 90° |
| Cell volume | 1688.78(6) Å$^3$ |
| API molecules in unit cell | 4 |
| Calculated density | 1.386 g/cm$^3$ |

Example 4

Alternative preparation of Form A of Compound (I)

A solution of 10 mg of compound (I) in 1 mL ethyl acetate was placed at room temperature and evaporated to dryness.

The solid was collected for XRPD analysis. The XRPD pattern of the solid was the same as that in Table 3 and confirmed to be Form A of compound (I).

Example 5

Alternative Preparation of Form A of Compound (I)

A solution of 10 mg of compound (I) in 2 mL isopropyl acetate was placed at room temperature and evaporated to dryness.

The solid was collected for XRPD analysis. The XRPD pattern of the solid was the same as that in Table 3 and confirmed to be Form A of compound (I).

Example 6

Alternative Preparation of Form A of Compound (I)

A solution of 10 mg of compound (I) in 4 mL acetonitrile was placed at room temperature and evaporated to dryness.

The solid was collected for XRPD analysis. The XRPD pattern of the solid was the same as that in Table 3 and confirmed to be Form A of compound (I).

Example 7

Preparation of Form Amorphous of Compound (I)

Figure 4:
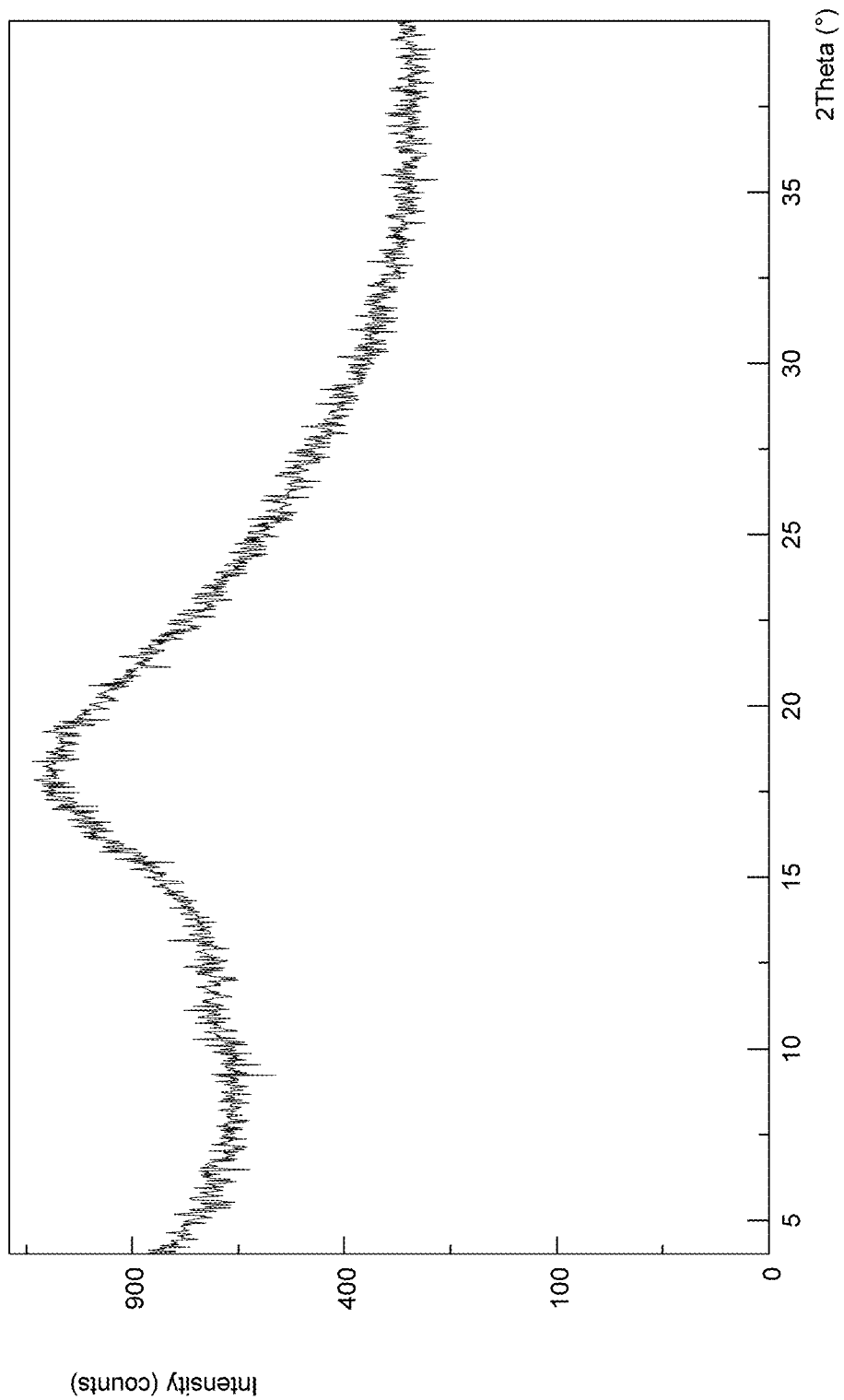

A solution of 500 mg of compound (I) in 10 mL dichloromethane was rapidly evaporated using a rotary evaporator. The solid was dried at 30° C. overnight. The solid was analyzed by XRPD. The result is shown in FIG. 4.

Characterization Method

XRPD: PANalytical EMPYREAN X-ray powder diffractometer with Cu-Kα radiation. Tube voltage was 40 KV and tube current was 40 mA. Scan range was from 4 to 40 degree 2-theta. The step size was 0.053° at a scanning speed of 10.504°/min.

Example 8

Alternative Preparation of Form Amorphous of Compound (I)

A solution of 10 mg of compound (I) in 1 mL methanol was placed at room temperature and evaporated to dryness.

The solid was collected for XRPD analysis. The XRPD pattern of the solid was the same as that in FIG. 4 and confirmed to be Form Amorphous of compound (I).

Example 9

Alternative Preparation of Form Amorphous of Compound (I)

A solution of 10 mg of compound (I) in 1 mL mixture solvents of methanol and dichloromethane (50:50, v:v) was placed at room temperature and evaporated to dryness.

The solid was collected for XRPD analysis. The XRPD pattern of the solid was the same as that in FIG. 4. and confirmed to be Form Amorphous of compound (I).

Example 10

Preparation of Form B of Compound (I)

Approximate 50 mg of Form Amorphous of compound (I) as prepared in Example 7 was weighed and transferred to a glass vial. 0.4 mL ethanol was added to form a suspension. The vial was mounted to a shaker and kept shaking at 25° C. with 1200 rpm for 3 min.

Figure 5:
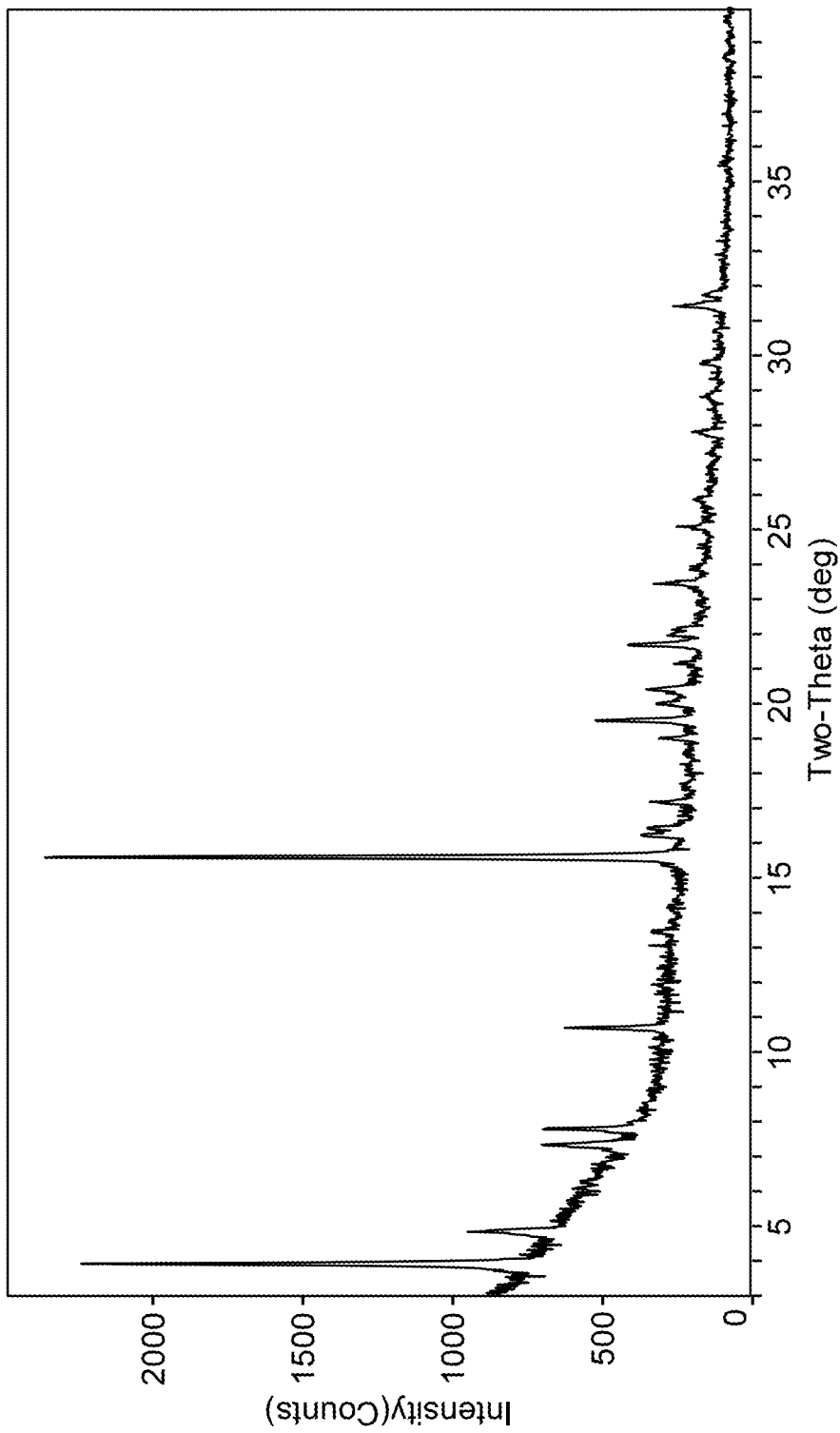

The XRPD pattern of Form B of compound (I) is shown in FIG. 5. Major peaks and their related intensities in the XRPD pattern are shown in table below.

Characterization Method

XRPD: Bruker D8 Advance diffractometer X-ray powder diffractometer with Cu-Kα radiation. Tube voltage was 40 KV and tube current was 40 mA. Scan range was from 3 to 40 degree 2-theta. The step size was 0.02° at a scanning speed of 6°/min.

TABLE 5

X-ray powder diffraction peaks of Form B of compound (I)

| Pos. [°2-theta] | Rel. Int. [%] |
| --- | --- |
| 3.9 | 95 |
| 4.8 | 40 |
| 7.3 | 30 |
| 7.8 | 29 |
| 10.7 | 26 |
| 11.9 | 14 |
| 15.6 | 100 |
| 16.2 | 16 |
| 16.4 | 15 |
| 17.2 | 14 |

TABLE 5-continued

X-ray powder diffraction peaks of Form B of compound (I)

| Pos. [°2-theta] | Rel. Int. [%] |
| --- | --- |
| 19.0 | 13 |
| 19.5 | 22 |
| 20.0 | 13 |
| 20.4 | 15 |
| 21.7 | 17 |
| 22.0 | 11 |
| 23.5 | 14 |
| 23.9 | 9 |
| 25.1 | 10 |
| 25.9 | 8 |
| 27.8 | 8 |
| 28.8 | 7 |
| 29.8 | 7 |
| 31.4 | 11 |
| 31.7 | 7 |
| 35.5 | 5 |

Example 11

Preparation of Form C of Compound (I)

Approximate 50 mg of Form Amorphous of compound (I) as prepared in Example 7 was weighed and transferred to a glass vial. 0.5 mL a mixture of ethanol and methyl cyclohexane (1:4, v:v) was added to form a suspension. The suspension was agitated for 10 minutes.

Figure 6:
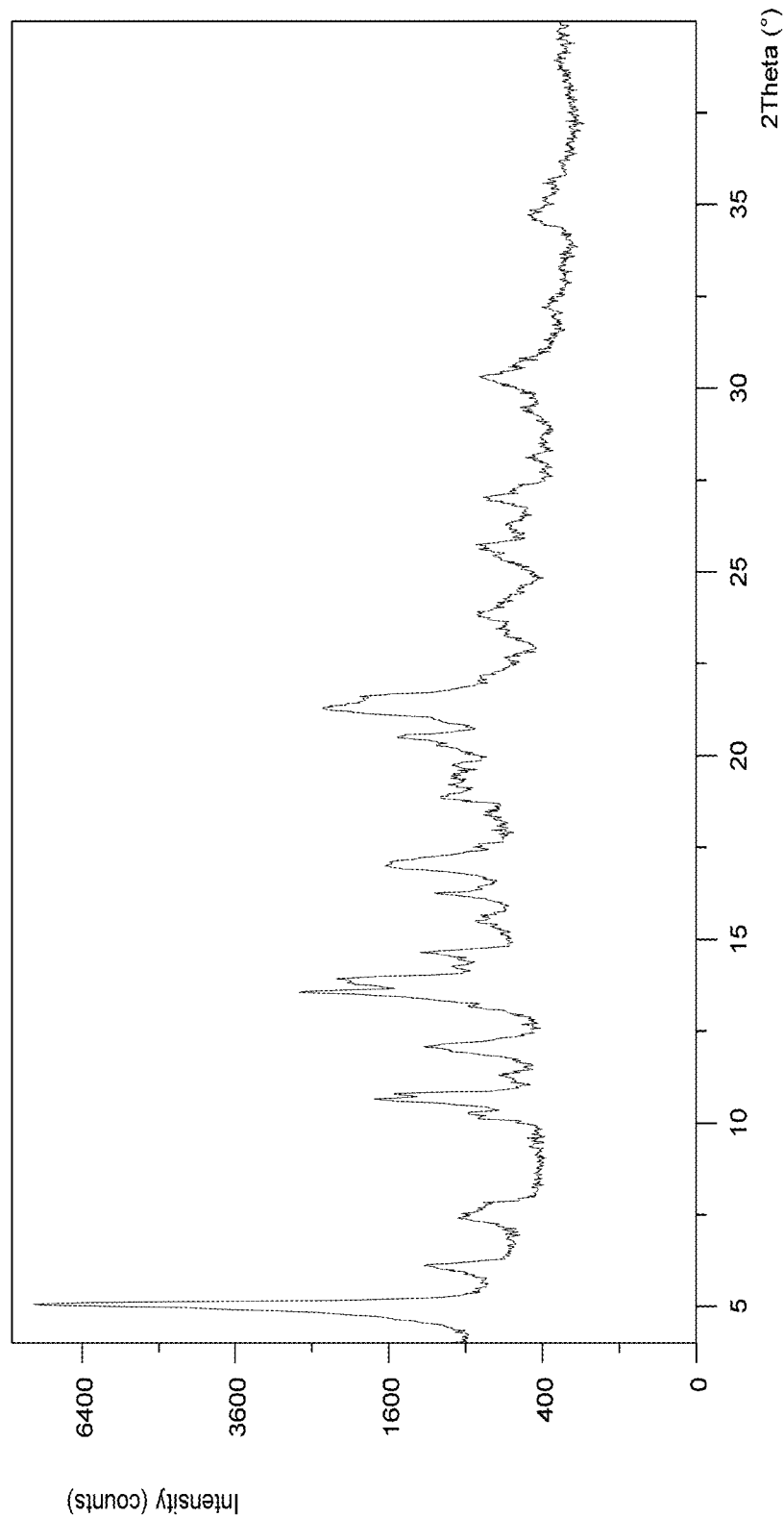
Figure 7:
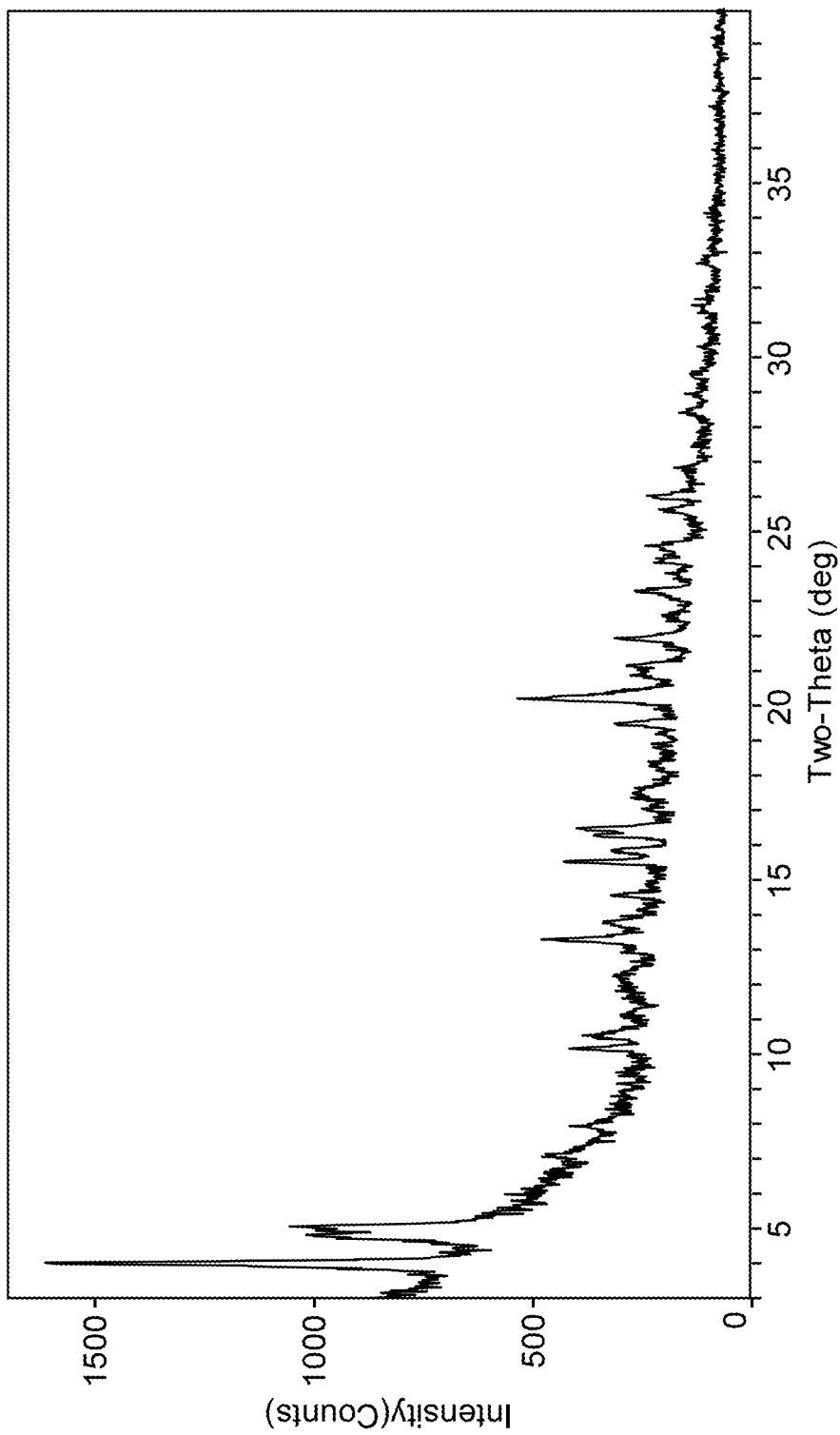

The solid was collected for XRPD analysis. The XRPD pattern of Form C of compound (I) is shown in FIG. 6. Major peaks and their related intensities in the XRPD pattern are shown in table below.

Characterization Method

XRPD: PANalytical EMPYREAN X-ray powder diffractometer with Cu-Kα radiation. Tube voltage was 40 KV and tube current was 40 mA. Scan range was from 4 to 40 degree 2-theta. The step size was 0.026° at a scanning speed of 3.348°/min.

TABLE 6

X-ray powder diffraction peaks of Form C of compound (I)

| Pos. [°2-theta] | Rel. Int. [%] |
| --- | --- |
| 5.1 | 100 |
| 6.1 | 9 |
| 7.4 | 6 |
| 7.8 | 4 |
| 10.2 | 6 |
| 10.6 | 19 |
| 10.8 | 16 |
| 11.3 | 3 |
| 12.1 | 12 |
| 13.6 | 33 |
| 13.9 | 24 |
| 14.6 | 9 |
| 15.5 | 2 |
| 16.2 | 8 |

Example 12

Preparation of Form E of Compound (I)

Approximate 10 mg of Form Amorphous of compound (I) as prepared in Example 7 was weighed and transferred to a centrifuge tube. The tube was placed inside a closed container filled with n-heptane, and let sit for 16 h.

The solid was collected and analyzed by XRPD. The XRPD pattern of Form E of compound (I) is shown in FIG.

7. Major peaks and their related intensities in the XRPD pattern are shown in Table below.

Characterization Method

XRPD: Bruker D8 Advance diffractometer X-ray powder diffractometer with Cu-Kα radiation. Tube voltage was 40 KV and tube current was 40 mA. Scan range was from 3 to 40 degree 2-theta. The step size was 0.02° at a scanning speed of 6°/min.

TABLE 7

X-ray powder diffraction peaks of Form E of compound (I)

| Pos. [°2-theta] | Rel. Int. [%] |
|---|---|
| 4.0 | 100 |
| 5.1 | 65 |
| 5.4 | 39 |
| 10.2 | 26 |
| 10.5 | 24 |
| 11.8 | 19 |
| 12.2 | 20 |
| 12.9 | 18 |
| 13.3 | 30 |
| 13.8 | 21 |
| 14.6 | 20 |
| 15.5 | 26 |
| 15.8 | 20 |
| 16.5 | 25 |
| 17.0 | 15 |
| 17.5 | 17 |
| 19.5 | 19 |
| 20.2 | 33 |
| 21.2 | 18 |
| 21.9 | 19 |
| 22.6 | 13 |
| 23.3 | 16 |
| 23.8 | 12 |
| 24.1 | 14 |
| 24.6 | 15 |
| 25.6 | 13 |
| 26.0 | 15 |
| 26.8 | 11 |
| 28.4 | 10 |
| 29.0 | 9 |
| 29.5 | 9 |

Example 13

Preparation of Form F of Compound (I)

Approximate 20 mg of Form Amorphous of compound (I) as prepared in Example 7 was weighed and transferred into a mortar. 0.1 mL n-propanol was added. The mixture was grinded manually for 3 minutes.

Figure 8:
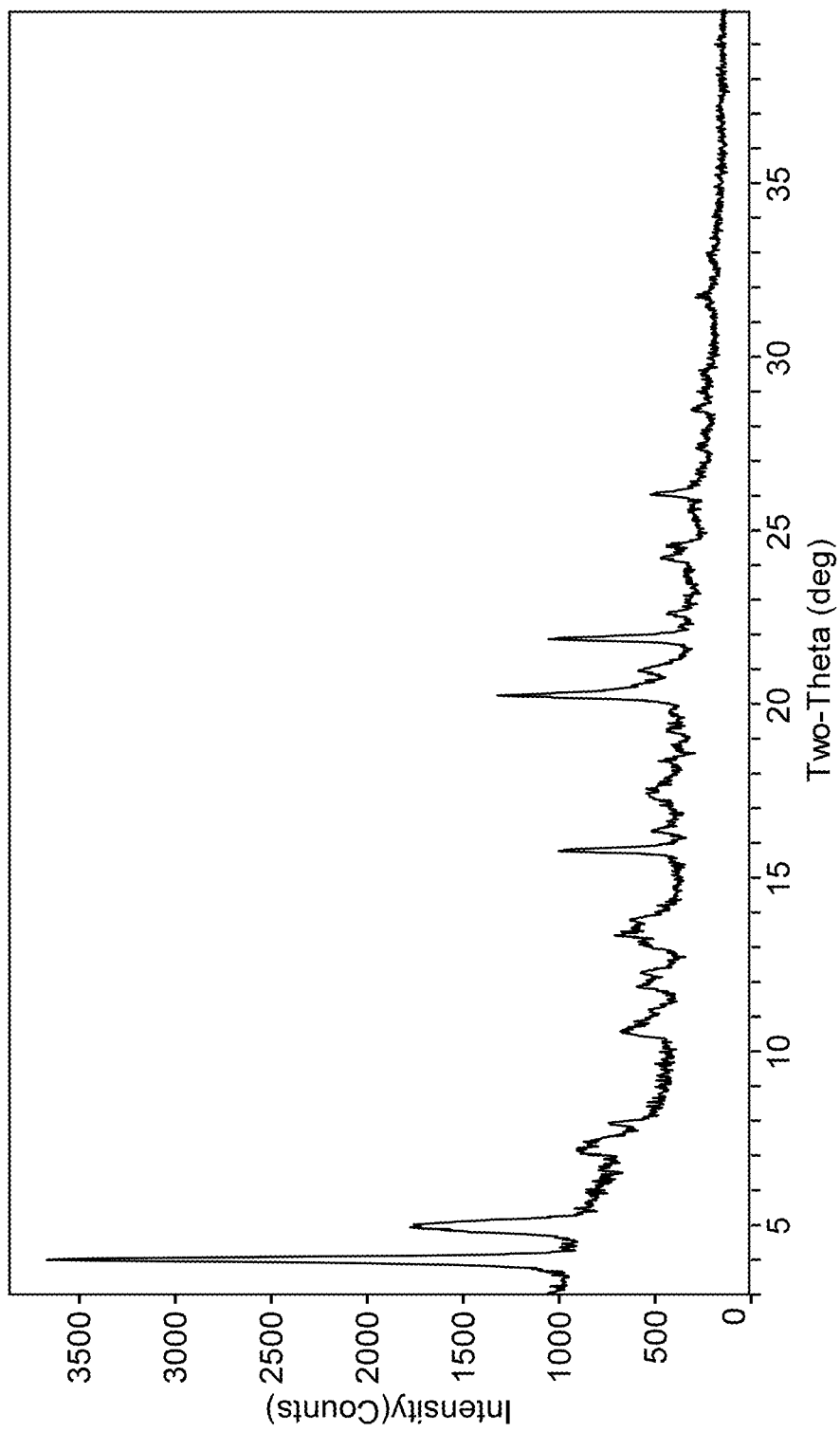

The solid was collected for XRPD analysis. The XRPD pattern of Form F of compound (I) is shown in FIG. 8. Major peaks and their related intensities in the XRPD pattern are shown in table below.

Characterization Method

XRPD: Bruker D8 Advance diffractometer X-ray powder diffractometer with Cu-Kα radiation. Tube voltage was 40 KV and tube current was 40 mA. Scan range was from 3 to 40 degree 2-theta. The step size was 0.02° at a scanning speed of 6°/min.

TABLE 8

X-ray powder diffraction peaks of Form F of compound (I)

| Pos. [°2-theta] | Rel. Int. [%] |
|---|---|
| 4.0 | 100 |
| 4.9 | 48 |
| 7.1 | 25 |
| 7.4 | 24 |
| 7.9 | 20 |
| 10.6 | 18 |
| 11.2 | 14 |
| 11.9 | 16 |
| 12.3 | 15 |
| 13.1 | 16 |
| 13.3 | 19 |
| 13.8 | 17 |
| 15.8 | 27 |
| 16.3 | 14 |
| 17.4 | 15 |
| 17.9 | 12 |
| 18.4 | 13 |
| 19.2 | 12 |
| 19.8 | 11 |
| 20.3 | 36 |
| 21.0 | 16 |
| 21.9 | 29 |
| 22.6 | 12 |
| 23.8 | 9 |
| 24.2 | 13 |
| 24.6 | 12 |
| 25.6 | 9 |
| 26.0 | 14 |
| 28.5 | 8 |
| 29.0 | 7 |
| 29.6 | 7 |
| 31.7 | 8 |
| 32.9 | 6 |

Example 14

Preparation of Form G of Compound (I)

Approximate 15 mg of Form A of compound (I) as prepared in Example 3 was weighed and transferred to a glass vial. 2 mL an ethanol/n-heptane mixture (1:1, v:v) was added and sonicated mildly to ensure complete dissolution. About 2 mg of PEG 6000 was added. The solution was evaporated to dryness at room temperature.

Figure 9:
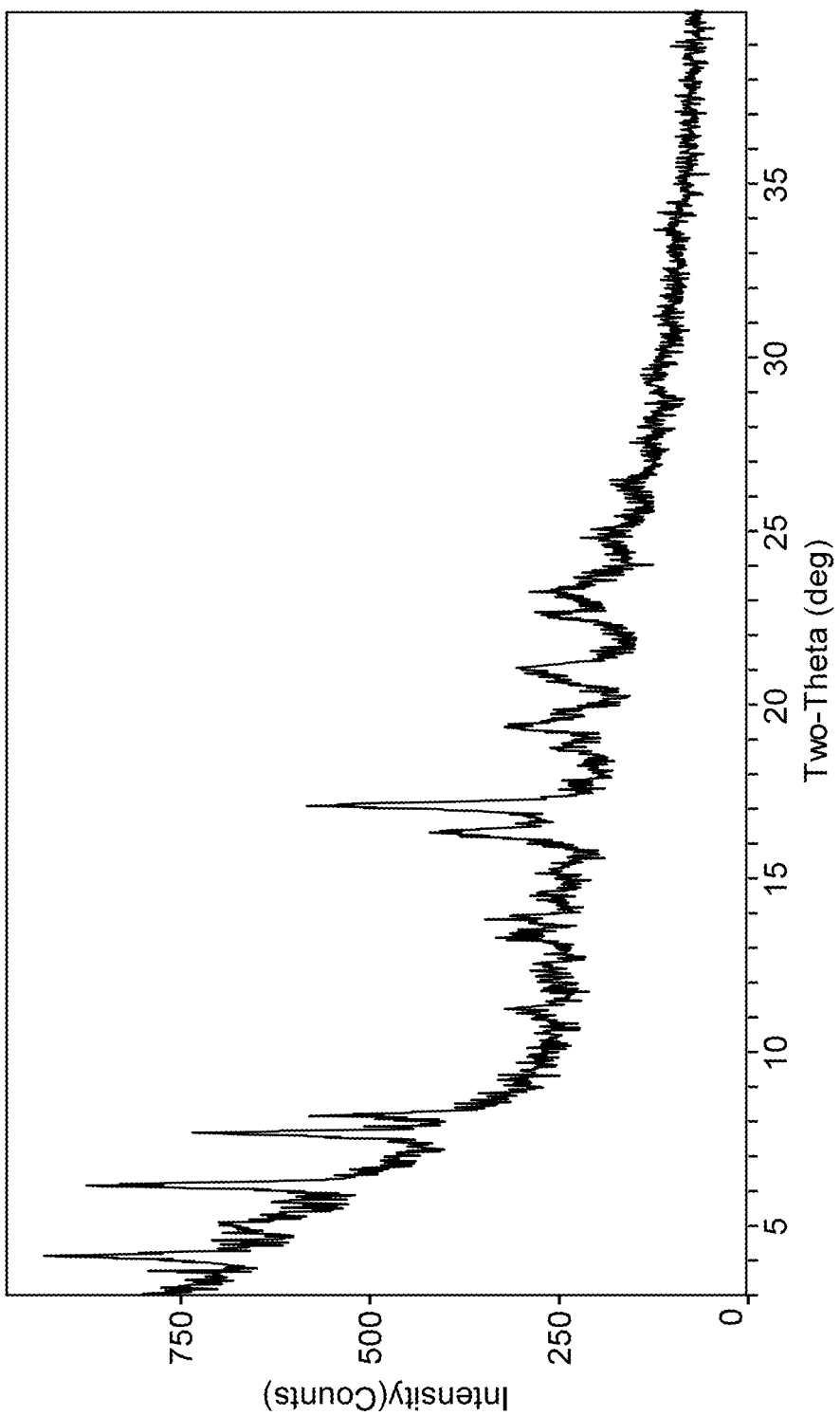

The solid was collected for XRPD analysis. The XRPD pattern of Form G of compound (I) is shown in FIG. 9. Major peaks and their related intensities in the XRPD pattern are shown in table below.

Characterization Method

XRPD: Bruker D8 Advance diffractometer X-ray powder diffractometer with Cu-Kα radiation. Tube voltage was 40 KV and tube current was 40 mA. Scan range was from 3 to 40 degree 2-theta. The step size was 0.02° at a scanning speed of 6°/min.

TABLE 9

X-ray powder diffraction peaks of Form G of compound (I).

| Pos. [°2-theta] | Rel. Int. [%] |
|---|---|
| 3.7 | 85 |
| 4.1 | 100 |
| 5.0 | 75 |
| 6.2 | 94 |
| 7.7 | 79 |
| 8.2 | 62 |
| 11.3 | 34 |
| 13.3 | 36 |
| 13.8 | 37 |
| 14.5 | 31 |
| 16.3 | 45 |

TABLE 9-continued

X-ray powder diffraction peaks of Form G of compound (I).

| Pos. [°2-theta] | Rel. Int. [%] |
|---|---|
| 17.1 | 63 |
| 18.8 | 28 |
| 19.3 | 34 |
| 19.9 | 27 |
| 20.8 | 30 |
| 21.1 | 33 |
| 22.7 | 30 |
| 23.3 | 31 |
| 23.8 | 23 |
| 24.8 | 24 |
| 25.1 | 22 |
| 26.5 | 19 |
| 29.4 | 15 |

Example 15

Preparation of Sodium Salt Form J of Compound (I)

1.0 g of Form A of compound (I) as prepared in Example 3 was weighed into a vial and dissolved in 13 mL ethanol. The solution was stirred for 5 min under a 40° C. water bath. 73.19 mg of sodium hydroxide (1.1 eq.) was added into the solution and stirring was applied for 1 min. The solution became clear, then turned cloudy, and then became jell-like. 2.0 mL ethanol was added and the mixture was agitated at RT until the solution became flowable. After being agitated at RT for 5 h, the product was isolated by vacuum filtration. The wet cake was washed using a small amount of ethanol and dried at 40° C. in an air-blow oven for 16 h.

Figure 10:
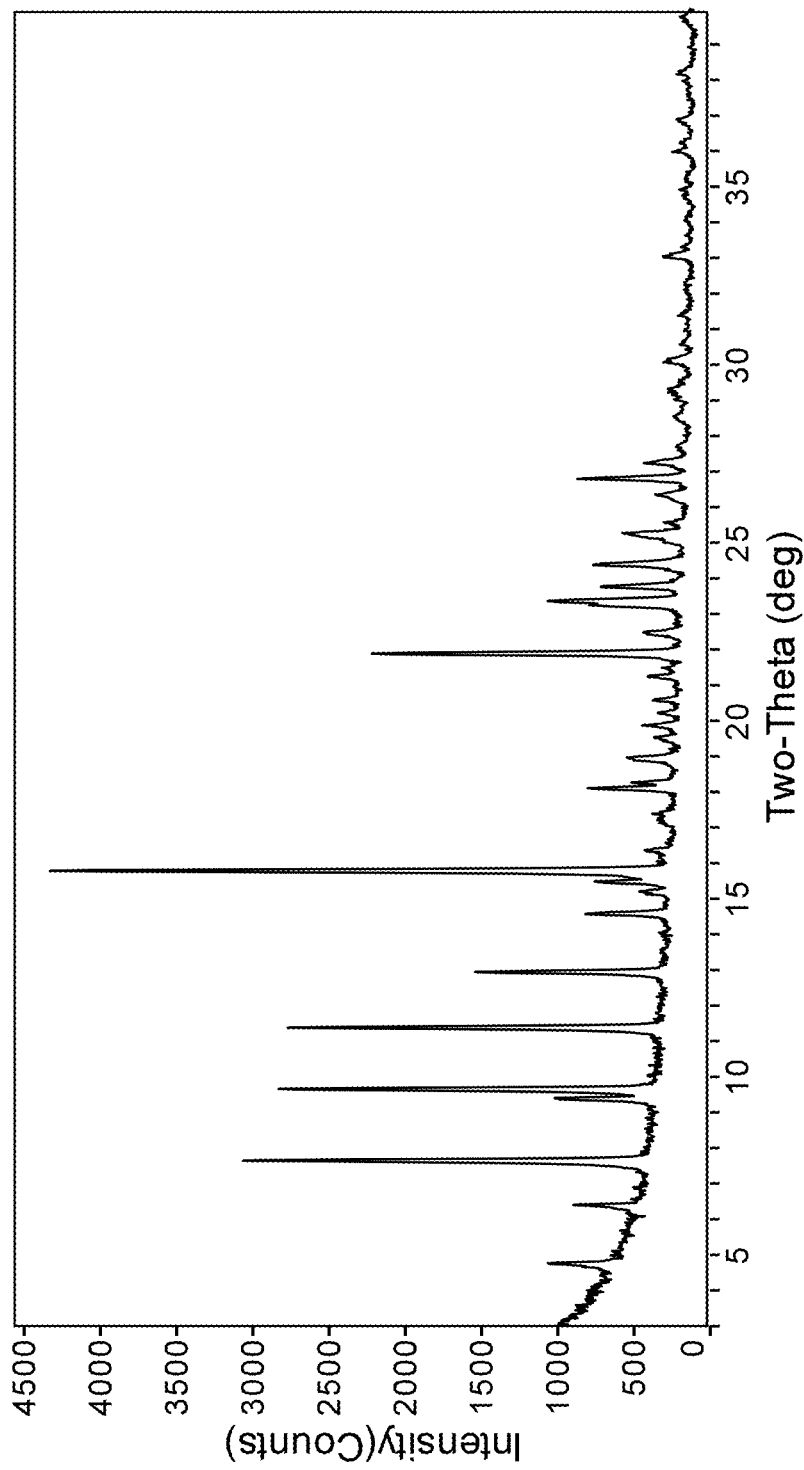

The solid was collected for XRPD analysis. The XRPD pattern of sodium salt Form J of compound (I) is shown in FIG. 10. Major peaks and their related intensities in the XRPD pattern are shown in table below.

Experimental Conditions

XRPD: PANalytical EMPYREAN X-ray powder diffractometer with Cu-Kα radiation. Tube voltage was 40 KV and tube current was 40 mA. Scan range was from 4 to 40 degree 2-theta. The step size was 0.053° at a scanning speed of 10.504°/min.

TABLE 10

X-ray powder diffraction peaks of
sodium salt form J of compound (I).

| Pos. [°2-theta] | Rel. Int. [%] |
|---|---|
| 4.8 | 6 |
| 6.5 | 7 |
| 7.7 | 37 |
| 9.4 | 8 |
| 9.7 | 29 |
| 11.5 | 24 |
| 13.0 | 18 |
| 14.7 | 50 |
| 15.3 | 16 |
| 15.9 | 100 |
| 16.5 | 14 |
| 17.5 | 6 |
| 18.2 | 6 |
| 19.0 | 17 |
| 19.6 | 5 |
| 20.0 | 10 |
| 20.3 | 7 |
| 20.7 | 7 |
| 21.3 | 10 |
| 22.0 | 32 |
| 22.6 | 11 |

TABLE 10-continued

X-ray powder diffraction peaks of
sodium salt form J of compound (I).

| Pos. [°2-theta] | Rel. Int. [%] |
|---|---|
| 23.4 | 28 |
| 23.9 | 24 |
| 24.5 | 20 |
| 25.3 | 14 |
| 26.4 | 7 |
| 26.9 | 9 |
| 27.3 | 6 |
| 27.7 | 2 |
| 28.6 | 2 |
| 29.4 | 5 |
| 30.2 | 6 |
| 30.7 | 1 |
| 31.5 | 2 |
| 32.3 | 1 |
| 33.2 | 3 |
| 34.2 | 2 |
| 34.7 | 1 |
| 35.5 | 1 |
| 36.1 | 3 |
| 37.0 | 3 |
| 38.3 | 3 |
| 39.1 | 1 |

Figure 11:
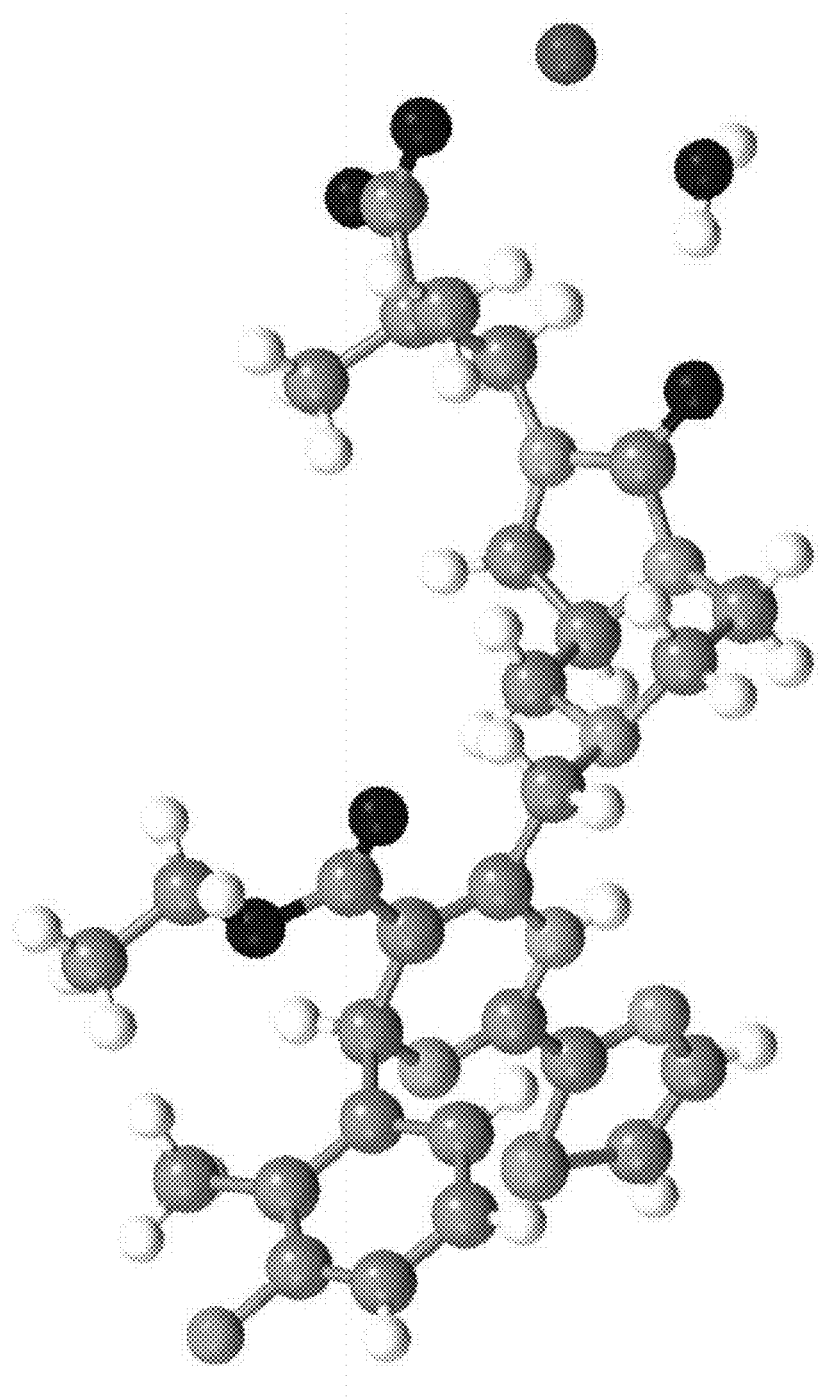

FIG. 11 shows the X-ray structure of sodium salt Form J. The single crystal X-ray intensity data were collected at 293(2) K using a Bruker SMART APEX II with Mo-K-alpha-radiation (0.71 Å). Structure solution and refinement was performed using the ShelXTL software (Bruker AXS, Karlsruhe). The crystal data and structure refinement is shown in Table 11.

TABLE 11

Single crystal structural data of sodium salt Form J

| Crystal form | Sodium salt Form J |
|---|---|
| Solid form description | Hydrate |
| Measuring Temperature | 293(2)K |
| Crystal system | orthorhombic |
| Space group | P $2_1 2_1 2_1$ |
| Unit cell dimensions | |
| a= | 6.0795(6) Å |
| b= | 14.5770(13) Å |
| c= | 36.065(3) Å |
| α= | 90° |
| β= | 90° |
| γ= | 90° |
| Cell volume | 3196.1(5) Å$^3$ |
| API molecules in unit cell | 4 |
| Calculated density | 1.327 g/cm$^3$ |

Example 16

Preparation of Form H of Compound (I)

200 mg of sodium salt Form J of compound (I) as prepared in Example 15 was weighed into a vial, to which 20 mL FaSSIF solution was added to form a suspension. The obtained suspension was agitated at 25° C. for 16 h. Then, the solid was collected by filtration and dried at 40° C. under air blowing for 16 h. The solid was collected for XRPD analysis, DSC analysis and TGA analysis.

Figure 12:
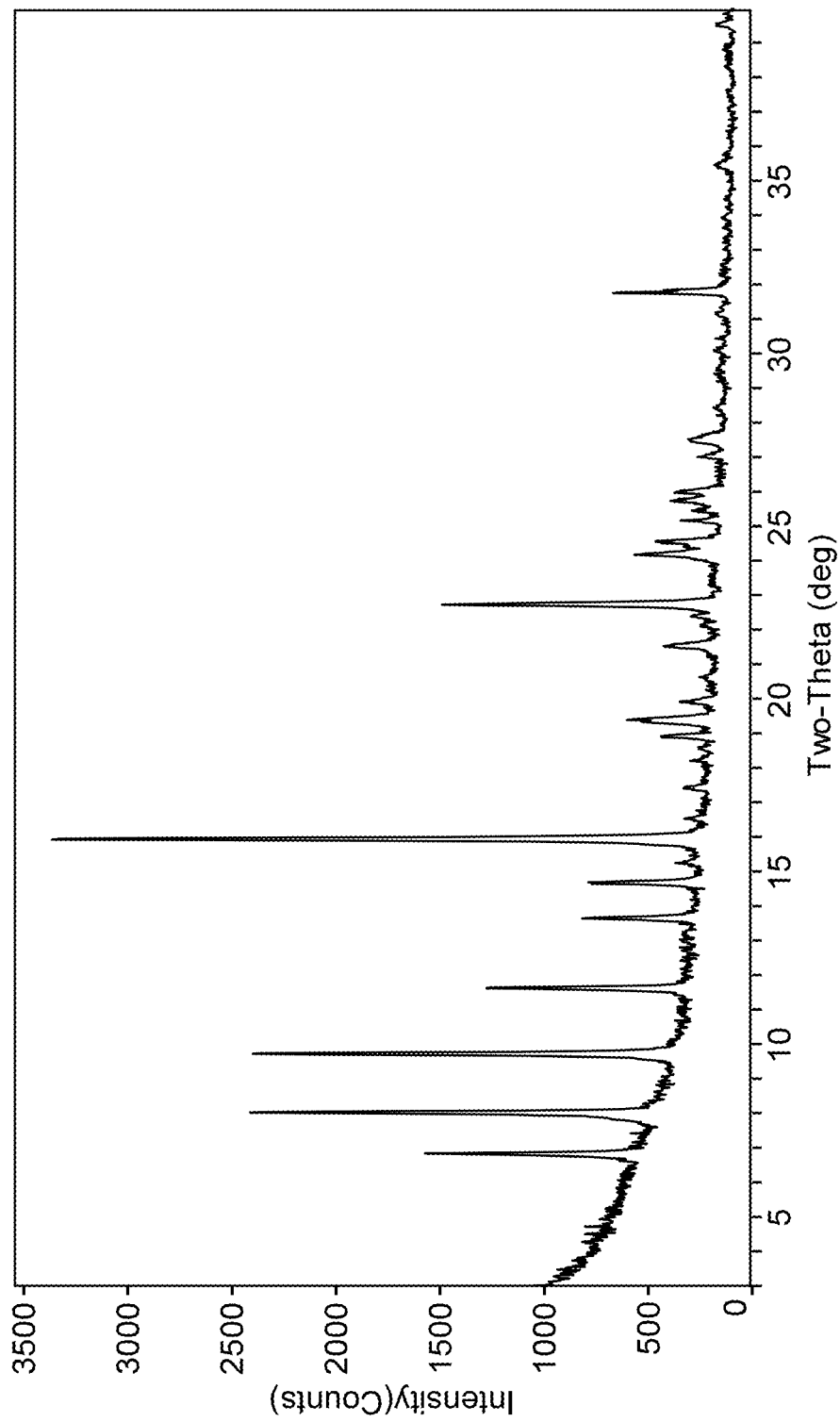

The XRPD pattern of Form H of compound (I) is shown in FIG. 12. Major peaks and their related intensities in the XRPD pattern are shown in table below.

Characterization Method

XRPD: PANalytical EMPYREAN X-ray powder diffractometer with Cu-Kα radiation. Tube voltage was 40 KV and tube current was 40 mA. Scan range was from 4 to 40 degree 2-theta. The step size was 0.026° at a scanning speed of 3.348°/min.

DSC analysis: TA Q2000, 25-250° C., heating rate 10° C./min.

TGA analysis: TA Q5000, 25-300° C., heating rate 10° C./min.

TABLE 12

X-ray powder diffraction peaks of Form H of compound (I).

| Pos. [°2-theta] | Rel. Int. [%] |
|---|---|
| 6.8 | 27 |
| 8.0 | 46 |
| 9.7 | 34 |
| 11.6 | 20 |
| 13.6 | 11 |
| 14.6 | 67 |
| 15.2 | 19 |
| 15.7 | 33 |
| 15.9 | 100 |
| 16.5 | 11 |
| 17.4 | 14 |
| 18.2 | 1 |
| 18.5 | 5 |
| 18.9 | 29 |
| 19.3 | 14 |
| 19.4 | 8 |
| 19.9 | 17 |
| 20.6 | 6 |
| 21.5 | 14 |
| 22.3 | 9 |
| 22.7 | 28 |
| 23.5 | 1 |
| 24.1 | 39 |
| 24.5 | 29 |
| 25.1 | 13 |
| 25.7 | 8 |
| 26.0 | 18 |
| 26.3 | 1 |
| 27.0 | 8 |
| 27.5 | 10 |
| 28.4 | 2 |
| 29.1 | 2 |
| 29.5 | 6 |
| 29.9 | 3 |
| 30.2 | 4 |
| 30.4 | 1 |
| 31.1 | 6 |
| 31.4 | 3 |
| 32.0 | 2 |
| 32.2 | 2 |
| 32.7 | 1 |
| 33.0 | 1 |
| 33.3 | 1 |
| 33.9 | 1 |
| 34.2 | 1 |
| 34.5 | 1 |
| 35.3 | 3 |
| 35.8 | 3 |
| 36.4 | 1 |
| 37.5 | 1 |

Figure 13:
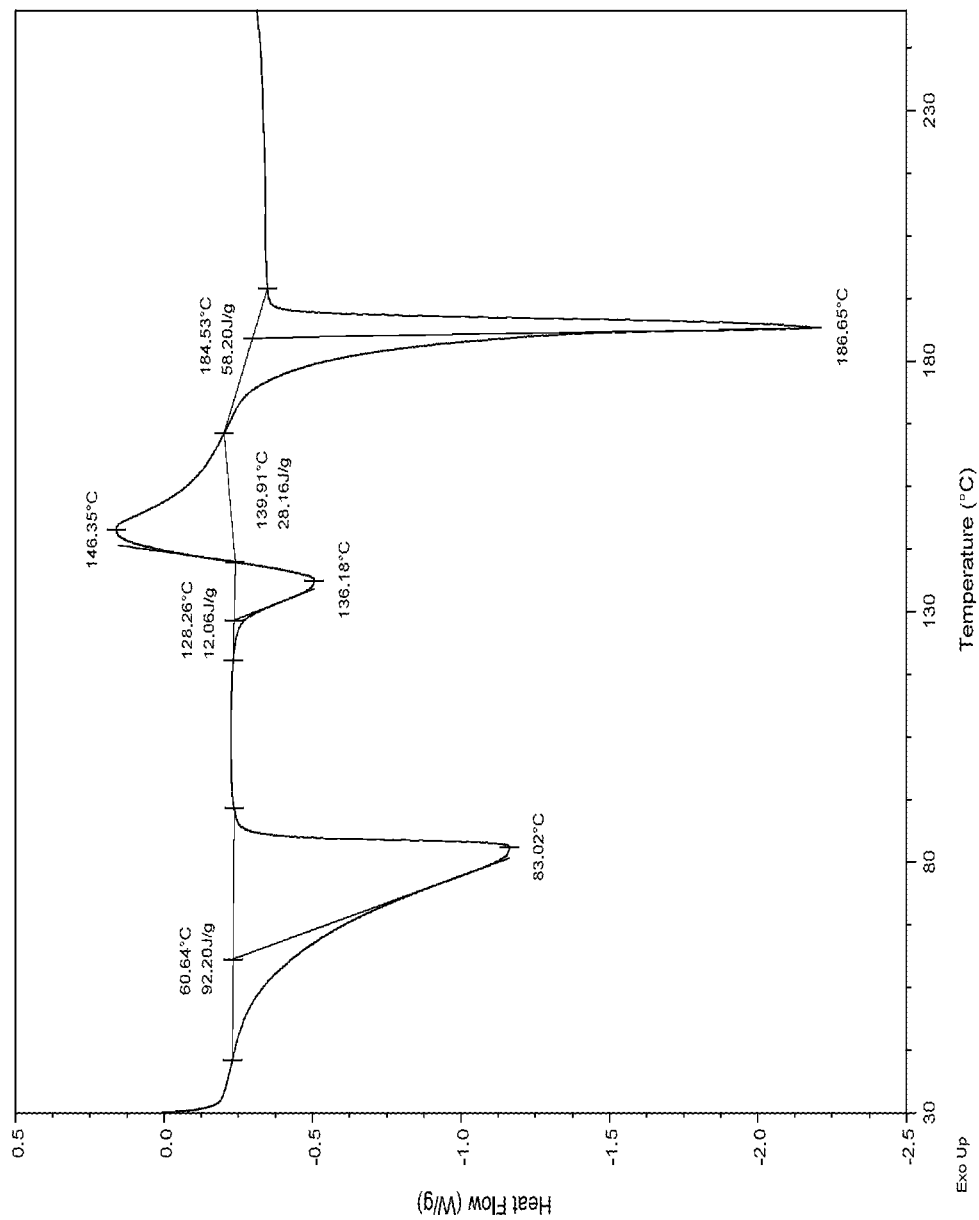
Figure 14:
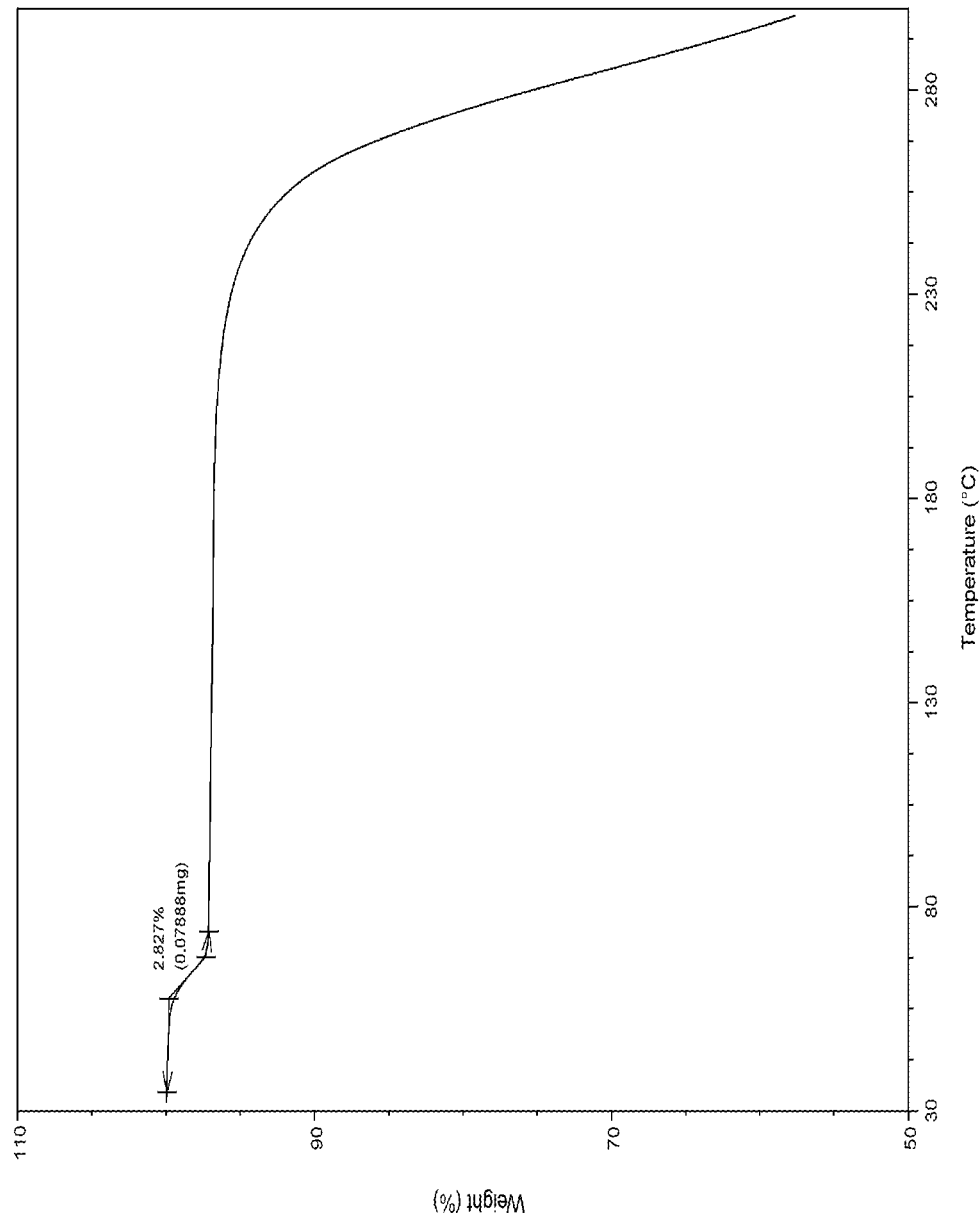

DSC and TGA results shown in FIG. 13. and FIG. 14. indicate Form H of compound (I) has a dehydration temperature at around 60° C.

Example 17

Preparation of Form I of Compound (I)

10 mg of Form H of compound (I) as prepared in Example 16 was weighed into a variable temperature chamber. The sample was placed at 60° C. for 5 min.

Figure 15:
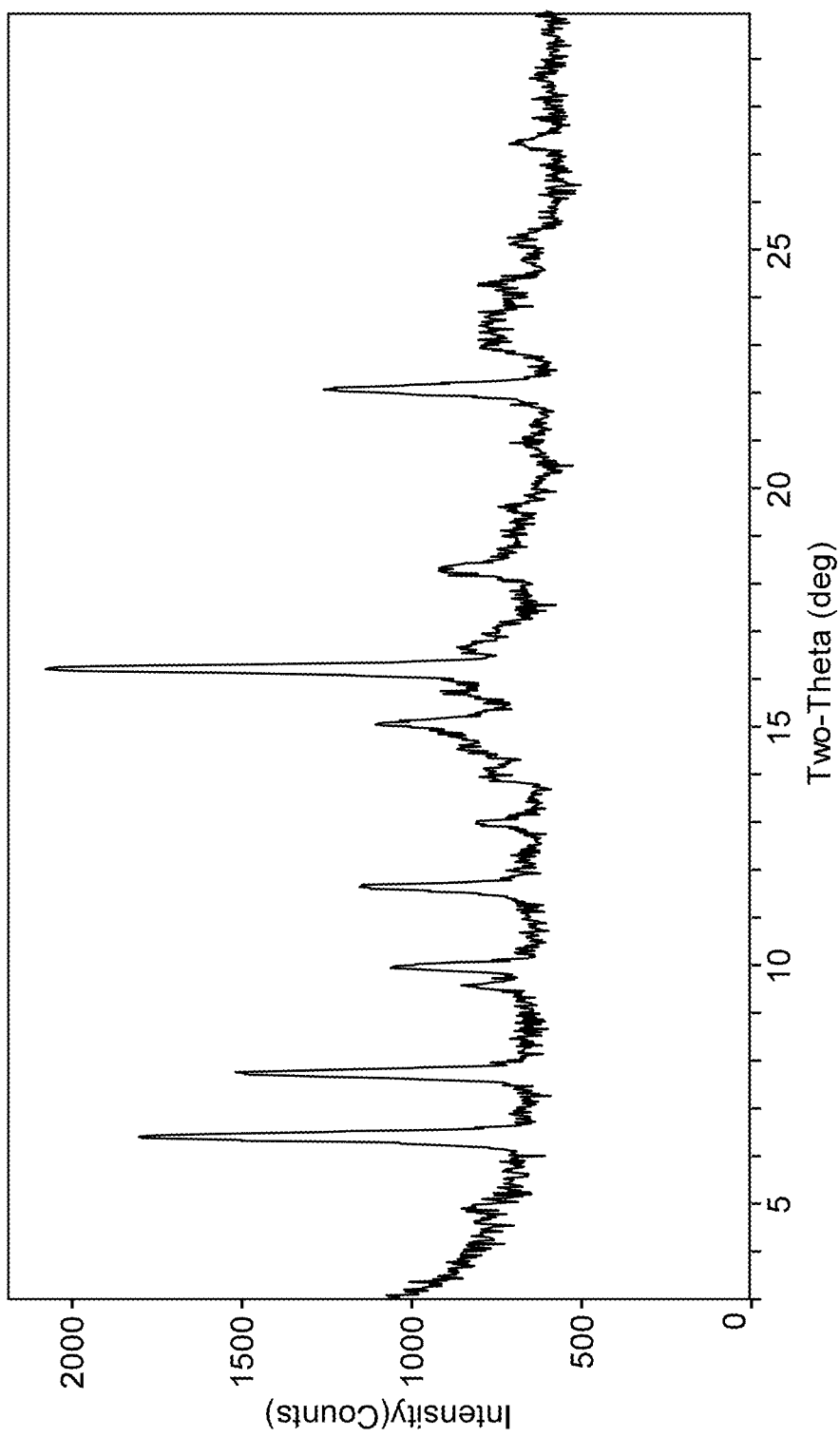

The solid was collected for XRPD analysis. The XRPD pattern of Form I of compound (I) is shown in FIG. 15. Major peaks and their related intensities in the XRPD pattern are shown in table below.

Characterization Method

XRPD: Bruker D8 Advance diffractometer X-ray powder diffractometer with Cu-Kα radiation. Tube voltage was 40 KV and tube current was 40 mA. Scan range was from 3 to 30 degree 2-theta. The step size was 0.02° at a scanning speed of 6°/min.

TABLE 13

X-ray powder diffraction peaks of Form I of compound (I).

| Pos. [°2-theta] | Rel. Int. [%] |
|---|---|
| 6.4 | 84 |
| 7.8 | 65 |
| 9.6 | 16 |
| 9.9 | 31 |
| 11.6 | 39 |
| 13.0 | 13 |
| 13.9 | 10 |
| 14.5 | 13 |
| 15.0 | 27 |
| 15.7 | 11 |
| 16.2 | 100 |
| 16.7 | 8 |
| 18.3 | 19 |
| 19.6 | 6 |
| 20.9 | 8 |
| 22.1 | 48 |
| 23.0 | 12 |
| 24.3 | 11 |
| 25.3 | 9 |
| 27.2 | 11 |

Example 18

Preparation of Hydrochloride Salt Form K of Compound (I)

400 mg of Form A of compound (I) as prepared in Example 3 and 9.0 mL acetone was added into a vial in a 45° C. water bath, and the mixture was stirred to afford a clear solution. 74.4 mg concentrated hydrochloric acid (1.1 eq.) in 1.0 mL acetone was added to the solution and the solution instantly became cloudy. After being agitated at RT for 1 h, the mixture became sticky and solidified. After addition of 2.0 mL acetone, the mixture became flowable. The suspension was agitated for another 5 h at RT, the solid was collected by vacuum filtration, washed with a small amount of acetone, and dried at 40° C. in an air-blow oven for 16 h. The solid was collected for XRPD analysis.

Figure 16:
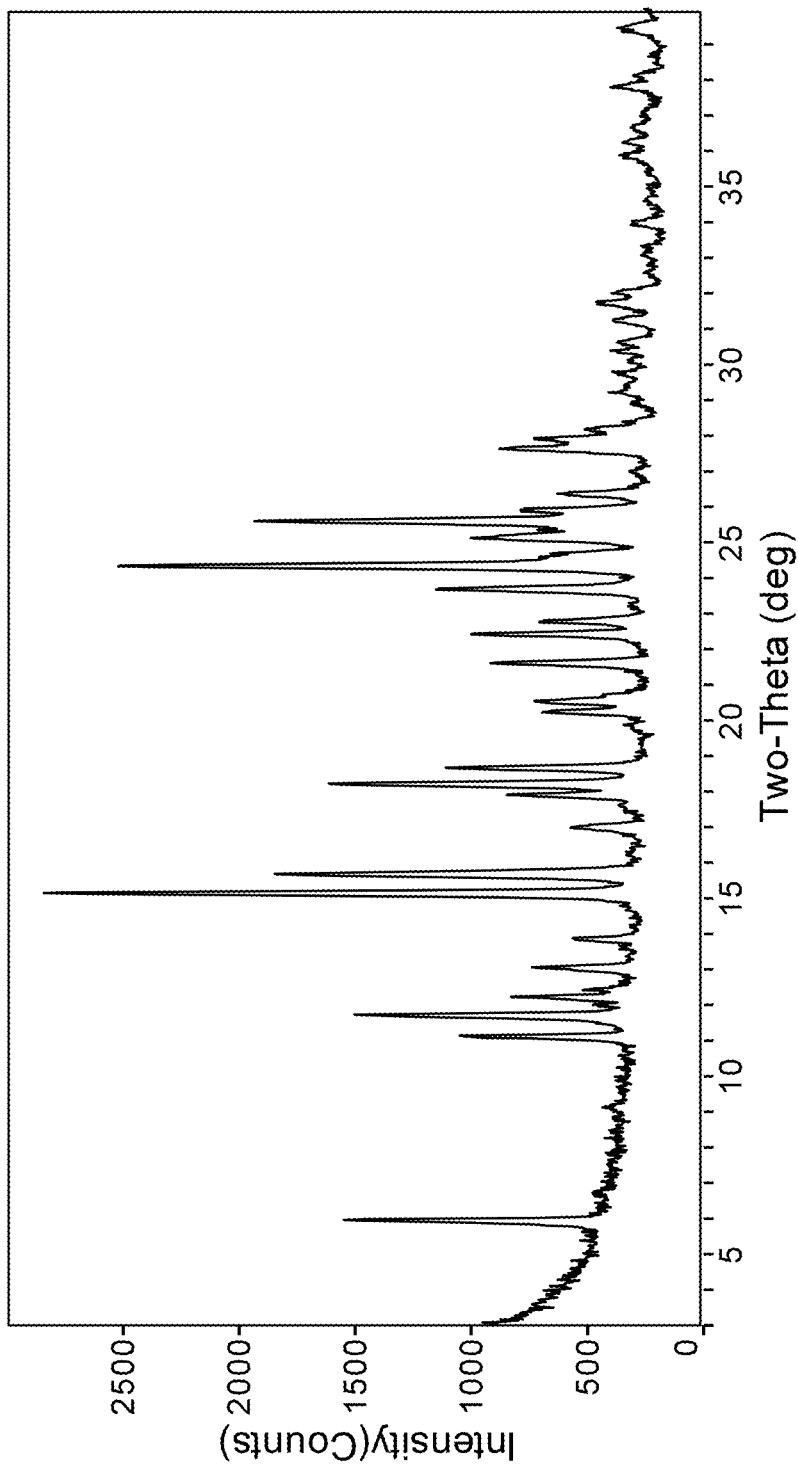

The XRPD pattern of hydrochloride salt Form K of compound (I) is shown in FIG. 16. Major peaks and their related intensities in the XRPD pattern are shown in table below.

Experimental Conditions

XRPD: PANalytical EMPYREAN X-ray powder diffractometer with Cu-Kα radiation. Tube voltage was 40 KV and tube current was 40 mA. Scan range was from 4 to 40 degree 2-theta. The step size was 0.026° at a scanning speed of 3.348°/min.

TABLE 14

X-ray powder diffraction peaks of hydrochloride salt Form K of compound(I).

| Pos. [°2-theta] | Rel. Int. [%] |
|---|---|
| 5.4 | 100 |
| 5.8 | 6 |
| 6.9 | 8 |
| 7.9 | 1 |

TABLE 14-continued

X-ray powder diffraction peaks of hydrochloride salt Form K of compound(I).

| Pos. [°2-theta] | Rel. Int. [%] |
|---|---|
| 9.6 | 9 |
| 10.9 | 3 |
| 11.7 | 3 |
| 12.0 | 1 |
| 12.5 | 9 |
| 13.3 | 46 |
| 13.8 | 25 |
| 14.8 | 32 |
| 15.9 | 48 |
| 16.3 | 55 |
| 16.5 | 14 |
| 18.0 | 48 |
| 18.8 | 1 |
| 18.9 | 1 |
| 19.3 | 9 |
| 19.5 | 19 |
| 20.0 | 15 |
| 20.6 | 2 |
| 20.9 | 6 |
| 21.4 | 2 |
| 21.7 | 24 |
| 22.1 | 1 |
| 22.4 | 15 |
| 22.7 | 40 |
| 23.4 | 26 |
| 23.6 | 7 |
| 23.8 | 9 |
| 24.1 | 15 |
| 24.7 | 2 |
| 25.4 | 9 |
| 25.6 | 6 |
| 26.1 | 4 |
| 26.7 | 5 |
| 27.3 | 1 |
| 27.8 | 10 |
| 28.0 | 15 |
| 29.6 | 7 |
| 30.3 | 2 |
| 31.3 | 1 |
| 31.8 | 2 |
| 32.9 | 3 |
| 34.1 | 2 |
| 34.8 | 4 |
| 35.3 | 2 |
| 35.7 | 2 |
| 35.9 | 2 |

TABLE 15

X-ray powder diffraction peaks of hydrochloride salt Form L of compound(I).

| Pos. [°2-theta] | Rel. Int. [%] |
|---|---|
| 6.0 | 94 |
| 11.2 | 45 |
| 11.5 | 1 |
| 11.8 | 56 |
| 12.1 | 7 |
| 12.3 | 22 |
| 12.5 | 8 |
| 13.1 | 24 |
| 14.0 | 10 |
| 15.3 | 100 |
| 15.8 | 58 |
| 17.1 | 12 |
| 17.7 | 3 |
| 18.0 | 16 |
| 18.3 | 56 |
| 18.7 | 29 |
| 20.4 | 15 |
| 20.6 | 14 |
| 21.7 | 22 |
| 22.5 | 29 |
| 22.9 | 14 |
| 23.8 | 31 |
| 24.4 | 66 |
| 24.8 | 10 |
| 25.2 | 19 |
| 25.7 | 41 |
| 26.0 | 14 |
| 26.5 | 9 |
| 27.1 | 1 |
| 27.7 | 21 |
| 28.0 | 11 |
| 28.3 | 7 |
| 29.3 | 4 |
| 29.8 | 4 |
| 30.5 | 4 |
| 30.8 | 4 |
| 31.3 | 5 |
| 31.8 | 6 |
| 32.1 | 6 |
| 32.7 | 1 |
| 33.1 | 2 |
| 34.0 | 4 |
| 34.7 | 2 |
| 35.9 | 4 |
| 36.3 | 4 |
| 36.8 | 4 |
| 37.2 | 2 |
| 37.8 | 7 |
| 38.2 | 3 |
| 38.8 | 1 |

Example 19

Preparation of Hydrochloride Salt Form L of Compound (I)

150 mg of hydrochloride salt Form K of compound (I) as prepared in Example 18 was placed in a high relative humidity chamber closed to 100% RH at ambient temperature for 3 days.

Figure 17:
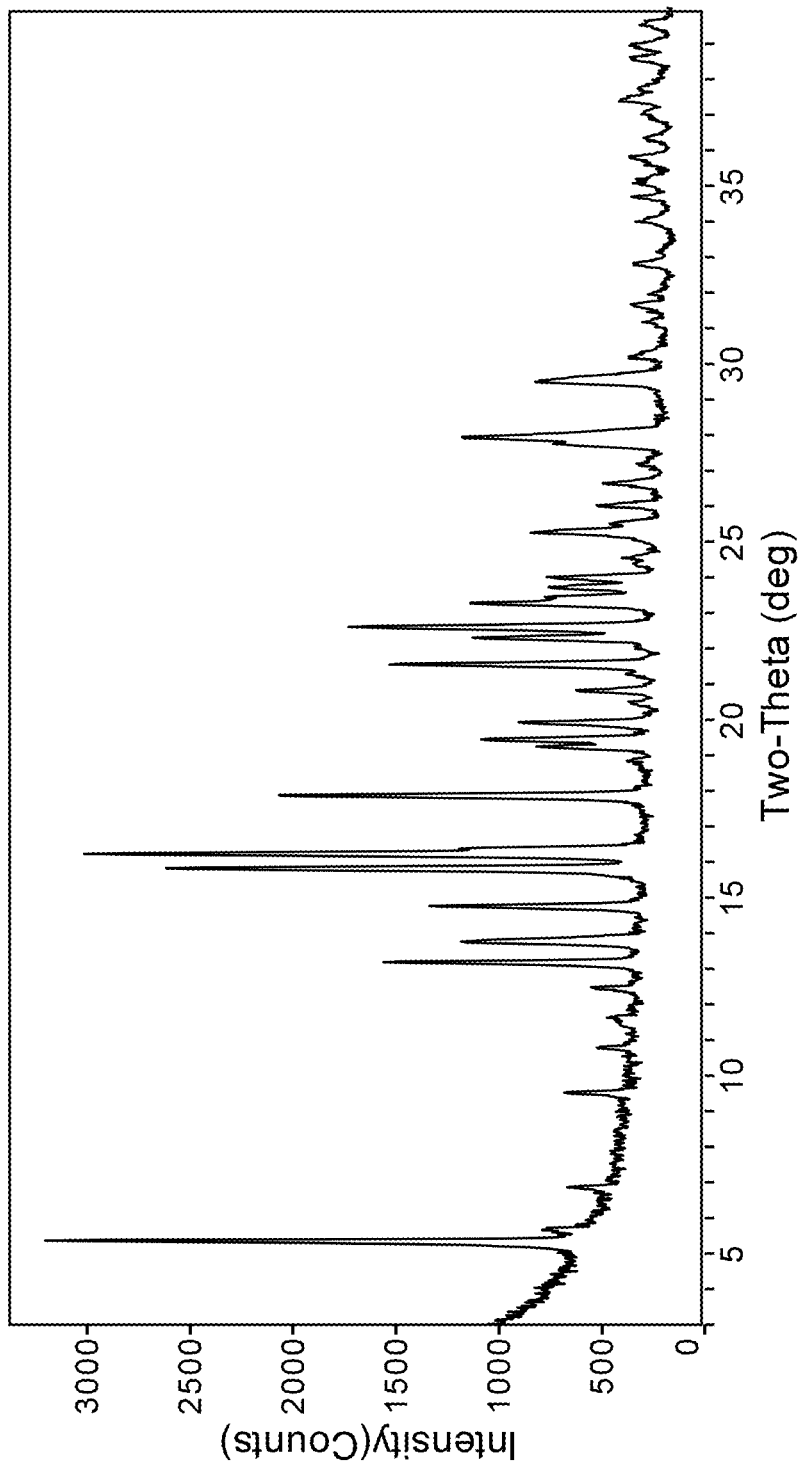

The solid was collected for XRPD analysis. The XRPD pattern of hydrochloride salt Form L of compound (I) is shown in FIG. 17. Major peaks and their related intensities in the XRPD pattern are shown in table below.

Experimental Method

XRPD: PANalytical EMPYREAN X-ray powder diffractometer with Cu-Kα radiation. Tube voltage was 40 KV and tube current was 40 mA. Scan range was from 4 to 40 degree 2-theta. The step size was 0.026° at a scanning speed of 3.348°/min.

Figure 18:
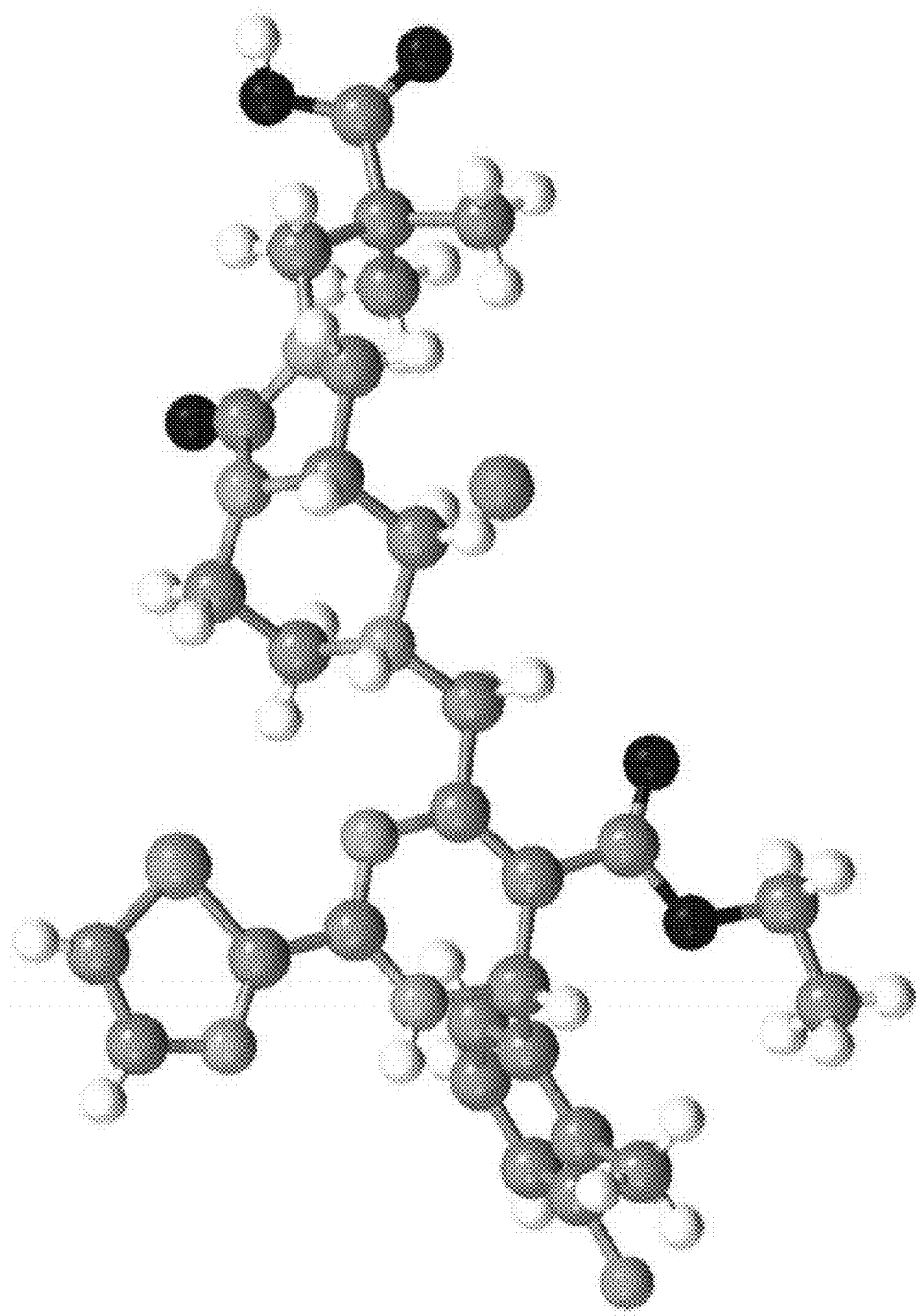

FIG. 18 shows the X-ray structure of hydrochloride salt Form L. The single crystal X-ray intensity data were collected at 100.08 K using a Gemini with Mo-K-alpha-radiation (0.71 Å). Structure solution and refinement was performed using the Olex2 software. The crystal data and structure refinement is shown in Table 16.

TABLE 16

Single crystal structural data of hydrochloride salt Form L

| Crystal form | Hydrochloride salt Form L |
|---|---|
| Solid form description | Hydrate |
| Measuring Temperature | 100.08K |
| Crystal system | triclinic |
| Space group | P 1 |
| Unit cell dimensions | 10.0621(3) Å |
| a= | |
| b= | 11.9420(5) Å |
| c= | 15.6269(5) Å |
| α= | 103.562(3)° |

TABLE 16-continued

Single crystal structural data of hydrochloride salt Form L

| | |
|---|---|
| β= | 105.711(3)° |
| γ= | 93.148(3)° |
| Cell volume | 1743.06(11) Å$^3$ |
| API molecules in unit cell | 2 |
| Calculated density | 1.356 g/cm$^3$ |

Example 20

Preparation of Sulfate Salt Form M of Compound (I)

9.98 mg of Form A of compound (I) as prepared in Example 3 was added into 1.5 mL IPA, and 1.8 mg of sulfuric acid (1.1 eq.) was added to obtain a clear solution. The solvent was evaporated to 0.2 mL and remaining was agitated for another 16 h, resulting in a suspension. The solid was collected by centrifugation and dried at 40° C. in a vacuum oven for 16 h.

Figure 19:
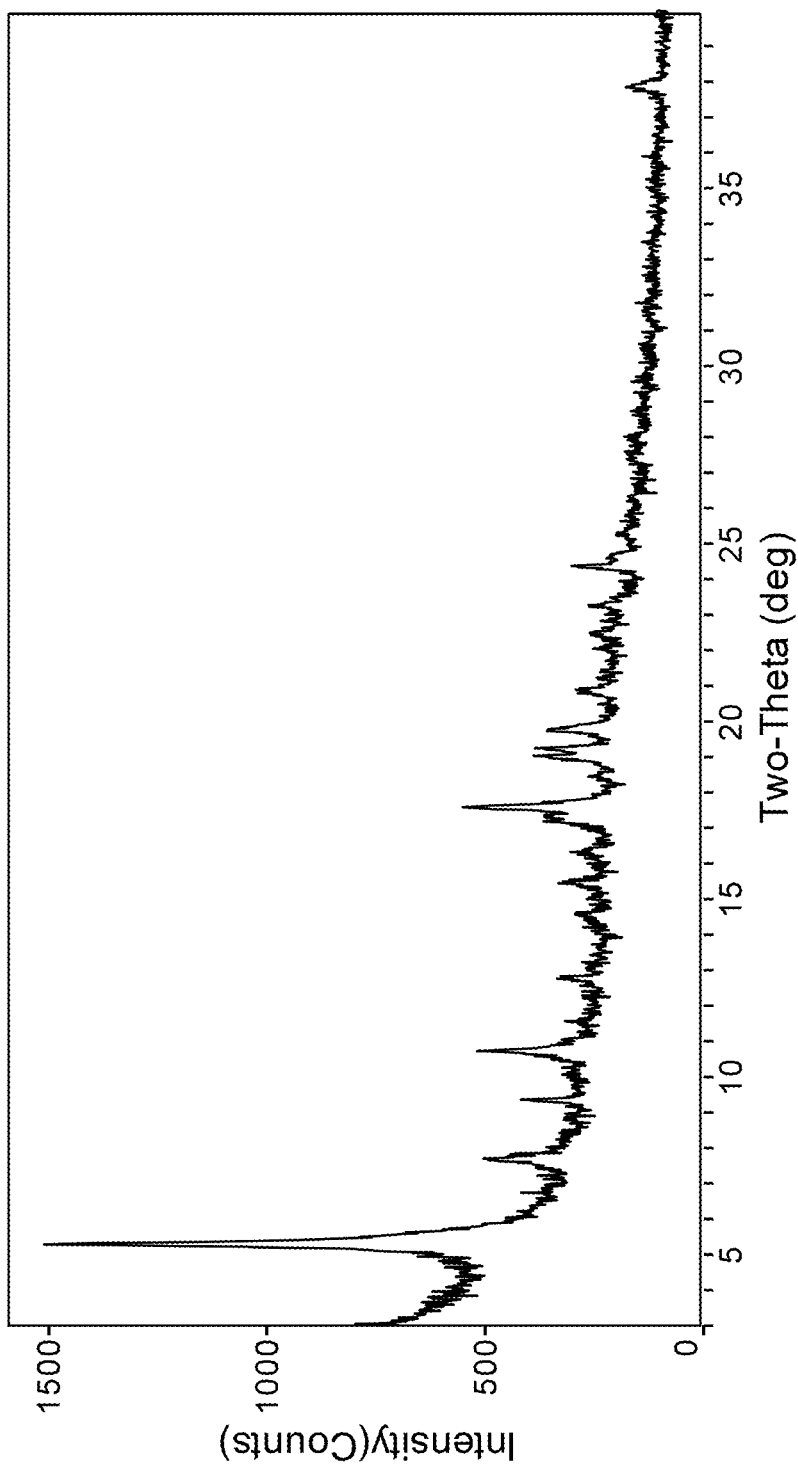

The solid was collected for XRPD analysis. The XRPD pattern of sulfate Form M of compound (I) is shown in FIG. 19. Major peaks and their related intensities in the XRPD pattern are shown in table below.

Characterization Method

XRPD: Bruker D8 Advance diffractometer X-ray powder diffractometer with Cu-Kα radiation. Tube voltage was 40 KV and tube current was 40 mA. Scan range was from 3 to 40 degree 2-theta. The step size was 0.02° at a scanning speed of 6°/min.

TABLE 17

X-ray powder diffraction peaks of sulfate Form M of compound (I).

| Pos. [°2-theta] | Rel. Int. [%] |
|---|---|
| 5.3 | 100 |
| 7.7 | 18 |
| 9.4 | 12 |
| 10.7 | 23 |
| 12.8 | 9 |
| 14.6 | 7 |
| 15.5 | 10 |
| 16.3 | 7 |
| 17.2 | 14 |
| 17.6 | 32 |
| 19.0 | 17 |
| 19.2 | 17 |
| 19.8 | 13 |
| 20.9 | 8 |
| 22.1 | 5 |
| 22.5 | 6 |
| 23.3 | 8 |
| 24.4 | 14 |
| 24.7 | 5 |
| 29.6 | 4 |
| 35.9 | 4 |
| 37.8 | 8 |

Example 21

Preparation of Sulfate Salt Form N of Compound (I)

401 mg of Form A of compound (I) as prepared in Example 3 and 8.0 mL IPA were added into a vial and heated to 60° C. in a water bath. The solution became clear after agitation, then was cooled to RT and became slightly cloudy. 76.6 mg of sulfuric acid (about 1.1 eq.) diluted in 1.0 mL IPA was added, resulting in a clear solution. The solution was agitated for 0.5 h at RT and then for 16 h at 10° C., no precipitation occurred. The solvent was evaporated to 2-3 mL, which was agitated at 10° C. The solution became very cloudy within 2 min and continuous agitation at 10° C. resulted in suspension (which turned to oil after exposure to air). After 5.0 mL IPE was added drop-wise at 10° C., the mixture was heated to RT and agitated for 16 h. The solid was isolated by vacuum filtration, and air-dried at RT. 200 mg of resulted solid was added into 1.0 mL EtOAc, which was agitated for 24 h at RT. Solid was collected by filtration, washed with a small amount of EtOAc, and dried at 40° C. in an air-blow oven for 24 hours.

Figure 20:
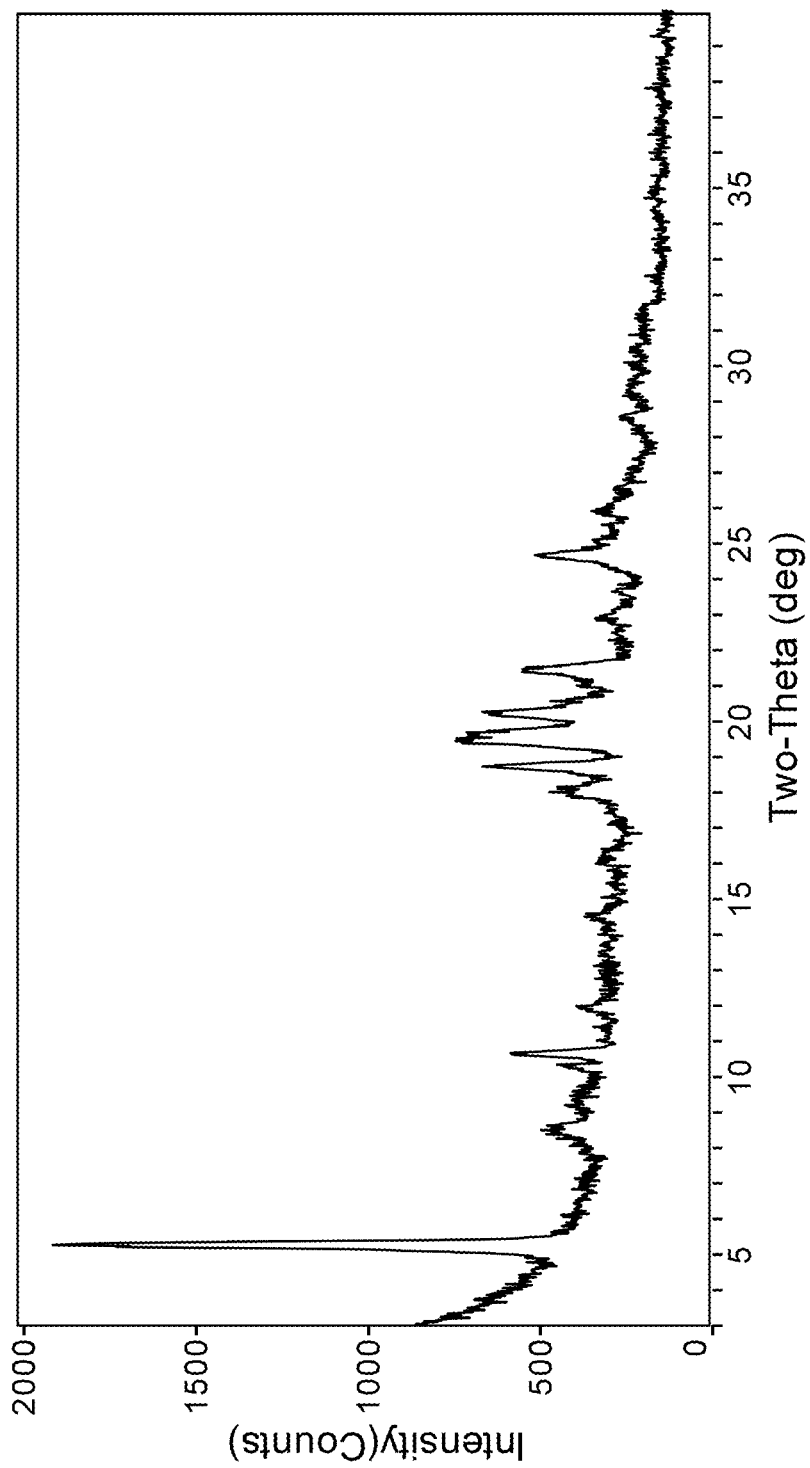

The solid was collected for XRPD analysis. The XRPD pattern of sulfate Form N of compound (I) is shown in FIG. 20. Major peaks and their related intensities in the XRPD pattern are shown in table below.

Characterization Method

XRPD: Bruker D8 Advance diffractometer X-ray powder diffractometer with Cu-Kα radiation. Tube voltage was 40 KV and tube current was 40 mA. Scan range was from 3 to 40 degree 2-theta. The step size was 0.02° at a scanning speed of 6°/min.

TABLE 18

X-ray powder diffraction peaks of sulfate Form N of compound (I).

| Pos. [°2-theta] | Rel. Int. [%] |
|---|---|
| 5.3 | 100 |
| 8.5 | 10 |
| 9.2 | 5 |
| 10.3 | 9 |
| 10.7 | 19 |
| 12.0 | 7 |
| 14.5 | 6 |
| 18.0 | 13 |
| 18.7 | 24 |
| 19.4 | 27 |
| 20.3 | 19 |
| 21.0 | 5 |
| 21.5 | 18 |
| 22.9 | 7 |
| 23.7 | 4 |
| 24.7 | 19 |
| 25.1 | 6 |
| 25.9 | 6 |
| 28.6 | 5 |
| 29.2 | 4 |
| 29.3 | 3 |
| 30.1 | 4 |
| 36.0 | 3 |
| 37.8 | 4 |

Example 22

Preparation of Besylate Salt Form O of Compound (I)

401 mg of Form A of compound (I) as prepared in Example 3 and 12.0 mL ethyl acetate was added into a vial at 65° C., and agitated until the solution became clear. The solution was cooled to RT and it turned slightly cloudy. 122.64 mg benzensulfonic acid (1.2 eq.) in 0.5 mL IPA was added to the solution, which turned clear again. The solution was stirred for 0.5 hour at RT then 16 hours at 10° C., precipitations occurred. The suspension was kept stirring at RT for 3 days. Creamy solids were collected by filtration, and were dried at RT.

Figure 21:
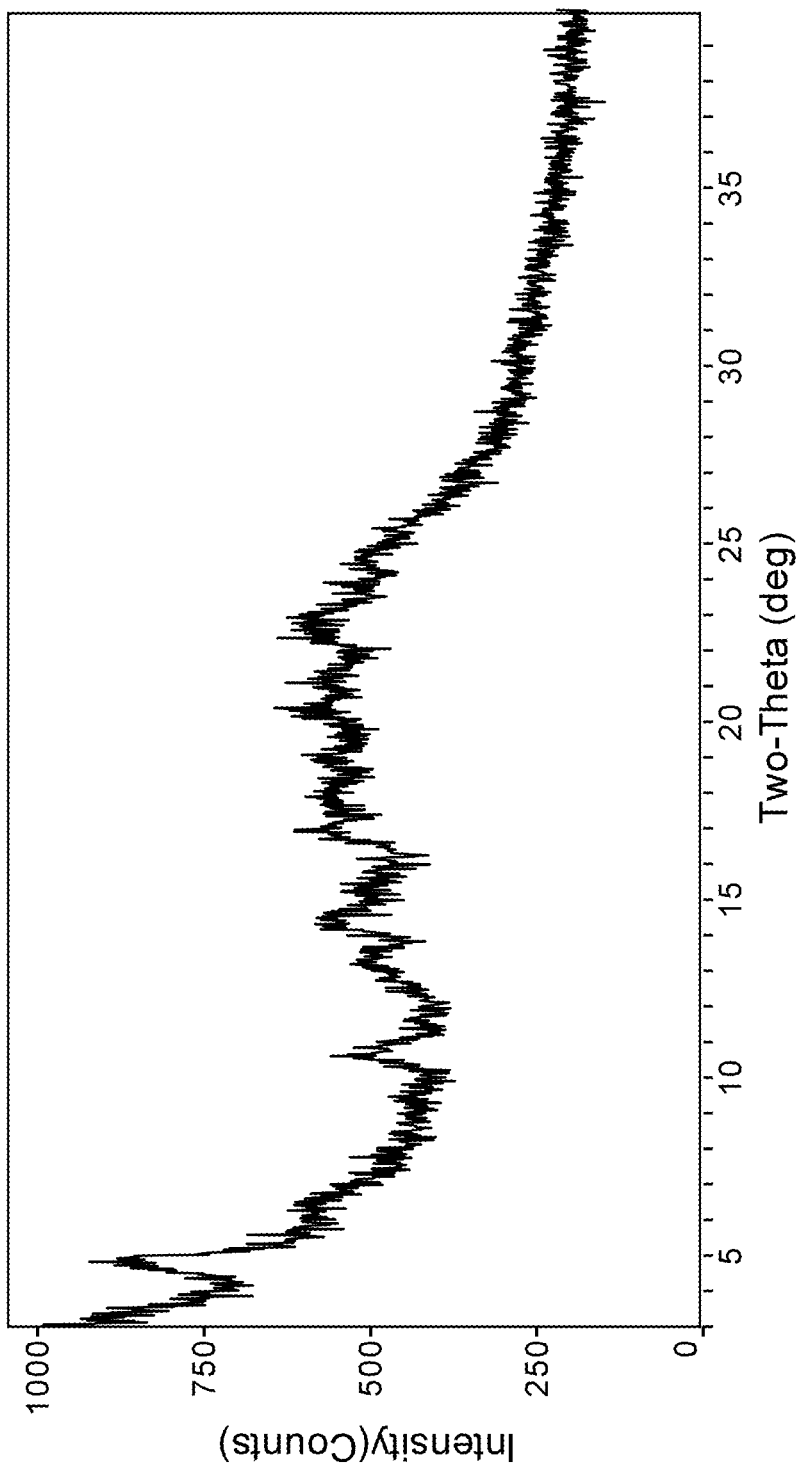

The solid was collected for XRPD analysis. The XRPD pattern of besylate Form O of compound (I) is shown in FIG. 21. Major peaks and their related intensities in the XRPD pattern are shown in table below.

Characterization Method

XRPD: Bruker D8 Advance diffractometer X-ray powder diffractometer with Cu-Kα radiation. Tube voltage was 40 KV and tube current was 40 mA. Scan range was from 3 to 40 degree 2-theta.

The step size was 0.02° at a scanning speed of 6°/min.

TABLE 19

X-ray powder diffraction peaks of besylate Form O of compound (I).

| Pos. [°2-theta] | Rel. Int. [%] |
| --- | --- |
| 4.9 | 100 |
| 10.6 | 68 |
| 13.2 | 41 |
| 14.3 | 51 |
| 16.9 | 48 |
| 17.9 | 21 |
| 19.1 | 33 |
| 20.2 | 31 |
| 21.1 | 40 |
| 22.4 | 54 |
| 22.9 | 55 |
| 23.9 | 35 |
| 24.4 | 32 |

Example 23

Preparation of Potassium Salt Form P of Compound (I)

10.02 mg of Form A of compound (I) as prepared in Example 3 was dissolved in 0.3 mL MeOH. 1.22 mg of potassium hydroxide (1.1 eq.) was added into the solution, which was agitated to obtain a clear solution. After being agitated for another 16 hours, the solvent was then reduced to 0.2 mL, and agitation continued at 10° C. for another 16hours. 3.0 mL n-heptane was added to the solution, then a small amount of solid precipitated. The solid was collected by centrifuge, and dried at 40° C. under vacuum for 24 hours.

Figure 22:
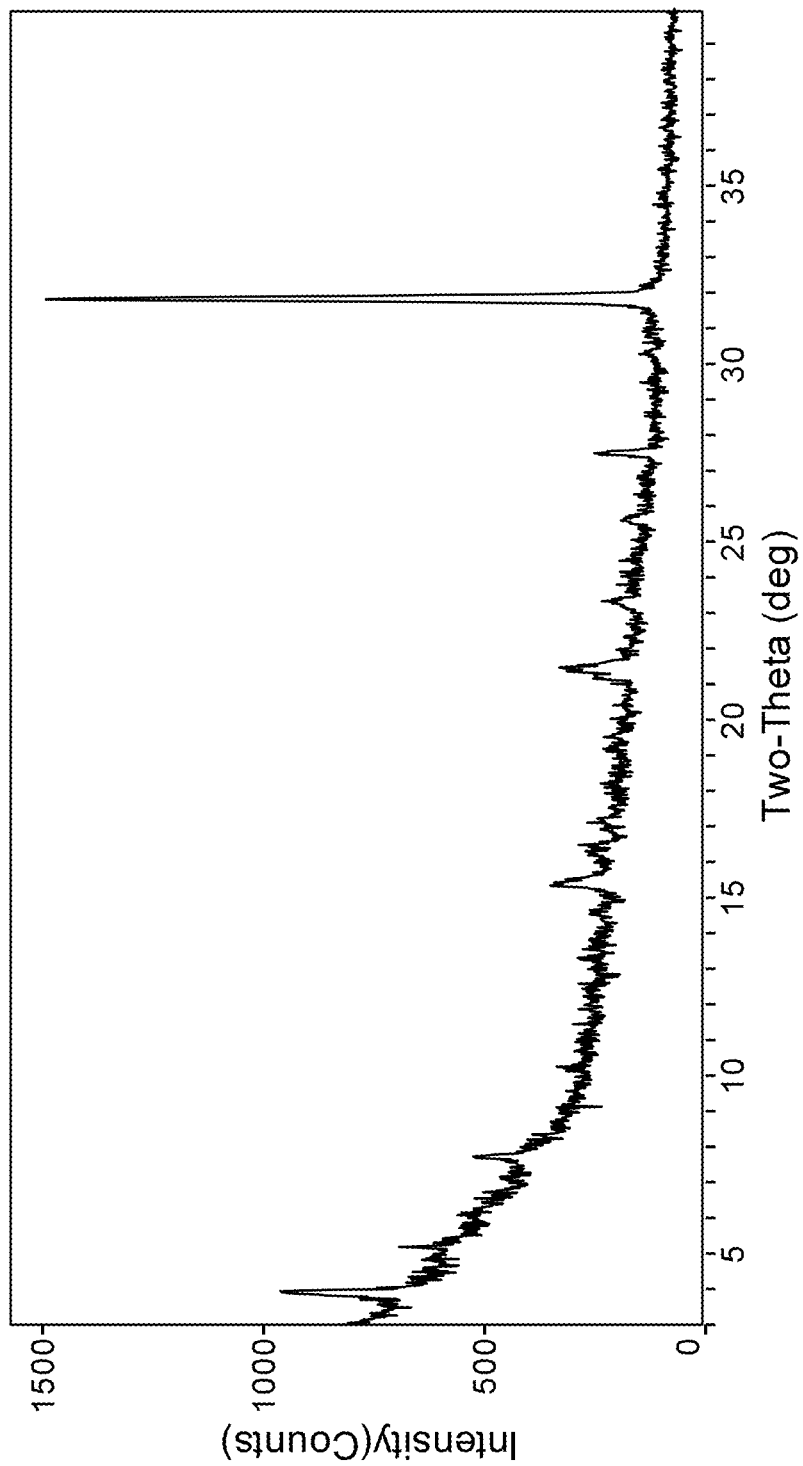

The solid was collected for XRPD analysis. The XRPD pattern of potassium salt Form P of compound (I) is shown in FIG. 22. Major peaks and their related intensities in the XRPD pattern are shown in table below.

Characterization Method

XRPD: Bruker D8 Advance diffractometer X-ray powder diffractometer with Cu-Kα radiation. Tube voltage was 40 KV and tube current was 40 mA. Scan range was from 3 to 40 degree 2-theta. The step size was 0.02° at a scanning speed of 6°/min.

TABLE 20

X-ray powder diffraction peaks of potassium salt Form P of compound (I).

| Pos. [°2-theta] | Rel. Int. [%] |
| --- | --- |
| 3.9 | 21 |
| 5.2 | 9 |
| 7.7 | 10 |
| 10.2 | 5 |
| 13.3 | 5 |
| 13.5 | 4 |
| 15.3 | 10 |
| 16.3 | 4 |
| 16.5 | 6 |
| 17.1 | 5 |
| 19.5 | 4 |
| 21.2 | 7 |
| 21.5 | 12 |

TABLE 20-continued

X-ray powder diffraction peaks of potassium salt Form P of compound (I).

| Pos. [°2-theta] | Rel. Int. [%] |
| --- | --- |
| 23.3 | 5 |
| 23.8 | 4 |
| 25.6 | 4 |
| 27.5 | 10 |
| 29.5 | 3 |
| 30.3 | 3 |
| 31.8 | 100 |

Example 24

Preparation of Potassium Salt Form Q of Compound (I)

705.70 mg of Form A of compound (I) as prepared in Example 1 was dissolved in 50 mL ethyl acetate. The solution in a vial was placed in a 40° C. water bath and agitated to ensure complete dissolution, then 218.28 mg of potassium phthalimide (1.0 eq.) was added and the solution turned slightly cloudy. The solution was stirred for 16 hours at RT which became significantly cloudy. The solid was collected by filtration and washed by 10 mL ethyl acetate, and dried at 40° C. in an air-blow oven for 5 hours.

Figure 23:
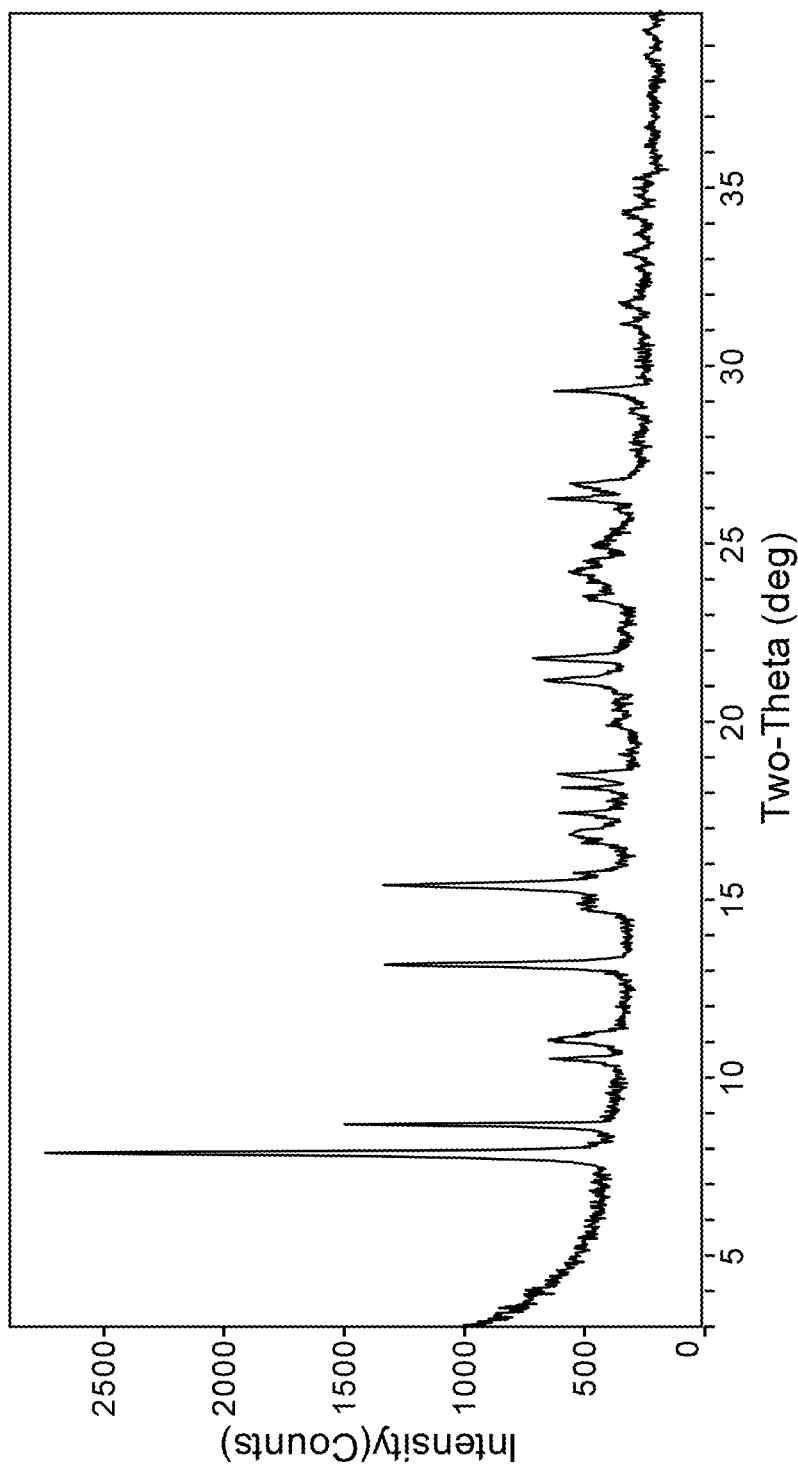

The solid was collected for XRPD analysis. The XRPD pattern of potassium salt Form Q of compound (I) is shown in FIG. 23. Major peaks and their related intensities in the XRPD pattern are shown in table below.

Experimental Conditions

XRPD: Bruker D8 Advance diffractometer X-ray powder diffractometer with Cu-Kα radiation. Tube voltage was 40 KV and tube current was 40 mA. Scan range was from 3 to 40 degree 2-theta. The step size was 0.02° at a scanning speed of 6°/min.

TABLE 21

X-ray powder diffraction peaks of potassium salt Form Q of compound (I).

| Pos. [°2-theta] | Rel. Int. [%] |
| --- | --- |
| 7.9 | 100 |
| 8.7 | 47 |
| 10.5 | 12 |
| 11.0 | 13 |
| 13.2 | 43 |
| 14.7 | 4 |
| 14.9 | 8 |
| 15.4 | 43 |
| 15.7 | 7 |
| 16.8 | 10 |
| 17.4 | 11 |
| 18.1 | 11 |
| 18.5 | 12 |
| 19.9 | 4 |
| 21.2 | 14 |
| 21.8 | 16 |
| 23.9 | 6 |
| 24.2 | 9 |
| 24.5 | 5 |
| 25.0 | 5 |
| 26.0 | 3 |
| 26.3 | 16 |
| 26.7 | 12 |
| 27.6 | 2 |
| 27.9 | 2 |
| 28.7 | 3 |
| 29.3 | 16 |
| 31.2 | 4 |
| 31.8 | 5 |

TABLE 21-continued

X-ray powder diffraction peaks of potassium
salt Form Q of compound (I).

| Pos. [°2-theta] | Rel. Int. [%] |
| --- | --- |
| 33.2 | 4 |
| 33.7 | 2 |
| 34.3 | 5 |
| 34.8 | 3 |
| 35.3 | 4 |
| 38.7 | 2 |
| 39.4 | 3 |

Example 25

Preparation of Potassium Salt Form R of Compound (I)

5.0 mg of potassium salt Form Q of compound (I) as prepared in Example 24 was suspended in 0.5 mL IPAc. The suspension was stirred at RT for 3 days.

Figure 24:
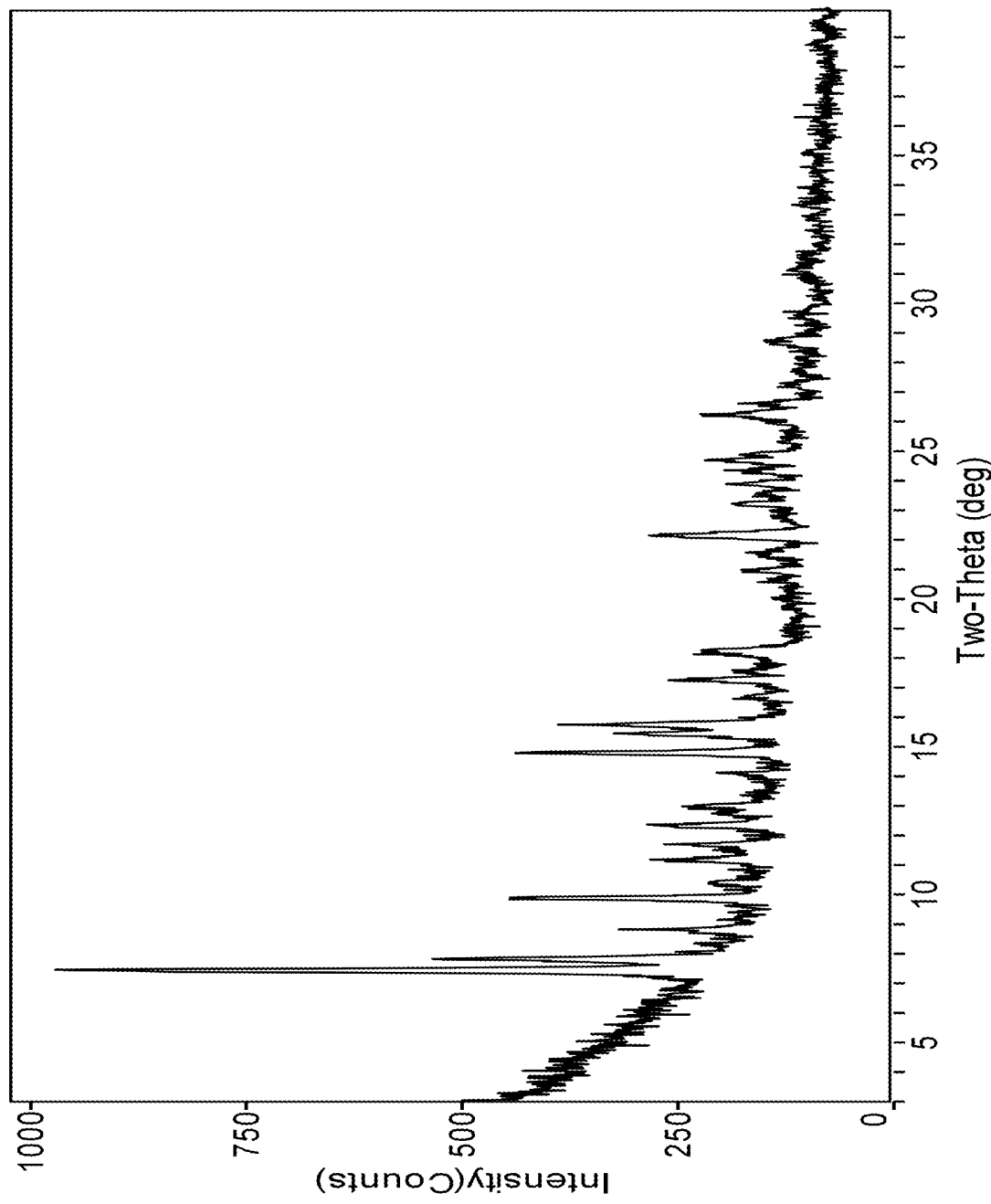

The solid was collected for XRPD analysis. The XRPD pattern of potassium salt Form R of compound (I) is shown in FIG. 24. Major peaks and their related intensities in the XRPD pattern are shown in table below.

Characterization Method

XRPD: Bruker D8 Advance diffractometer X-ray powder diffractometer with Cu-Kα radiation. Tube voltage was 40 KV and tube current was 40 mA. Scan range was from 3 to 40 degree 2-theta. The step size was 0.02° at a scanning speed of 6°/min.

TABLE 22

X-ray powder diffraction peaks of potassium
salt Form R of compound (I).

| Pos. [°2-theta] | Rel. Int. [%] |
| --- | --- |
| 7.5 | 100 |
| 7.8 | 42 |
| 8.8 | 18 |
| 9.9 | 37 |
| 10.4 | 7 |
| 11.2 | 16 |
| 11.7 | 15 |
| 12.4 | 18 |
| 13.0 | 13 |
| 14.1 | 8 |
| 14.8 | 39 |
| 15.4 | 25 |
| 15.7 | 33 |
| 17.2 | 16 |
| 17.6 | 8 |
| 18.3 | 12 |
| 20.6 | 5 |
| 21.0 | 8 |
| 21.6 | 7 |
| 22.2 | 23 |
| 23.2 | 9 |
| 23.9 | 8 |
| 24.3 | 9 |
| 24.7 | 12 |
| 26.3 | 15 |
| 26.6 | 10 |
| 27.3 | 5 |
| 28.8 | 8 |
| 31.1 | 5 |
| 36.3 | 5 |

Example 26

Preparation of Potassium Salt Form S of Compound (I)

10 mg of potassium salt Form Q of compound (I) as prepared in Example 24 was weighed into a variable temperature chamber. The sample was placed at 120° C. for 5 minutes.

Figure 25:
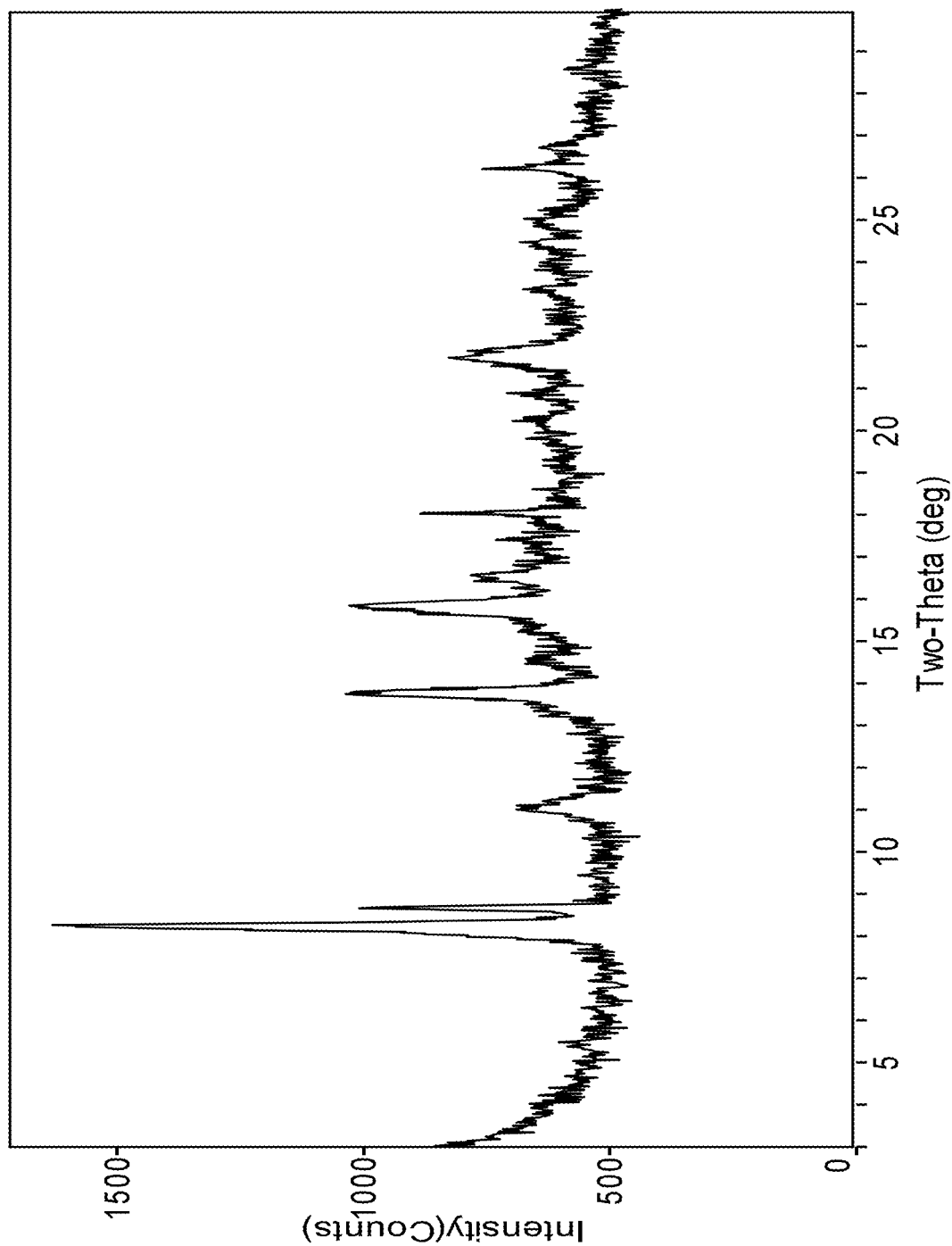

The solid was collected for XRPD analysis. The XRPD pattern of potassium salt Form S of compound (I) is shown in FIG. 25. Major peaks and their related intensities in the XRPD pattern are shown in table below.

Characterization Method:

XRPD: Bruker D8 Advance diffractometer X-ray powder diffractometer with Cu-Kα radiation. Tube voltage was 40 KV and tube current was 40 mA. Scan range was from 3 to 30 degree 2-theta. The step size was 0.02° at a scanning speed of 6°/min.

TABLE 23

X-ray powder diffraction peaks of potassium
salt Form S of compound (I).

| Pos. [°2-theta] | Rel. Int. [%] |
| --- | --- |
| 5.5 | 7 |
| 8.3 | 100 |
| 8.7 | 44 |
| 11.0 | 17 |
| 11.2 | 11 |
| 12.1 | 7 |
| 13.4 | 11 |
| 13.7 | 44 |
| 14.6 | 8 |
| 15.8 | 37 |
| 16.6 | 12 |
| 18.0 | 25 |
| 19.8 | 7 |
| 20.3 | 7 |
| 20.9 | 9 |
| 21.7 | 20 |
| 24.5 | 9 |
| 24.9 | 7 |
| 26.2 | 19 |
| 26.7 | 9 |
| 28.6 | 9 |

Example 27

Preparation of Calcium Salt Form T of Compound (I)

20.04 mg of Sodium salt Form J of compound (I) as prepared in Example 15 was dissolved in 0.7 mL water at RT, to which was added 4.10 mg anhydrous calcium chloride (1.1 eq.) in 0.1 mL water, and an emulsion like white suspension formed. Additional 0.4 mL water was added and the suspension was agitated at RT for 1.5 hours. The solid was collected by centrifugation and dried for 16 hours at 40° C. in a vacuum oven.

Figure 26:
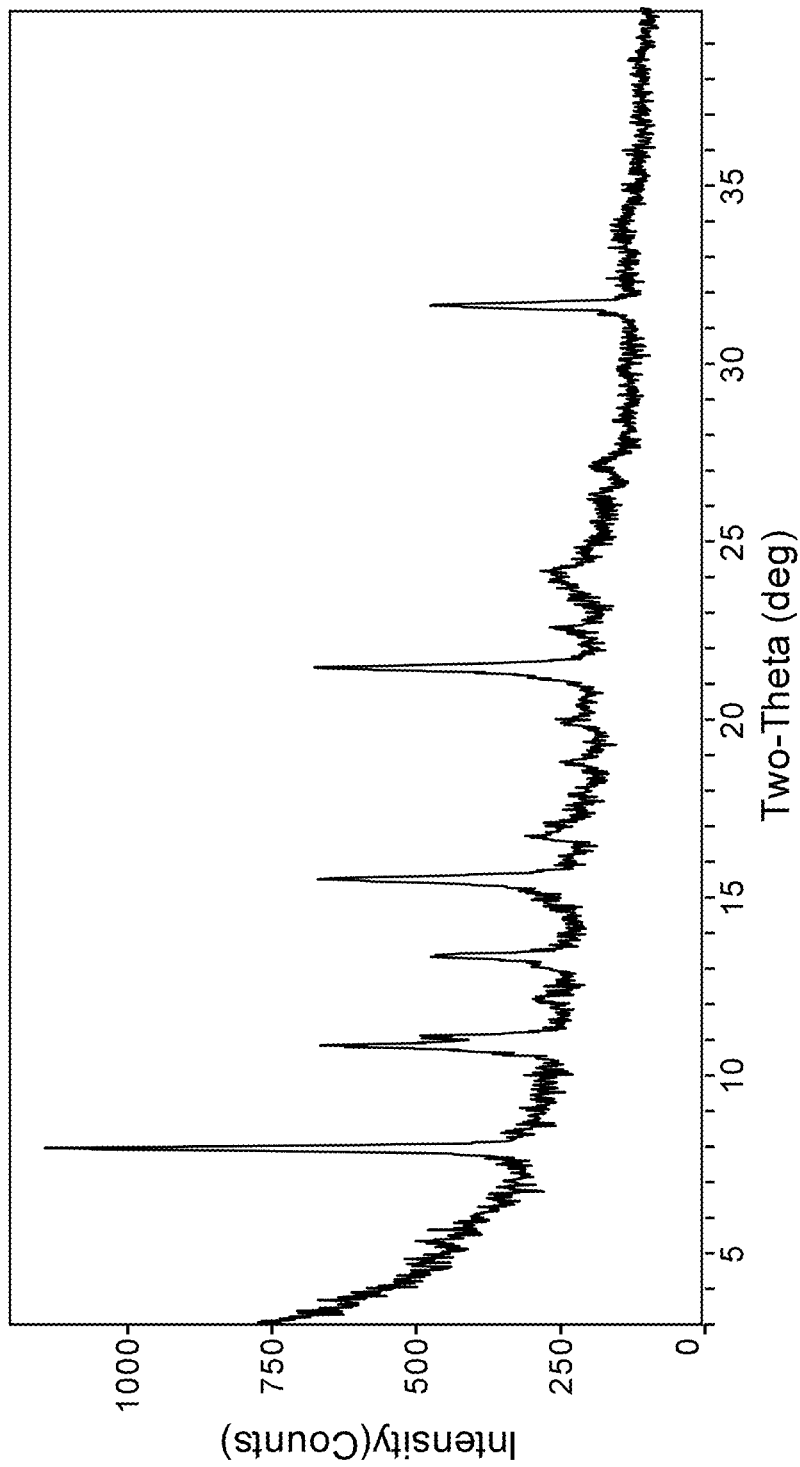

The solid was collected for XRPD analysis. The XRPD pattern of calcium salt Form T of compound (I) is shown in FIG. 26. Major peaks and their related intensities in the XRPD pattern are shown in table below.

Characterization Method:

XRPD: Bruker D8 Advance diffractometer X-ray powder diffractometer with Cu-Kα radiation. Tube voltage was 40 KV and tube current was 40 mA. Scan range was from 3 to 40 degree 2-theta. The step size was 0.02° at a scanning speed of 6°/min.

TABLE 24

X-ray powder diffraction peaks of calcium
salt Form T of compound (I).

| Pos. [°2-theta] | Rel. Int. [%] |
|---|---|
| 5.3 | 10 |
| 8.0 | 100 |
| 10.8 | 48 |
| 11.1 | 29 |
| 13.3 | 29 |
| 14.9 | 9 |
| 15.5 | 52 |
| 16.7 | 12 |
| 17.1 | 8 |
| 18.8 | 8 |
| 20.0 | 8 |
| 21.5 | 57 |
| 22.6 | 9 |
| 23.9 | 9 |
| 24.2 | 12 |
| 27.1 | 7 |
| 31.6 | 41 |
| 36.0 | 4 |

Example 28

Preparation of Calcium Salt Form U of Compound (I)

304.32 mg of sodium salt Form J of compound (I) as prepared in Example 15 was dissolved in 10 mL water at RT with sonication. About 59.90 mg of anhydrous calcium chloride (1.1 eq.) in 1.0 mL water was added dropwise to the above solution, the solution instantly became cloudy. After 1 hour of agitation at RT, the suspension became sticky and solidified. It became flowable after addition of 4.0 mL water with agitation for 16 hours at RT, the solid was collected by filtration under vacuum, washed with a small amount of water and dried at 40° C. in an air-blow oven for 16 hours.

Figure 27:
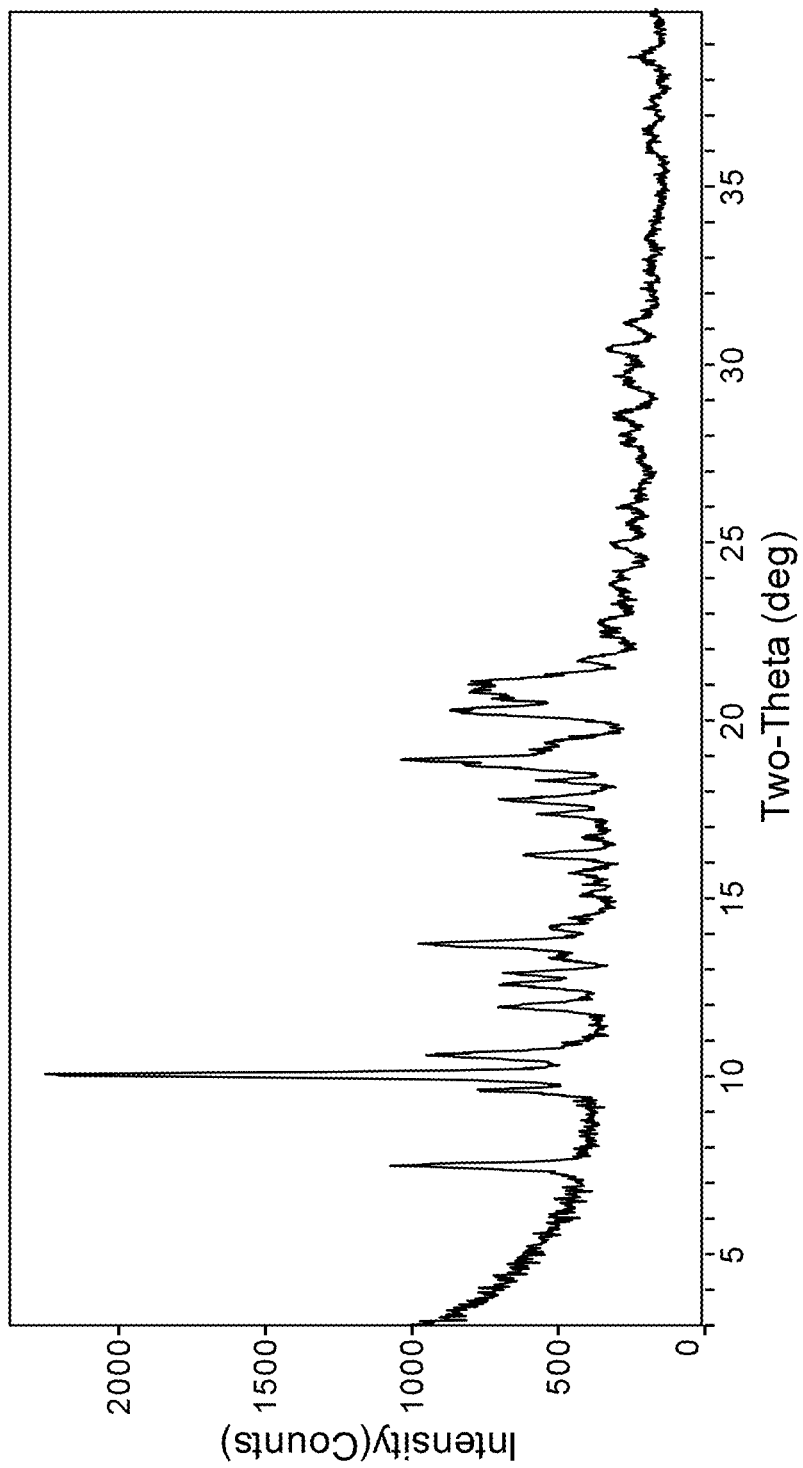

The solid was collected for XRPD analysis. The XRPD pattern of calcium salt Form U of compound (I) is shown in FIG. 27. Major peaks and their related intensities in the XRPD pattern are shown in table below.

Characterization Method:

XRPD: Bruker D8 Advance diffractometer X-ray powder diffractometer with Cu-Kα radiation. Tube voltage was 40 KV and tube current was 40 mA. Scan range was from 3 to 40 degree 2-theta. The step size was 0.02° at a scanning speed of 6°/min.

TABLE 25

X-ray powder diffraction peaks of calcium
salt Form U of compound (I).

| Pos. [°2-theta] | Rel. Int. [%] |
|---|---|
| 7.5 | 36 |
| 9.6 | 15 |
| 10.1 | 100 |
| 10.6 | 27 |
| 11.9 | 17 |
| 12.6 | 18 |
| 12.9 | 17 |
| 13.3 | 8 |
| 13.7 | 34 |
| 14.2 | 9 |
| 15.1 | 5 |
| 15.7 | 7 |
| 16.2 | 15 |
| 16.7 | 4 |
| 17.4 | 13 |
| 17.8 | 20 |
| 18.3 | 12 |
| 18.9 | 39 |
| 19.4 | 12 |
| 20.3 | 27 |
| 21.0 | 26 |
| 21.7 | 7 |
| 22.5 | 5 |
| 22.7 | 5 |
| 23.8 | 4 |
| 24.2 | 5 |
| 25.0 | 6 |
| 25.5 | 3 |
| 26.0 | 5 |
| 26.5 | 3 |
| 27.9 | 4 |
| 28.0 | 6 |
| 28.6 | 6 |
| 29.4 | 4 |
| 29.7 | 5 |
| 30.4 | 7 |
| 31.2 | 5 |
| 32.1 | 3 |
| 32.6 | 3 |
| 33.0 | 3 |
| 36.0 | 3 |
| 36.6 | 4 |
| 37.5 | 2 |
| 38.6 | 4 |

Example 29

Preparation of Ammonium Salt Form V of Compound (I)

10.34 mg of Form A of compound (I) as prepared in Example 3 was dissolved in 0.3 mL methanol at RT. 2.66 mg of ammonia solution (1.1 eq., 25%-28%) was added to the solution, the mixture was clear but precipitation occurred after 16 hours of agitation. After removing all the solvents, an oil was obtained. 0.05 mL acetonitrile and 0.4 mL IPE was added to the residue, solid formed and was collected by filtration, dried in a vacuum oven for 16 hours.

Figure 28:
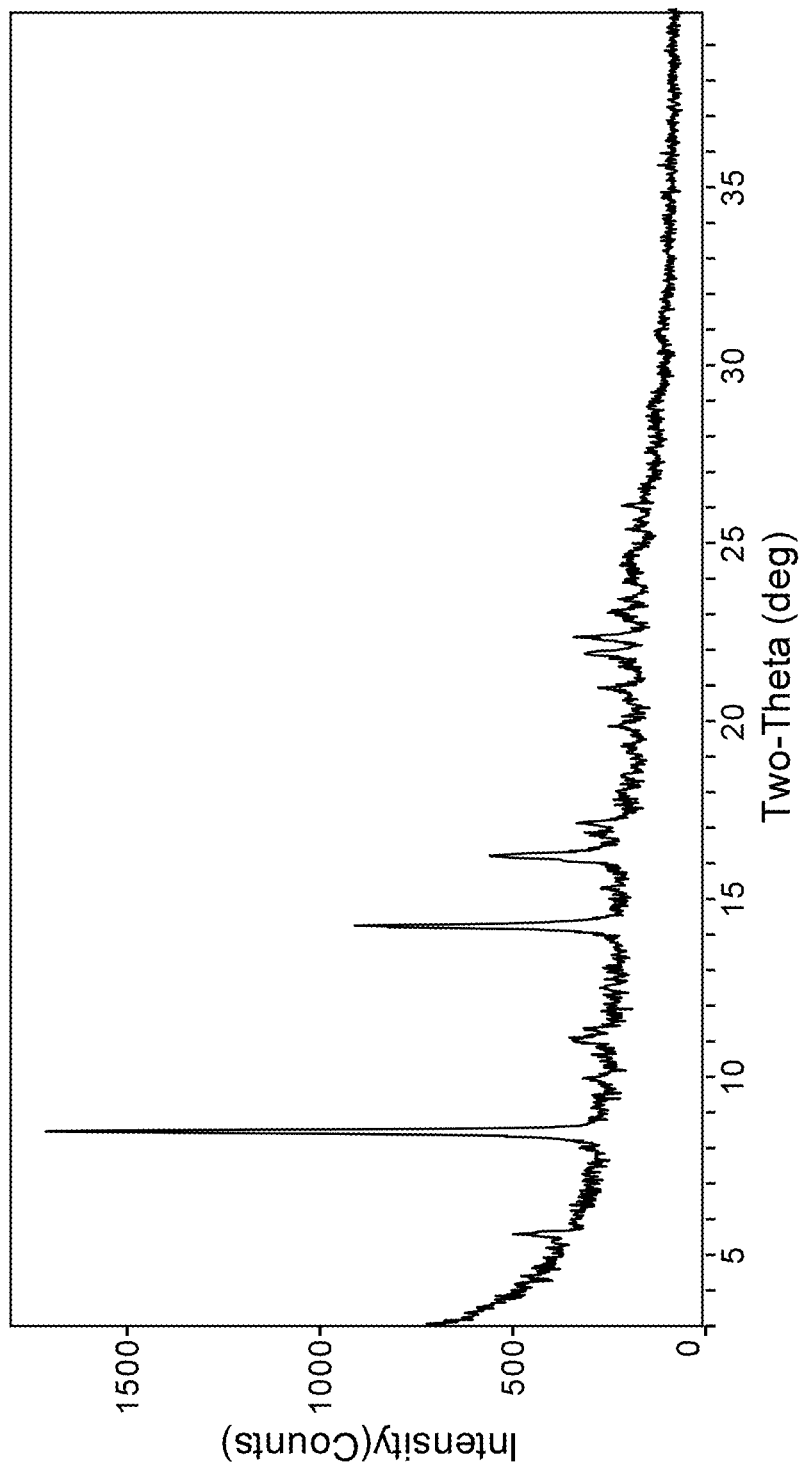

The solid was collected for XRPD analysis. The XRPD pattern of ammonium Salt Form V of compound (I) is shown in FIG. 28. Major peaks and their related intensities in the XRPD pattern are shown in table below.

Characterization Method

XRPD: Bruker D8 Advance diffractometer X-ray powder diffractometer with Cu-Kα radiation. Tube voltage was 40 KV and tube current was 40 mA. Scan range was from 3 to 40 degree 2-theta. The step size was 0.02° at a scanning speed of 6°/min.

TABLE 26

X-ray powder diffraction peaks of ammonium
Salt Form V of compound (I).

| Pos. [°2-theta] | Rel. Int. [%] |
|---|---|
| 5.6 | 10 |
| 8.0 | 4 |
| 8.5 | 100 |
| 10.0 | 5 |
| 10.6 | 4 |
| 11.1 | 8 |
| 11.4 | 5 |
| 14.2 | 48 |
| 15.3 | 4 |
| 16.2 | 23 |

TABLE 26-continued

X-ray powder diffraction peaks of ammonium Salt Form V of compound (I).

| Pos. [°2-theta] | Rel. Int. [%] |
|---|---|
| 16.9 | 7 |
| 17.1 | 8 |
| 19.3 | 3 |
| 19.9 | 6 |
| 20.9 | 8 |
| 21.5 | 3 |
| 21.9 | 10 |
| 22.4 | 11 |
| 23.1 | 6 |
| 23.4 | 4 |
| 24.4 | 4 |
| 24.7 | 3 |
| 25.4 | 4 |
| 26.1 | 5 |
| 28.8 | 3 |
| 35.6 | 3 |

Example 30

Preparation of Ammonium Salt Form W of Compound (I)

10.47 mg of Form A of compound (I) as prepared in Example 3 was dissolved in 1.0 mL acetonitrile at 50° C., then the solution was cooled down to RT. 2.69 mg of ammonia solution (1.1 eq., 25%-28%) to the solution and the mixture was clear, and precipitation occurred after 16 hours of agitation. The amount of solvent was reduced to 0.2 mL and agitation continued for 3 days at 10° C. The solids were collected by filtration, dried in a vacuum oven for 16 hours.

The solid was collected for XRPD analysis.

Figure 29:
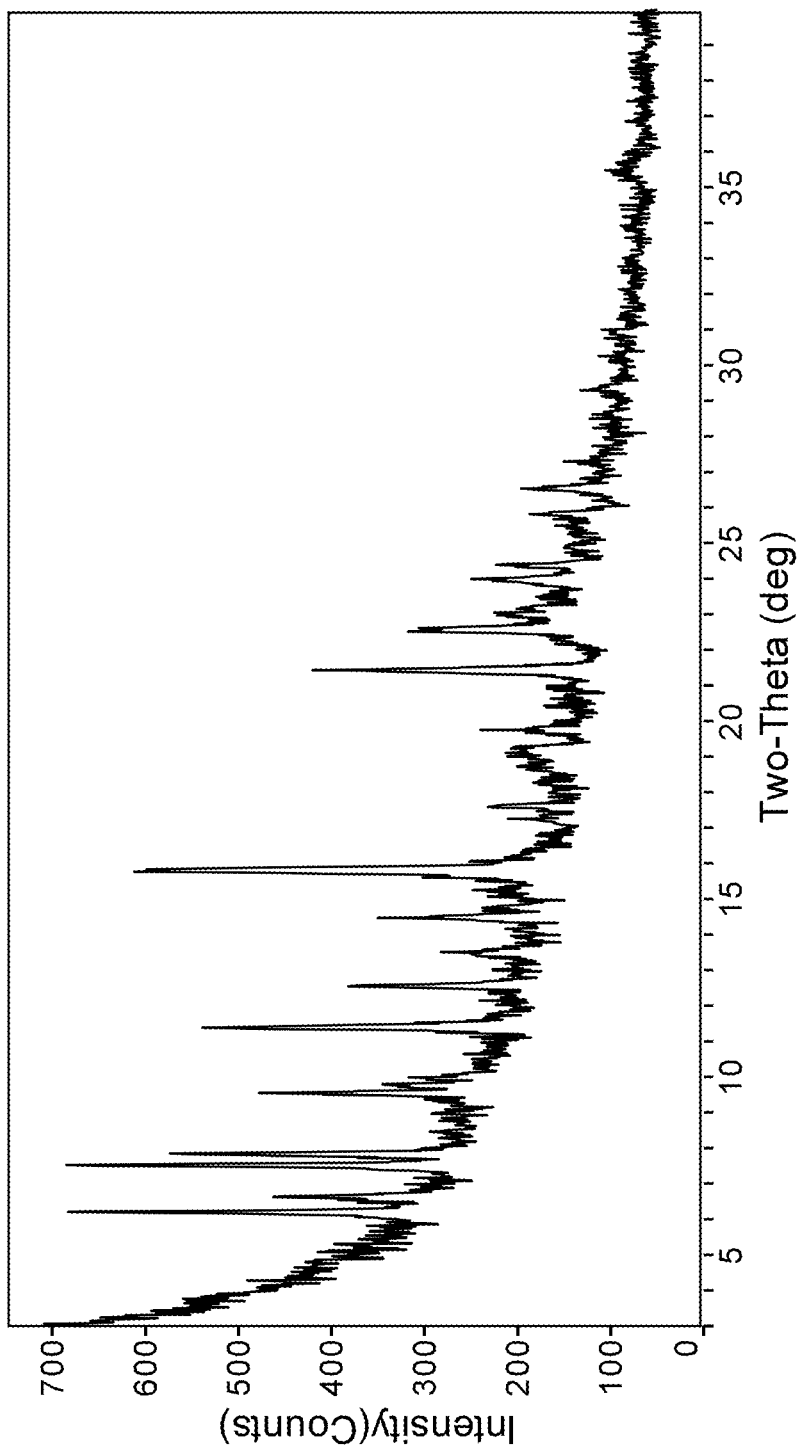

The XRPD pattern of ammonium salt Form W of compound (I) is shown in FIG. 29. Major peaks and their related intensities in the XRPD pattern are shown in table below.

Characterization Method

XRPD: Bruker D8 Advance diffractometer X-ray powder diffractometer with Cu-Kα radiation. Tube voltage was 40 KV and tube current was 40 mA. Scan range was from 3 to 40 degree 2-theta. The step size was 0.02° at a scanning speed of 6°/min.

TABLE 27

X-ray powder diffraction peaks of ammonium salt Form W of compound (I).

| Pos. [°2-theta] | Rel. Int. [%] |
|---|---|
| 6.2 | 85 |
| 6.6 | 39 |
| 7.5 | 94 |
| 7.8 | 70 |
| 9.5 | 53 |
| 9.9 | 24 |
| 10.0 | 18 |
| 11.4 | 74 |
| 12.5 | 41 |
| 13.5 | 21 |
| 14.5 | 38 |
| 14.7 | 13 |
| 15.2 | 14 |
| 15.8 | 100 |
| 17.2 | 14 |
| 17.6 | 19 |
| 18.7 | 13 |
| 19.1 | 17 |
| 19.2 | 14 |
| 19.8 | 24 |
| 21.4 | 67 |
| 22.5 | 42 |
| 23.0 | 20 |
| 24.0 | 25 |
| 24.4 | 20 |
| 25.8 | 19 |
| 26.5 | 21 |
| 27.3 | 11 |
| 29.3 | 9 |
| 31.0 | 8 |
| 35.4 | 9 |

Example 31

Preparation of Ammonium Salt Form X of Compound (I)

400.46 mg of Form A of compound (I) as prepared in Example 3 was dissolved in 30 mL ACN at 65° C. and cooled to RT. 100.35 mg of ammonia solution (1.1 eq., 25%-28%) was added to the solution under agitation, the solution instantly turned cloudy. The suspension was agitated for 17 hours at RT. The solid was collected by filtration, washed with a small amount of acetonitrile and dried in a vacuum oven for 5 hours.

Figure 30:
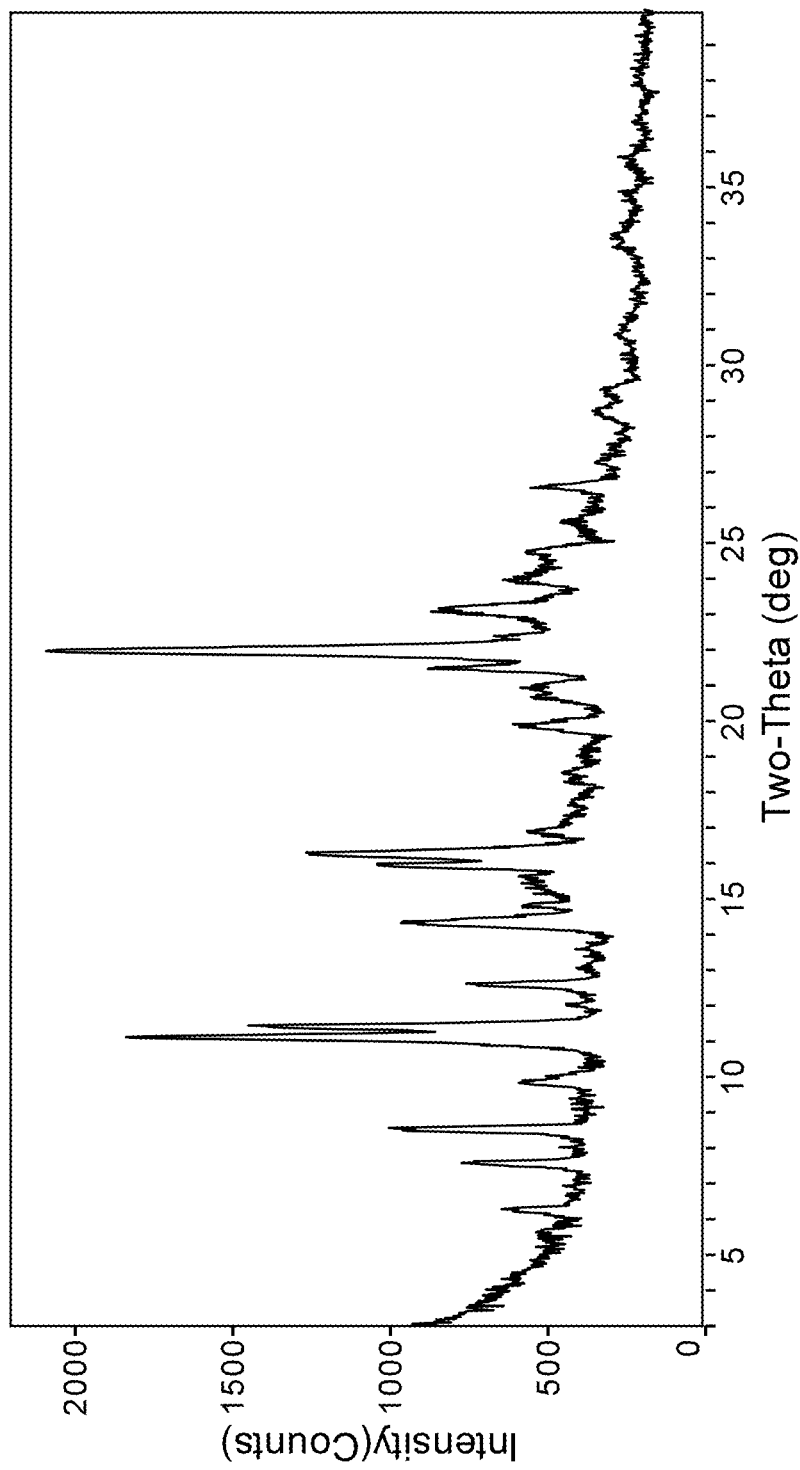

The solid was collected for XRPD analysis. The XRPD pattern of ammonium salt Form X of compound (I) is shown in FIG. 30. Major peaks and their related intensities in the XRPD pattern are shown in table below.

Characterization Method

XRPD: Bruker D8 Advance diffractometer X-ray powder diffractometer with Cu-Kα radiation. Tube voltage was 40 KV and tube current was 40 mA. Scan range was from 3 to 40 degree 2-theta. The step size was 0.02° at a scanning speed of 6°/min.

TABLE 28

X-ray powder diffraction peaks of ammonium salt Form X of compound (I).

| Pos. [°2-theta] | Rel. Int. [%] |
|---|---|
| 6.3 | 14 |
| 7.6 | 23 |
| 8.0 | 5 |
| 8.6 | 38 |
| 9.8 | 14 |
| 11.1 | 91 |
| 11.4 | 67 |
| 12.0 | 5 |
| 12.6 | 25 |
| 13.6 | 5 |
| 14.3 | 35 |
| 14.8 | 10 |
| 15.4 | 5 |
| 15.6 | 10 |
| 16.0 | 37 |
| 16.3 | 48 |
| 16.9 | 9 |

TABLE 28-continued

X-ray powder diffraction peaks of ammonium salt Form X of compound (I).

| Pos. [°2-theta] | Rel. Int. [%] |
|---|---|
| 18.3 | 6 |
| 18.6 | 6 |
| 19.0 | 4 |
| 19.8 | 16 |
| 20.7 | 11 |
| 20.9 | 12 |
| 21.5 | 26 |
| 22.0 | 100 |
| 23.2 | 23 |
| 24.0 | 14 |
| 24.8 | 12 |
| 25.6 | 7 |
| 26.6 | 14 |
| 27.3 | 4 |
| 28.7 | 7 |
| 29.3 | 6 |
| 30.9 | 4 |
| 31.1 | 3 |
| 33.3 | 5 |
| 33.7 | 5 |
| 34.9 | 4 |
| 35.6 | 4 |
| 35.9 | 5 |
| 36.8 | 3 |
| 37.9 | 3 |

Example 33

Stability of Solid Forms 40 mg of compound (I) in different solid forms were stored in a stability chamber with temperature and humidity controlled at 40° C. and 75%-RH, respectively. After 1 month, the samples were analyzed by XRPD to check their solid form and compared with their initial solid form. According to the results shown in Table 29. Form D and sodium salt Form J showed better solid form stability than the original Form D as prepared in Example 1.

TABLE 29

Physical stability data of different solid forms of compound (I)

| | | Physical stability |
|---|---|---|
| Samples | Initial | 40° C./75%-RH, 1 month |
| Example 1, Form D of compound (I) | Form D | solid form change |
| Example 15, sodium salt Form J of compound (I) | Form J | no solid form change |

Example 34

Apparent Solubility Study

Apparent solubility was determined by suspending 5 mg of compound (I) in different bio-relevant media including pH buffers (50 mM). The suspensions were equilibrated at 25° C. for 24 hours. The suspensions were then filtered through a 0.22 μm PVDF filter into a 2-mL HPLC vial. The quantification of the filtrate was conducted by HPLC with reference to a standard solution. The solubility results of selected novel solid forms in this invention are shown in Table 30. The novel solid forms Form H, Form J, and Form Q of this invention showed higher solubility than Form A at pH7 and pH9.

TABLE 30

Apparent solubility of different solid forms of (I)

| | Sample | | | | | | | |
|---|---|---|---|---|---|---|---|---|
| | Example 3, Form A of compound (I) | | Example 16, Form H of compound (I) | | Example 15, sodium salt Form J of compound (I) | | Example 24, potassium salt Form Q of compound (I) | |
| pH | Solubility (mg/mL) | Final pH | Solubility (mg/mL) | Final pH | Solubility (mg/mL) | Final pH | Solubility (mg/mL) | Final pH |
| pH 1 | 0.94 | 1.05 | 1.581 | 1.08 | 1.51 | 1.12 | 1.56 | 1.1 |
| pH 3 | 0.066 | 2.97 | 0.056 | 3.01 | 0.016 | 3.53 | 0.00 | 3.49 |
| pH 5 | 0.004 | 4.99 | 0.006 | 5.03 | 0.0028 | 5.22 | 0.00 | 5.17 |
| pH 7 | 0.072 | 6.98 | 0.244 | 6.97 | 0.69 | 7.34 | 3.58 | 6.97 |
| pH 9 | 4.82 | 8.46 | >10 | 8.90 | >10 | 8.80 | >10 | 8.71 |

Example 35

Solubility and Stability Study of Form H

Apparent solubility in water was determined by suspending 5 mg of compound (I) in purified water. The suspensions were equilibrated at 25° C. for 24 hours. The suspensions were then filtered through a 0.22 μm PVDF filter into a 2-mL HPLC vial. The quantitation of the filtrate was conducted by HPLC with reference to a standard solution. The solids were analyzed by XRPD. The solubility study results of selected novel solid forms in this invention are shown in Table 31.

TABLE 31

Physical stability data of different solid forms of compound (I)

| Samples | Solubility (mg/mL) | Final pH | XRPD of residue |
|---|---|---|---|
| Example 3, Form A of compound (I) | 0.05 | 6.97 | Form A |

TABLE 31-continued

Physical stability data of different solid forms of compound (I)

| Samples | Solubility (mg/mL) | Final pH | XRPD of residue |
|---|---|---|---|
| Example 16, Form H of compound (I) | 0.453 | 7.35 | Form H |

Surprisingly, the monohydrate Form H shows significant higher water solubility than the anhydrate Form A.

20 mg of compound (I) in different solid forms were stored in a stability chamber with temperature and humidity controlled at 25° C. and 60%-RH. After 1 month, the samples were analyzed by XRPD to check their solid form and compared with their initial solid form. Form H showed better stability than the original Form D as prepared in Example 1.

TABLE 32

Physical stability data of different solid forms of compound (I)

| | Physical stability | |
|---|---|---|
| Samples | Initial | 25° C./60%-RH, 1 month |
| Example 1, Form D of compound (I) | Form D | solid form change |
| Example 16, Form H of compound (I) | Form H | no solid form change |

With unexpected higher water solubility and acceptable solid state stability, Form H of compound (I) whose absorption is limited by solubility could be further developed as solid dosage forms to better improve absorption.

The invention claimed is:

1. A solid form of compound (I),

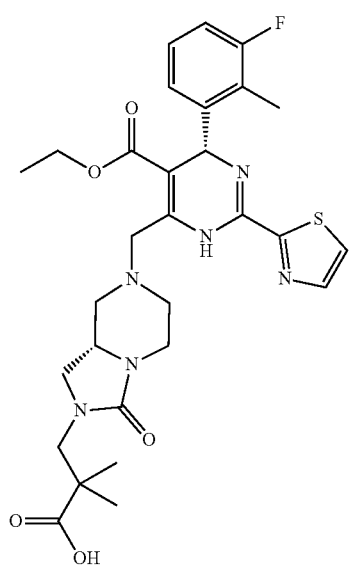

(I)

wherein the solid form is Form A, Form B, Form C, Form D, Form E, Form F, Form G, Form H, or Form I.

2. A solid form according to claim 1, wherein the solid form is Form A that exhibits an X-ray powder diffraction (XRPD) pattern with characteristic peaks expressed in degrees 2-theta at 10.0°±0.2°, 14.5°±0.2°, 15.4°±0.2°, 16.4°±0.2°, 19.4°±0.2°, 21.1°±0.2° and 23.2°±0.2°.

3. A solid form according to claim 2, wherein the solid form is Form A that exhibits an X-ray powder diffraction (XRPD) pattern with characteristic peaks expressed in degrees 2-theta at 10.0°±0.2°, 12.3°±0.2°, 13.2°±0.2°, 14.5°±0.2°, 15.4°±0.2°, 16.4°±0.2°, 19.4°±0.2°, 20.3°±0.2°, 21.1°±0.2°, 21.6°±0.2°, 23.2°±0.2°, 23.7°±0.2°, 24.5°±0.2°, 25.5°±0.2° and 26.8°±0.2°.

4. A solid form according to claim 2, wherein the solid form is Form A that exhibits an X-ray powder diffraction (XRPD) pattern shown in FIG. 2.

5. A solid form according to claim 1, wherein the solid form is Form B that exhibits an X-ray powder diffraction (XRPD) pattern with characteristic peaks expressed in degrees 2-theta at 3.9°±0.2°, 4.8°±0.2°, 7.3°±0.2°, 7.8°±0.2°, 10.7°±0.2°, 15.6°±0.2° and 19.5°±0.2°.

6. A solid form according to claim 1, wherein the solid form is Form B that exhibits an X-ray powder diffraction (XRPD) pattern with characteristic peaks expressed in degrees 2-theta at 3.9°±0.2°, 4.8°±0.2°, 7.3°±0.2°, 7.8°±0.2°, 10.7°±0.2°, 15.6°±0.2°, 16.2°±0.2°, 16.4°±0.2°, 19.5°±0.2°, 20.4°±0.2° and 21.7°±0.2°.

7. A solid form according to claim 1, wherein the solid form is Form C that exhibits an X-ray powder diffraction (XRPD) pattern with characteristic peaks expressed in degrees 2-theta at 5.1°±0.2°, 10.6°±0.2°, 10.8°±0.2°, 12.1°±0.2°, 13.6°±0.2° and 13.9°±0.2°.

8. A solid form according to claim 1, wherein the solid form is Form D that exhibits an X-ray powder diffraction (XRPD) pattern with characteristic peaks expressed in degrees 2-theta at 6.8°±0.2°, 13.0°±0.2°, 20.3°±0.2°, 27.1°±0.2°, 27.4°±0.2°, 28.8°±0.2° and 29.1°±0.2°.

9. A solid form according to claim 1, wherein the solid form is Form E that exhibits an X-ray powder diffraction (XRPD) pattern with characteristic peaks expressed in degrees 2-theta at 4.0°±0.2°, 5.1°±0.2°, 5.4°±0.2°, 10.2°±0.2°, 13.3°±0.2°, 15.5°±0.2° and 20.2°±0.2°.

10. A solid form according to claim 1, wherein the solid form is Form E that exhibits an X-ray powder diffraction (XRPD) pattern with characteristic peaks expressed in degrees 2-theta at 4.0°±0.2°, 5.1°±0.2°, 5.4°±0.2°, 10.2°±0.2°, 10.5°±0.2°, 11.8°±0.2°, 12.2°±0.2°, 13.3°±0.2°, 13.8°±0.2°, 14.6°±0.2°, 15.5°±0.2°, 15.8°±0.2°, 16.5°±0.2°, 19.5°±0.2°, 20.2°±0.2° and 21.9°±0.2°.

11. A solid form according to claim 1, wherein the solid form is Form F that exhibits an X-ray powder diffraction (XRPD) pattern with characteristic peaks expressed in degrees 2-theta at 4.0°±0.2°, 4.9°±0.2°, 7.1°±0.2°, 15.8°±0.2°, 20.3°±0.2° and 21.9°±0.2°.

12. A solid form according to claim 1, wherein the solid form is Form F that exhibits an X-ray powder diffraction (XRPD) pattern with characteristic peaks expressed in degrees 2-theta at 4.0°±0.2°, 4.9°±0.2°, 7.1°±0.2°, 7.4°±0.2°, 7.9°±0.2°, 10.6°±0.2°, 11.9°±0.2°, 13.1°±0.2°, 13.3°±0.2°, 13.8°±0.2°, 15.8°±0.2°, 20.3°±0.2°, 21.0°±0.2° and 21.9°±0.2°.

13. A solid form according to claim 1, wherein the solid form is Form G that exhibits an X-ray powder diffraction (XRPD) pattern with characteristic peaks expressed in degrees 2-theta at 3.7°±0.2°, 4.1°±0.2°, 5.0°±0.2°, 6.2°±0.2°, 7.7°±0.2°, 8.2°±0.2° and 17.1°±0.2°.

14. A solid form according to claim 1, wherein the solid form is Form G that exhibits an X-ray powder diffraction (XRPD) pattern with characteristic peaks expressed in degrees 2-theta at 3.7°±0.2°, 4.1°±0.2°, 5.0°±0.2°, 6.2°±0.2°, 7.7°±0.2°, 8.2°±0.2°, 11.3°±0.2°, 13.3°±0.2°, 13.8°±0.2°, 14.5°±0.2°, 16.3°±0.2°, 17.1°±0.2°, 19.3°±0.2°, 21.1°±0.2° and 23.3°±0.2°.

15. A solid form according to claim 1, wherein the solid form is Form H that exhibits an X-ray powder diffraction (XRPD) pattern with characteristic peaks expressed in degrees 2-theta at 8.0°±0.2°, 9.7°±0.2°, 14.6°±0.2°, 15.7°±0.2°, 15.9°±0.2° and 24.1°±0.2°.

16. A solid form according to claim 1, wherein the solid form is Form H that exhibits an X-ray powder diffraction (XRPD) pattern with characteristic peaks expressed in degrees 2-theta at 6.8°±0.2°, 8.0°±0.2°, 9.7°±0.2°, 11.6°±0.2°, 14.6°±0.2°, 15.2°±0.2°, 15.7°±0.2°, 15.9°±0.2°, 18.9°±0.2°, 19.9°±0.2°, 22.7°±0.2°, 24.1°±0.2°, 24.5°±0.2° and 26.0°±0.2°.

17. A solid form according to claim 1, wherein the solid form is Form I that exhibits an X-ray powder diffraction (XRPD) pattern with characteristic peaks expressed in degrees 2-theta at 6.4°±0.2°, 7.8°±0.2°, 9.9°±0.2°, 11.6°±0.2°, 16.2°±0.2° and 22.1°±0.2°.

18. A solid form according to claim 1, wherein the solid form is Form I that exhibits an X-ray powder diffraction (XRPD) pattern with characteristic peaks expressed in degrees 2-theta at 6.4°±0.2°, 7.8°±0.2°, 9.6°±0.2°, 9.9°±0.2°, 11.6°±0.2°, 13.0°±0.2°, 14.5°±0.2°, 15.0°±0.2°, 15.7°±0.2°, 16.2°±0.2°, 18.3°±0.2°, 22.1°±0.2°, 23.0°±0.2°, 24.3°±0.2° and 27.2°±0.2°.

19. A pharmaceutical composition comprising the solid form of claim 1 and a pharmaceutically acceptable carrier, excipient, diluent, adjuvant, or vehicle, or a combination thereof.

20. A solid form of a compound (I),

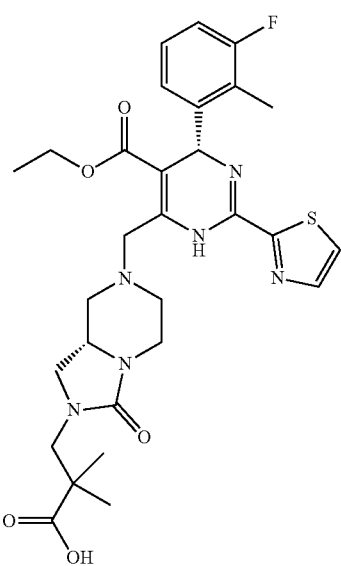

(I)

wherein the solid form is Form Amorphous that exhibits an X-ray powder diffraction (XRPD) pattern shown in FIG. 4.

* * * * *